(12) United States Patent
Yuan

(10) Patent No.: US 12,409,234 B1
(45) Date of Patent: Sep. 9, 2025

(54) NANOPARTICLES COMPRISING A FUNCTIONAL AGENT AND METHOD OF PREPARATION AND USE THEREOF

(71) Applicant: Yumin Yuan, Jiaxing (CN)

(72) Inventor: Yumin Yuan, Jiaxing (CN)

( * ) Notice: Subject to any disclaimer, the term of this patent is extended or adjusted under 35 U.S.C. 154(b) by 0 days.

(21) Appl. No.: 18/807,866

(22) Filed: Aug. 16, 2024

(51) Int. Cl.
| | |
|---|---|
| *A61K 47/60* | (2017.01) |
| *A61K 41/00* | (2020.01) |
| *A61K 47/59* | (2017.01) |
| *A61K 47/69* | (2017.01) |
| *A61K 49/00* | (2006.01) |

(52) U.S. Cl.
CPC ...... *A61K 47/6935* (2017.08); *A61K 41/0057* (2013.01); *A61K 47/593* (2017.08); *A61K 49/0002* (2013.01)

(58) Field of Classification Search
None
See application file for complete search history.

(56) References Cited

U.S. PATENT DOCUMENTS

2010/0216804 A1\* 8/2010 Zale ............ A61K 47/60
977/773

OTHER PUBLICATIONS

Ceruti et al., J. Control. Release, 2000, vol. 63, pp. 141-153 (Year: 2000).\*

\* cited by examiner

*Primary Examiner* — Brian Gulledge
(74) *Attorney, Agent, or Firm* — Procopio, Cory, Hargreaves & Savitch LLP

(57) ABSTRACT

This disclosure relates to polyethylene glycol (PEG)-functionalized nanoparticles comprising a functional agent, and preparation methods, properties and applications thereof. The nanoparticle represented by PEG-L-G/P, comprising a type of hydrophilic PEG, a hydrophobic functional agent G, which are covalently linked by L: a linker or a chemical bond, and a type of hydrophobic polymer P. The G and P form the hydrophobic core, while the PEG constitutes the hydrophilic outer layer of the nanoparticle in an aqueous medium. The functional agent comprises one or more functional compounds including a therapeutic drug, an imaging diagnostic agent, a photoelectric responsive diagnostic agent, an immune-stimulating agent, or a combination thereof. The nanoparticles comprising such functional agent can offer various applications in multiple biomedical fields.

30 Claims, 15 Drawing Sheets

NANOPARTICLES COMPRISING A FUNCTIONAL AGENT AND METHOD OF PREPARATION AND USE THEREOF

FIELD

The present disclosure relates to the field of nano-technology, in particular, to the preparation of polyethylene glycol (PEG)-functionalized nanoparticles, and their use for drug delivery, immunization, imaging diagnostics, photodynamic therapy, and other applications.

BACKGROUND

Nanoparticles (NPs) have gained significant attention due to their extensive applications in the biomedical field, such as targeted drug delivery, imaging diagnostics, and therapeutic treatment. Particularly, nanoparticles, with their size and surface characteristics being able to controlled through chemical modification, have been recognized as beneficial in these applications, such as delivering certain drugs to a patient targeted to a specific diseased tissue but not normal tissue or controlling release of drugs. However, currently available nanoparticles encounter issues such as poor stability during drug delivery, single-drug payloads, complex diagnostics and treatments, and cumbersome preparation processes. Therefore, there is a great need for a novel nanoparticle material that can provide more stable drug loaded micelles and nanoparticles, increase drug loading efficiency, and easy to manufacture for its variety of applications.

SUMMARY

This disclosure relates to novel nanoparticles, methods of preparation, and their application in drug delivery, imaging diagnostics, photoelectric response, and immune stimulation.

Some embodiments include a nanoparticle (PEG-L-G/P) comprising: (1) an amphiphilic compound (PEG-L-G) comprising a hydrophilic polyethylene glycol (PEG) covalently linked with a hydrophobic functional agent (G) via L; and (2) a hydrophobic polymer (P); wherein L is a covalent bond or a linker comprising reactive functional groups which connects the PEG to the G via covalent bonds; wherein the G is selected from a compound having certain function, an active pharmaceutical ingredient (API) with therapeutic function, an imaging diagnostic agent, an immune-stimulating agent, a photoelectric-responsive diagnostic agent, a tumor microenvironment-responsive agent, or a combination thereof; and wherein the nanoparticle (PEG-L-G/P) has a hydrophobic core comprising the G and the P, and a hydrophilic outer layer comprising the PEG.

Some embodiments include a method for preparing the nanoparticle (PEG-L-G/P) described herein, comprising: (a) co-dissolving the PEG-L-G compound and the polymer P in one or more organic solvents to form an organic solution; (b) adding dropwise or continuously the organic solution in step a to an aqueous medium to form a mixture; (c) mixing the mixture in step b to obtain an emulsion, and optionally adding additional aqueous medium; and (d) removing the organic solvent(s) to obtain a stable nanoparticle aqueous solution (PEG-L-G/P), wherein the aqueous medium is water or phosphate-buffered solution.

Some embodiments include a lyophilized product of the nanoparticle (PEG-L-G/P) described herein, which is a powder, wherein the powder is reconstituted in water or an electrolyte aqueous solution to obtain a colloidal solution of the nanoparticle.

Some embodiments include a pharmaceutical composition comprising a nanoparticle (PEG-L-G/P) described herein, and a pharmaceutically acceptable excipient.

Some embodiments include a method of targeted delivery of a functional agent G to a mammal, comprising administering the nanoparticle (PEG-L-G/P) or the pharmaceutical composition comprising the same described herein to the target areas in a mammal.

Some embodiments include a method for treating a disease, condition or disorder; targeted diagnostics; immunotherapy; drug-immunotherapy; drug-photodynamic therapy; immunotherapy-photodynamic therapy; drug-immunotherapy-photodynamic therapy; or a combination thereof in a mammal, comprising administering a nanoparticle (PEG-L-G/P) or a pharmaceutical composition comprising the same described herein to the mammal.

Some embodiments include a method of treating a disease, condition or disorder in a mammal, comprising administering the nanoparticle (PEG-L-G/P) described herein to the mammal, wherein G is a therapeutic drug, such as anti-cancer drug.

DETAILED DESCRIPTION

Definitions

Figure 1:
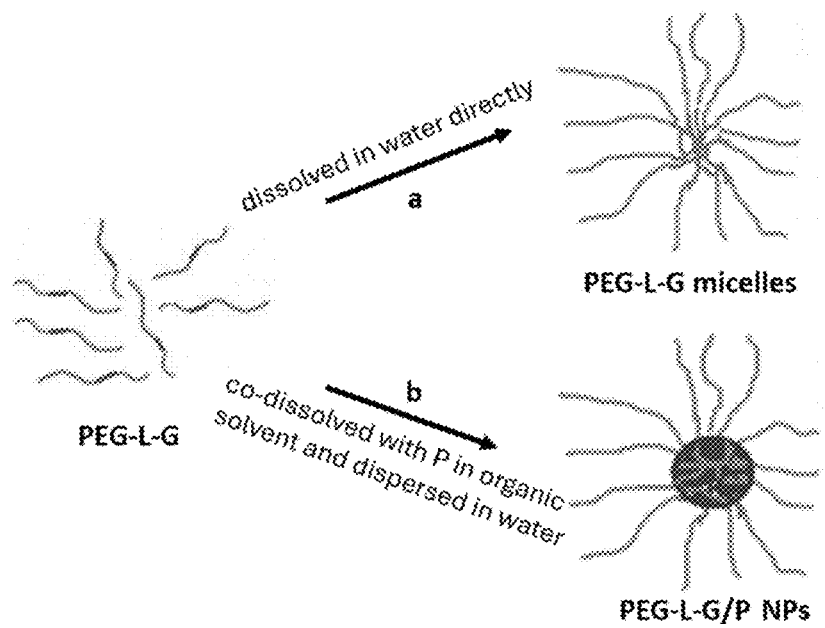
FIG. 1 depicts the self-assembly of PEG-L-G amphiphilic molecules which form (a) PEG-L-G micelles and (b) PEG-L-G/P nanoparticles in the presence of polymer P, wherein the polymer P stabilizes the PEG-L-G/P nanoparticles, in aqueous medium.

The definitions set forth in this application are intended to clarify certain terms used throughout this application.

The term "herein" means the entire application.

The section headings used herein are for organizational purpose only and are not to be construed as limiting the subject matter described.

As used herein, the term "about" means within 5% of a given value or range.

As used herein, the term "nanoparticle" refers to any particle having a diameter of less than 1000 nm, e.g., about 10 nm to about 300 nm in diameter, wherein diameter refers to the diameter of a perfect sphere having the same volume as the particle. The term "nanoparticle" is used interchangeably as "nanoparticle(s)." The term "nanoparticle" can be represented by "NP". The term "nanoparticles" can be represented by "NPs".

As used herein, the term "a nanoparticle described herein", "a nanoparticle comprising a functional agent", or "the nanoparticle" refers to a nanoparticle having a structure represented by PEG-L-G/P as defined in this disclosure.

The term "hydrophilic" described herein represents that the molecule is soluble in water or substantially soluble in water. The term "hydrophobic" represents that the molecule is not soluble in water or poorly soluble in water. The term "amphiphilic" represents that the molecule have two parts with one part soluble in water while the other part insoluble in water.

The term "a single molecular weight" described herein means that the molecular weight variation is in a range of 5-10%.

The term "pure compound" described herein means that the purity of the compound is at least 90%. The PEG described herein may comprises monomer as impurity.

The term "polydisperse" or "monodisperse" as used here refer specifically to the molecular weight distribution of PEG. These terms should not be applied to describe the size of micelles or nanoparticles.

As used herein, the term "mPEG" means that the PEG (polyethylene glycol) has a methoxy group at one free end of the PEG chain.

As used herein, the term "PEG2k" or "PEG$_{2k}$" means that the PEG (polyethylene glycol) has an average molecular weight of 2000 with a 10% of deviation, in a range of from 1800 to 2200 Daltons.

The term "PEGn" or "PEG$_n$" means that the PEG (polyethylene glycol) has n repeating units of —CH$_2$CH$_2$O—.

The term "PEG23" or "PEG$_{23}$" means that the PEG (polyethylene glycol) has 23 repeating units of —CH$_2$CH$_2$O—.

The term "PEG44" or "PEG$_{44}$" means that the PEG (polyethylene glycol) has 44 repeating units of —CH$_2$CH$_2$O—.

The term "PEG45" or "PEG$_{45}$" means that the PEG (polyethylene glycol) has 45 repeating units of —CH$_2$CH$_2$O—.

The term "PEG62" or "PEG$_{62}$" means that the PEG (polyethylene glycol) has 62 repeating units of —CH$_2$CH$_2$O—.

The term "PEG80" or "PEG$_{80}$" means that the PEG (polyethylene glycol) has 80 repeating units of —CH$_2$CH$_2$O—.

The term "PEG81" or "PEG$_{81}$" means that the PEG (polyethylene glycol) has 81 repeating units of —CH$_2$CH$_2$O—.

The Nanoparticle Comprising a Functional Agent: Structure

As mentioned above, this disclosure relates to novel polyethylene glycol (PEG)-functionalized nanoparticles, methods of preparation, and their applications.

A nanoparticle (PEG-L-G/P) comprises:
(1) an amphiphilic compound (PEG-L-G) comprising a hydrophilic polyethylene glycol (PEG) covalently linked with a hydrophobic functional agent (G) via L; and
(2) a hydrophobic polymer (P);
wherein L is a covalent bond or a linker comprising reactive functional groups which connects the PEG to the G via covalent bonds;
wherein the G is selected from a compound having certain function, an active pharmaceutical ingredient (API) with therapeutic function, an imaging diagnostic agent, an immune-stimulating agent, a photoelectric-responsive diagnostic agent, an ultrasound-responsive diagnostic agent, a tissue or an organ microenvironment-responsive diagnostic agent, a microenvironment-responsive agent, or a combination thereof; and
wherein the nanoparticle (PEG-L-G/P) has a hydrophobic core comprising the G and the P, and a hydrophilic outer layer comprising the PEG.

In the nanoparticle, a functional G, a solution or an aqueous medium is encapsulated in the nanoparticle. In an aqueous medium, the amphiphilic PEG-L-G forms a self-assembling micelle, and in the presence of the hydrophobic polymer P, the P and the hydrophobic G together forms the hydrophobic core, while the PEG forms the hydrophilic outer layer of the nanoparticle (PEG-L-G/P).

The aqueous medium may be water or phosphate-buffered saline. In some embodiments, the aqueous medium is water. In some embodiments, the aqueous medium is phosphate-buffered saline.

The novel nanoparticle (PEG-L-G/P) described herein has a typical core-shell structure in an aqueous medium or environment, such as water or phosphate-buffered saline (PBS). The PEG part in the PEG-L-G molecules form the shell, while the functional agent G in the PEG-L-G molecules and the polymer P form the core of the nanoparticle. The functional agent or compound G is generally hydrophobic and covalently linked to PEG via L to form an amphiphilic compound, which can self-assemble into micelles (PEG-L-G micelles) in an aqueous medium or environment. In the presence of the hydrophobic polymer P, these PEG-L-G molecules can be acted as emulsifiers to emulsify the hydrophobic polymer P with or without any other emulsifiers to obtain stable PEG-L-G/P nanoparticles (PEG-L-G/P) as shown in FIG. 1. The hydrophobic polymer P can interact with the hydrophobic functional agent G in the PEG-L-G molecules through intermolecular interactions, including Van der Waals force, together to form the hydrophobic core of the nanoparticle structure, while the PEG in the PEG-L-G molecules forms the hydrophilic outer layer of the nanoparticle in an aqueous medium.

The nanoparticles described herein exhibit good stability in various aqueous solutions. They have a high encapsulation efficiency of functional G agent or compound, small particle size, moderate and adjustable drug release rate, and the functional characteristics of nanoparticles.

The nanoparticles described herein exhibit excellent encapsulation efficiency for functional group G, in which PEG-L-G is used as an emulsifier to emulsify the hydrophobic polymer P and to stabilize the resulting nanoparticles with or without any other additives; in return, the polymer P not only strengthens the hydrophobic interactions with G, but also acts as an adhesive to stabilize the hydrophobic core of the nanoparticles.

The nanoparticles described herein can be directly freeze-dried in aqueous solutions and can be reconstituted into a nano-colloid with or without the addition of cryoprotectants.

The nanoparticles described herein can be lyophilized, with or without adding any additive that prevents nanoparticles from aggregation upon lyophilization, to obtain a powder, which can be redispersed in an aqueous solvent, such as water or an electrolyte aqueous solution, to obtain a colloidal solution of the nanoparticles. This lyophilization process of the nanoparticles described herein can recover both compounds of PEG-L-G and P to their original form. Because of this advantage, these novel nanoparticles comprising one or more types of functional agents can be lyophilized to a power, stored as powder, and re-used when needed by redispersing the powder in an aqueous solvent.

In the nanoparticle described herein, the PEG in PEG-L-G compound may be linear, branched, dendritic, or comb-shaped. The PEG may have a molecular weight distribution or a single molecular weight. The PEG in the nanoparticle described herein may be monodisperse PEG or polydisperse PEG (poly PEG). Monodisperse PEG is a pure compound with precise PEG units and a single molecular weight. Polydisperse PEG is a PEG mixture having a molecular weight distribution with an average molecular weight, such as 2K, 5K, 10K, etc. In some embodiments, the PEG is monodisperse PEG. In some embodiments, the PEG is polydisperse PEG.

The molecular weight of the PEG may range from about 500 to about 20,000 Daltons, about 500-1000 Daltons, about 1000-2000 Daltons, about 2000-3000 Daltons, about 3000-5000 Daltons, about 5000-7000 Daltons, about 7000-10,000 Daltons, about 10,000-15,000 Daltons, about 15,000-20,000 Daltons, about 500-600 Daltons, about 600-700 Daltons, about 700-800 Daltons, about 800-900 Daltons, about 900-1000 Daltons, about 2000 Daltons, or any molecular weight in a range bounded by, or between, any of these values.

The free end of the PEG in PEG-L-G compound may be an inert methoxy group, a reactive functional group, or a functional group. The reactive functional group refers to a group that can participate in chemical reactions, which may comprise hydroxyl, amino, carboxyl, azide, thiol, maleimide, a clickable (bioorthogonal) reactive group used in bioconjugation and click chemistry, such as azide, alkyne, cyclooctyne, tetrazine, trans-cyclooctene, norbornene, diene, dienophile, hydrazine, aldehyde/ketone, thiol, haloalkane, oxime, Isocyanate, nitrone. The functional group refers to a fluorescent group, an imaging group and/or a specific ligand fortargeted drug delivery, such as biotin, RGD peptide (Arg-Gly-Asp), an antibody, aptamer, lectin, folate, transferrin, lipid, carbohydrate (e.g., mannose, galactose), cell-penetrating peptide, homing peptide, enzyme substrate, nucleic acid probe, small molecule ligand, avidin/streptavidin, nanobody, hapten, or a DNA/RNA aptamer protein Tag (e.g., His-tag, FLAG-tag), etc. The functional group of PEG may include zwitterion, a molecule that contains both positive and negative charges at different location, such as amino acids (glycine, alanine, glutamate, lysine), betaines (glycine betaine, carnitine), phosphatidylcholine, sulfonates, taurine, creatine. The functional group of PEG may include phosphate.

The L in PEG-L-G compound connecting PEG and functional agent G, as described herein, may be a chemical bond or a linker. The chemical bond includes an environmentally responsive chemical bond or a light-responsive chemical bond. The environmentally responsive chemical bond may include, but not limited to, an ester bond, an ether bond, a carbonate bond, an amide bond, a disulfide bond, an anhydride bond, a hydrazone bond, a thioether bond, or a selenide bond. The enzyme-responsive chemical bond includes, but not limited to, a peptide bond, an ester bond, a phosphodiester bond, or glycosidic bond. The light-responsive chemical bond includes, but not limited to, a nitro-benzyl ester, a coumarin ester, or a phenacyl ester. When the L is a linker, the linker may include at least one of the chemical bonds described herein including at least one microenvironmentally responsive chemical bond in vivo. In some embodiments, L is a chemical bond, which is a cleavable bond. In some embodiments, L is a linker, which is a cleavable linker. In some embodiment, L comprises at least one chemical bond and a linker, at least one bond can be cleaved, subjecting to microenvironment change, such as pH, enzymes, temperatures, light, electric, sound wave, etc.

A hydrophobic functional agent G may be any compound having certain function. The hydrophobic functional agent G may comprise an active pharmaceutical ingredient (API) with therapeutic functions such as a drug for treating diseases, conditions, or disorders, an imaging diagnostic agent, a photodynamic compound, such as a photoelectric-responsive diagnostic agent, an immune-stimulating agent, other type of functional agent, or a combination thereof such as a combination of photoelectric-responsive diagnostic agent and a therapeutic agent. In some embodiments, the hydrophobic functional agent G may comprise an active pharmaceutical ingredient (API) with therapeutic functions. In some embodiments, the hydrophobic functional agent G may comprise a drug for treating diseases, conditions, or disorders. In some embodiments, the hydrophobic functional agent G may comprise an imaging diagnostic agent. In some embodiments, the hydrophobic functional agent G may comprise a photodynamic compound. In some embodiments, the hydrophobic functional agent G may comprise a photoelectric-responsive diagnostic agent. In some embodiments, the hydrophobic functional agent G may comprise an immune-stimulating agent. In some embodiments, the hydrophobic functional agent G may comprise a combination of multiple functional compounds. In some embodiments, the hydrophobic functional agent G may comprise a combination of photoelectric-responsive diagnostic agent and a therapeutic agent such as a drug for treating diseases, conditions, or disorder.

In some embodiments, the functional agent G described herein is an active pharmaceutical ingredient (API) with therapeutic functions, or a drug. The drug is poorly soluble in water or insoluble in water. The drug contains at least one reactive functional group. The drug may contain two or more reactive functional groups, any one of which or all of which may be linked to PEG via L. The drug may contain two reactive functional groups, either of which or both of which may be linked to PEG via L. The drug includes, but not limited to, paclitaxel and its derivative such as tricaplyl paclitaxel, doxorubicin and its derivative such as epirubicin, vinblastine, vincristine, etoposide, SN38 or its derivative, camptothecin, irinotecan, topotecan, mitomycin, tamoxifen, rapamycin, baccatin III, lamellarin D, amphotericin B, cyclophosphamide, methotrexate, wedelolactone, cisplatin, ifosfamide, or a platinum (Pt) derivative.

In some embodiments, the functional agent G described herein is a stimulator of interferon genes (STING), which can activate cancer immunotherapy. A small molecule STING include, but not limited to, MSA-2, DMXAA (Vadimezan), or NLG919.

In some embodiments, the functional agent G described herein is a luminescent molecule, which can emit fluorescence under external excitation wavelengths for tumor diagnosis. The luminescent molecule, especially the one that can emit in the near-infrared region, include, but not limited to, BODIPY, IR-26, IR-1061, IR-808, indocyanine green (ICG), cyanine dye, small molecule organic dye CH1055, D-A-D type organic small molecule, or an aggregation-induced emission (AIE) molecule, such as tetraphenylethylene (TPE).

In some embodiments, the functional agent G described herein is a photodynamic therapeutic agent, which can be selectively absorbed and activated under specific wavelengths of light, and generates reactive oxygen species (ROS) to kill cancer cells. The photodynamic therapeutic agent may include, but not limited to, porphyrin, phthalocyanine, chlorin, texaphyrin, phenothiazinium, rose bengal, indocyanine green (ICG), or hypericin.

In some embodiments, the functional agent G described herein may comprise a single type of drug or a combination of two or more types of drugs, achieving a synergistic therapeutic effect. In some embodiments, the functional agent G described herein may comprise a combination of a therapeutic drug and an immune-stimulating compound. In some embodiments, the functional agent G described herein may comprise a combination of a therapeutic drug and a luminescent compound. In some embodiments, the functional agent G described herein may comprise a combination of a therapeutic drug and a photodynamic therapeutic agent. In some embodiments, the functional agent G described herein may comprise any combination of two or more therapeutic drugs, immune-stimulating compounds, luminescent compounds, and/or photodynamic therapeutic agents.

The polymer P described herein is a hydrophobic polymer which can be degraded by external stimuli. The polymer P is not water soluble and is soluble in an organic solvent. P is preferably used in the biomedical field The polymer P may include, but not limited to, polyester or its derivative such as polylactic acid (PLA), polycaprolactone (PCL), polyhydroxyalkanoates (PHA), polyhydroxybutyrate (PHB), polyhydroxyvalerate (PHV), or polyglycolic acid (PGA); polycarbonate or its derivative such as poly(trimethylene carbonate); polydioxanone or its derivative; polyanhydride; or a combination thereof in a copolymer, such as poly(lactic acid)-polytrimethylene carbonate copolymer or its derivative.

In some embodiments, the polymer P described herein is polyester or its derivative. In some embodiments, the polymer P described herein is polylactic acid (PLA), also known as poly(lactic acid). In some embodiments, the polymer P described herein is polycaprolactone (PCL). In some embodiments, the polymer P described herein is polyhydroxyalkanoates (PHA). In some embodiments, the polymer P described herein is polyhydroxybutyrate (PHB). In some embodiments, the polymer P described herein is polyhydroxyvalerate (PHV). In some embodiments, the polymer P described herein is or polyglycolic acid (PGA). In some embodiments, the polymer P described herein is polycarbonate or its derivative. In some embodiments, the polymer P described herein is poly(trimethylene carbonate). In some embodiments, the polymer P described herein is polydioxanone or its derivative. In some embodiments, the polymer P described herein is polyanhydride. In some embodiments, the polymer P described herein is a copolymer comprising any two or more of the polymers described herein. In some embodiments, the polymer P described herein is poly(lactic acid)-polytrimethylene carbonate copolymer or its derivative.

The molecular weight of the polymer P may vary. The molecular weight of the polymer P may be about 500-1,000K (or 500-1,000,000) Dalton. In some embodiments, the polymer P is polylacetic acid (PLA). The molecular weight of the PLA may be about 500-100K Dalton, about 500-1000 (or 1 k) Dalton, about 1 k-5 k Dalton, about 5-10 K Dalton, about 10 K-20 K Dalton, about 20 K-30 K Dalton, about 30 K-40 K Dalton, about 40 k-60 k Dalton, about 40 K Dalton, about 50 k Dalton, about 60 K Dalton, or any molecular weight in a range bounded by, or between, any of these values Peg-L-G Compounds:

The PEG in the PEG-L-G compound may be monodisperse PEG or polydisperse PEG. In some embodiments, the PEG in the PEG-L-G compound is monodisperse PEG. In some embodiments, the PEG in the PEG-L-G compound is polydisperse PEG.

The PEG-L-G compound can be synthesized via a reaction of a PEG having a reactive end group with a functional agent G. For example, when the G is Paclitaxel (PTX), and the PEG is a mPEG with an end methoxy group at one end and a —CH$_2$COOH group or other carboxylic acid at the other end, the carboxylic acid group of the mPEG can react with an —OH group of PTX in the presence of a coupling agent, such as EDCI and a catalytic amounts of 4-(dimethylamino)pyridine (DMAP) to form an ester bond resulting in e.g. mPEGn-CH$_2$COO-PTX as shown in Scheme 1, where n represents the number of units of —OCH$_2$CH$_2$— in the mPEG. In this case, PEG and G are covalently linked via —CH$_2$COO—.

Scheme 1: Esterification reaction of mPEGn-acetic acid with paclitaxel to obtain mPEGn-CH$_2$COO-PTX.

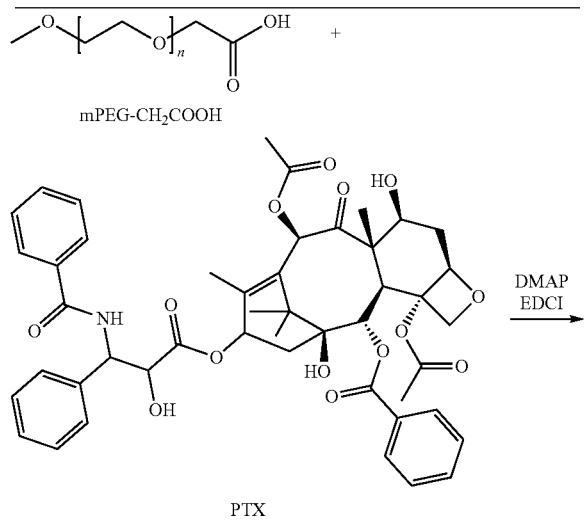

mPEG-CH$_2$COOH

PTX mPEGn-CH$_2$COO-PTX

Paclitaxel (PTX) is a chemotherapy medication used to treat ovarian cancer, esophageal cancer, breast cancer, lung cancer, Kaposi's sarcoma, cervical cancer, and pancreatic cancer. The pegylated prodrug mPEGn-CH$_2$COO-PTX comprising Paclitaxel can be easily prepared via esterification.

The PEG and G can also be covalently linked via a carbonate bond. For example, mPEGn-OCO-PTX can be synthesized from mPEG with an end —OH group being activated by a leaving group and Paclitaxel (PTX) as shown in Scheme 2. In this case, PEG and G are covalently linked via a carbonate bond (—OCO—).

Scheme 2. Synthesis of mPEGn-OCO-PTX carbonate

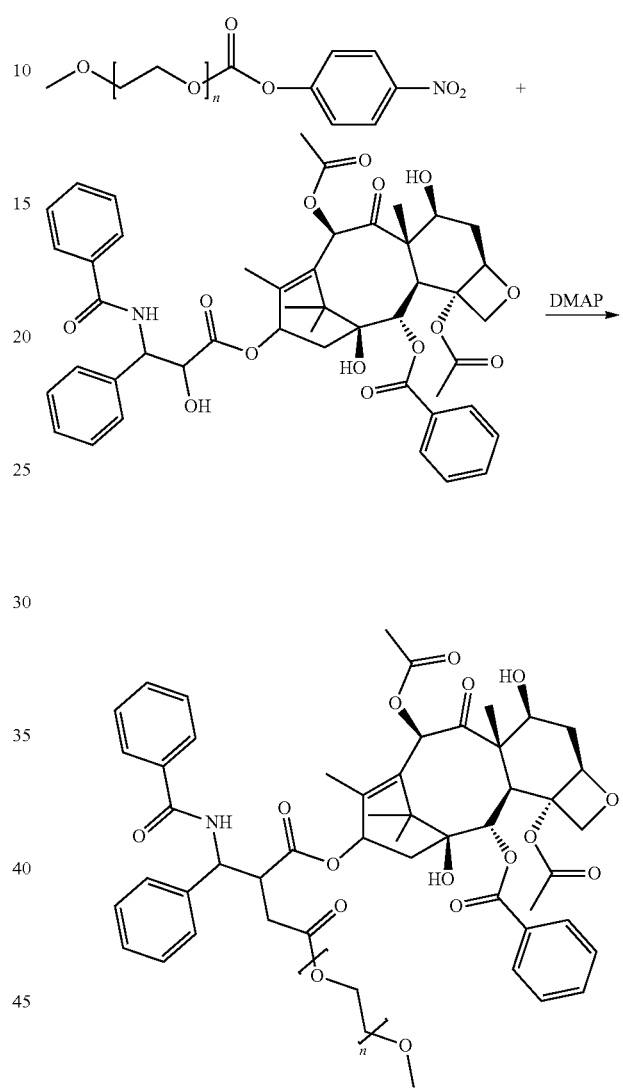

In some embodiments, the PEG and G are linked via a linker. In some embodiments, a linker can be first linked to the PEG to form PEG-L, which can be further linked to the functional agent G via a chemical bond, such as an ester bond. For example, mPEG$_{2k}$-CONHCH$_2$CH$_2$—SS—CH$_2$CH$_2$COO—SN38 can be synthesized as shown in Scheme 3. In this case, PEG and G are covalently linked via a linker to form PEG-L-G.

Scheme 3. Synthesis of mPEGn-CH$_2$COHN-SS-CH$_2$CH$_2$COO-SN38

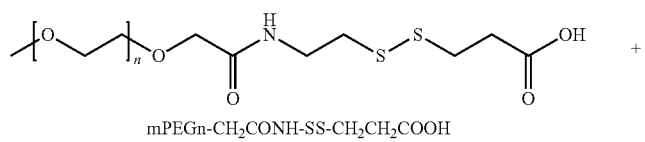

mPEGn-CH$_2$CONH-SS-CH$_2$CH$_2$COOH

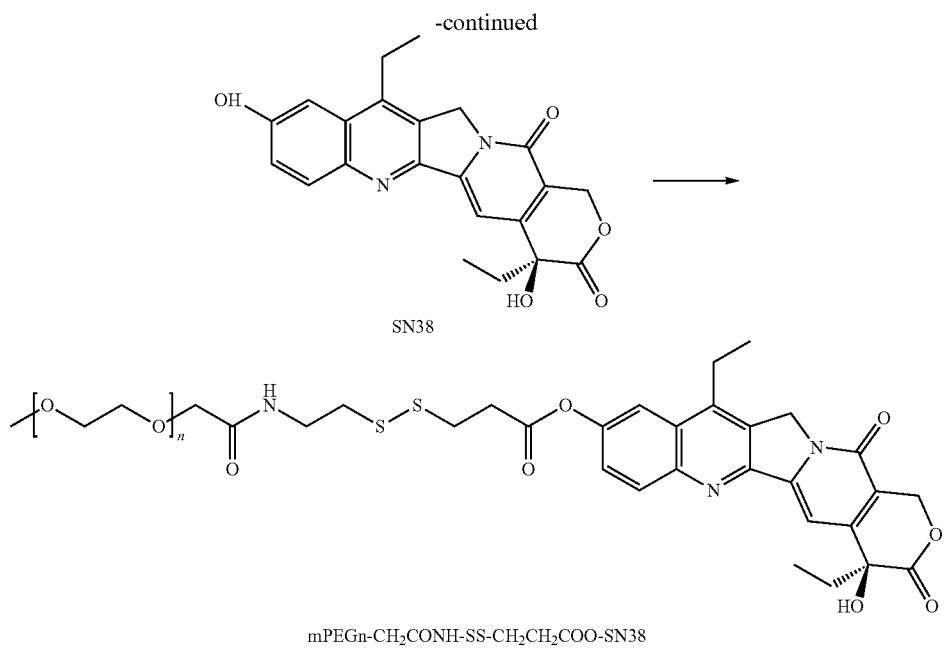

mPEGn-CH₂CONH-SS-CH₂CH₂COO-SN38

SN-38 is an antineoplastic drug. It is the active metabolite of irinotecan but has 1000 times more activity than irinotecan itself. SN-38 is a form of the anticancer drug irinotecan. SN-38 liposome is being studied in the treatment of advanced colorectal cancer and other types of cancer. The tumor microenvironment is usually reductive, and tumor cells produce high levels of reductive molecules, such as glutathione (GSH). By utilizing the reduction response of disulfide bonds in the GSH environment, these bonds can be cleaved in specific environments to release anticancer drugs, such as SN-38, reducing side effects on normal tissues and achieving targeted drug delivery. As shown in Scheme 3, the pegylated prodrug mPEGn-CONH—SS—COO—SN38 comprising SN38 and disulfide bond (—SS—) can be easily synthesized via esterification.

In some embodiments, the PEG-L-G compound comprises a branched PEG. In some embodiments, two PEG molecules can be covalently linked to a linker first, such as Lysine, via chemical bonds, such as amide bonds. The carboxylic acid group of the Lysine can further react with a drug such as PTX via esterification in the presence of EDC and a catalytic amount of DMAP to form a PEG-L-G compound comprising a branched PEG. For example, the synthesis of monodisperse mPEG$_{23x2}$-Lysine-PTX is shown in Scheme 4. In this case, PEG and G are covalently linked via a linker to form PEG-L-G.

Scheme 4. Synthesis of Monodisperse mPEG$_{23x2}$-Lysine-PTX

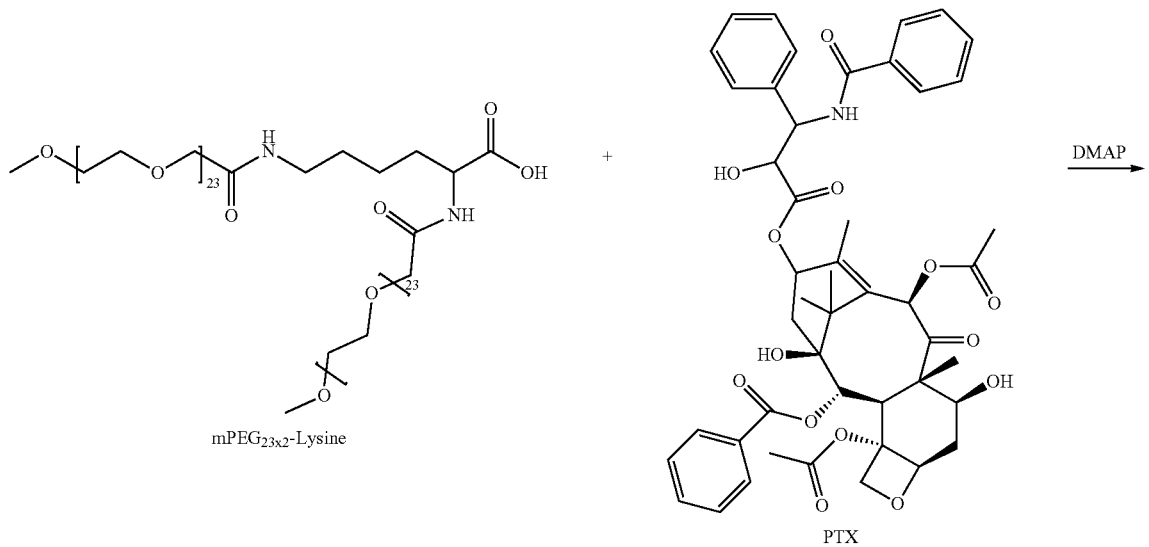

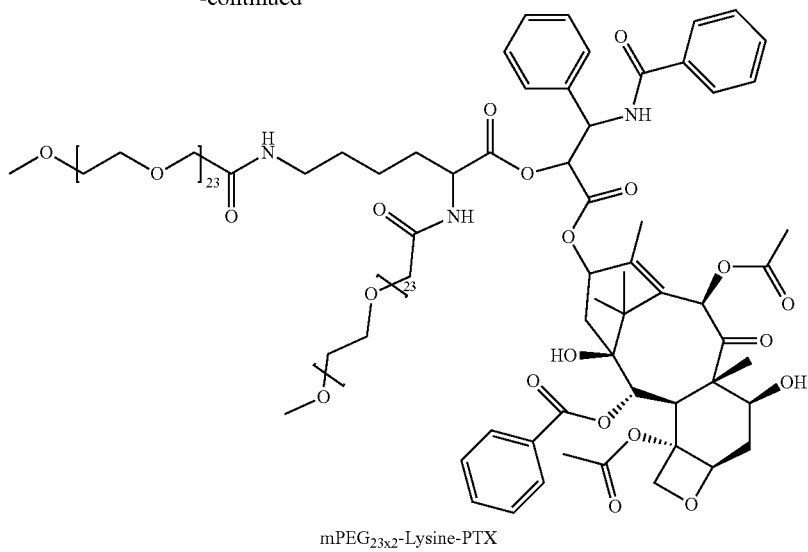

mPEG₂₃ₓ₂-Lysine-PTX

Other PEG-L-G compounds can be made similarly. For example, the following PEG-L-G compounds can be made using the same or similar methods.

In some embodiments, the PEG can be linked to a function agent G via an amide bond. For example, polydisperse mPEG$_{2k}$-CH$_2$CONH-tetraphenyl ethylene (TPE) can be synthesized according to Scheme 5.

Scheme 5. Synthesis of mPEG-CH$_2$-CONH-TPE

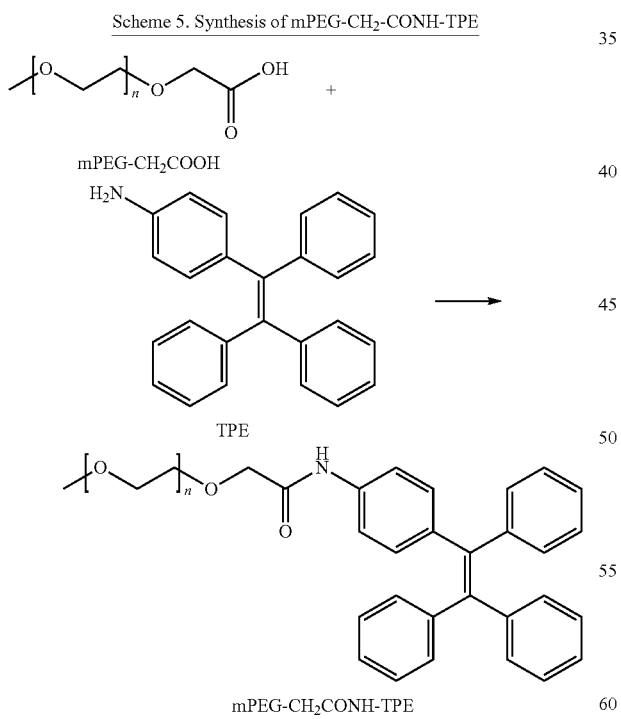

mPEG-CH$_2$CONH-TPE

Tetraphenyl ethylene (TPE) exhibits aggregation-induced emission characteristics, which does not emit light in solution but emits green or sky-blue fluorescence when in an aggregated state. Other Pegylated imaging diagnostic agent can be made similarly.

Similarly, the Pegylated prodrug mPEG$_{2k}$-O(O=C)-MSA-2 can also be synthesized via esterification as shown in Scheme 6. Coupling reagent DCC or EDC can be used for the formation of an ester bond between the hydroxy group of the mPEG$_{2k}$-OH and the carboxylic acid group of MSA-2. MSA-2 is an orally available non-nucleotide human STING (Stimulator of Interferon Genes) agonist with antitumor activity.

Scheme 6. Synthesis of mPEGn-O(O=C)-MSA-2

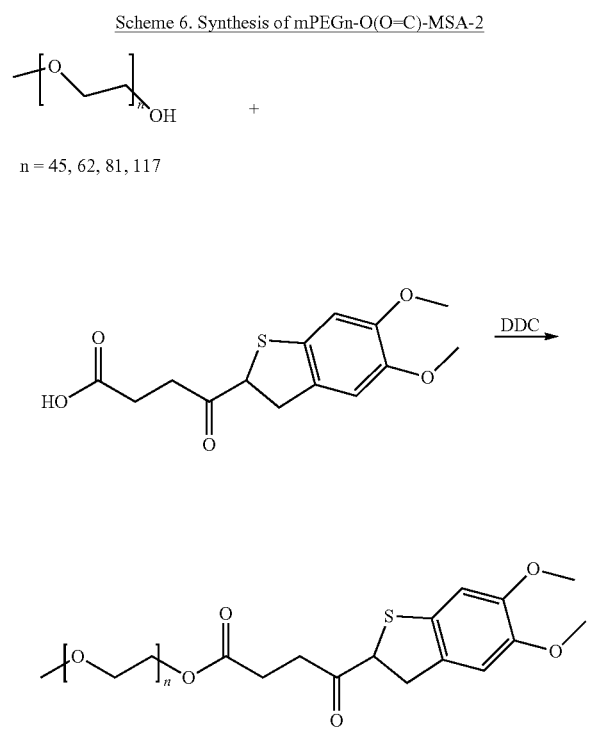

n = 45, 62, 81, 117

Similarly, the Pegylated prodrug mPEG$_{44}$-CH$_2$CONH—CH$_2$CH$_2$—SS—CH$_2$CH$_2$O(O=C)-MSA-2 can also be synthesized via esterification, in which an environment responsive disulfide bond is introduced, as shown in Scheme 7.

Scheme 7. Synthesis of mPEG$_{44}$-CH$_2$CONH-CH$_2$CH$_2$-SS-CH$_2$CH$_2$O(O=C)-MSA-2.

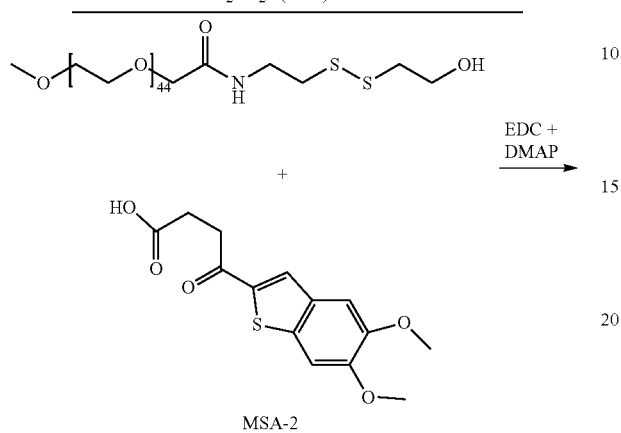

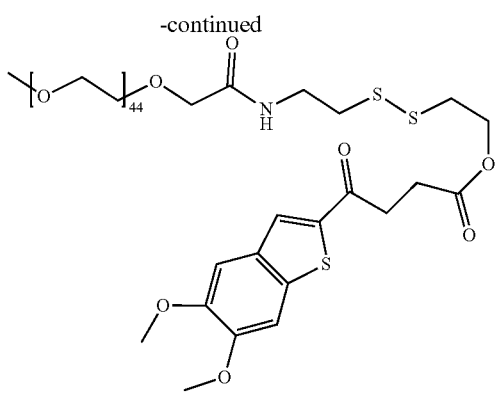

Similarly, the Pegylated prodrug containing two MSA-2 molecules, mPEG$_{44}$-CH$_2$CONH—CH$_2$CH$_2$—SS-di-MSA-2 esters, can also be synthesized via esterification as shown in Scheme 8:

Scheme 8. Synthesis of mPEG$_{44}$-CH$_2$CONH-CH$_2$CH$_2$-SS-di-MSA-2 esters

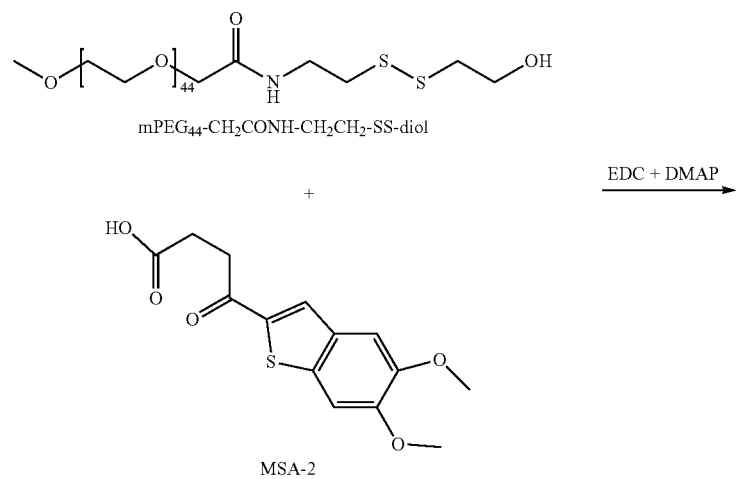

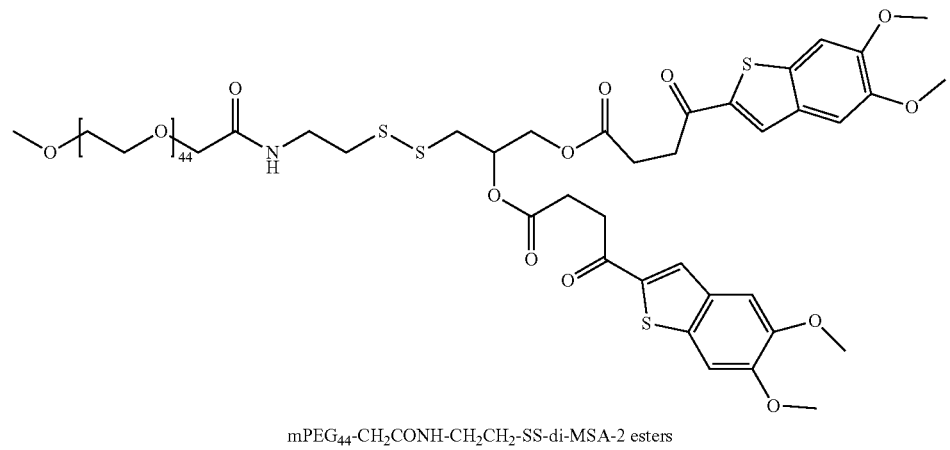

mPEG$_{44}$-CH$_2$CONH-CH$_2$CH$_2$-SS-di-MSA-2 esters

The Pegylated prodrug, mPEG$_{44}$-succinate-NLG-919 esters, can also be synthesized via esterification as shown in Scheme 9. NLG-919 (IDO-IN-7) is a chemical compound known as an indoleamine 2,3-dioxygenase 1 (IDO1) inhibitor. IDO1 is an enzyme that plays a key role in the metabolism of tryptophan, leading to the production of kynurenine. This metabolic pathway is often exploited by cancer cells to suppress the immune response, particularly by promoting an immunosuppressive environment. By inhibiting IDO1, compounds like NLG-919 can potentially restore immune function and enhance the efficacy of other cancer therapies, making them a subject of interest in oncology research.

Scheme 9. Synthesis of mPEG$_{44}$-succinate-NLG-919 (IDO-IN-7).

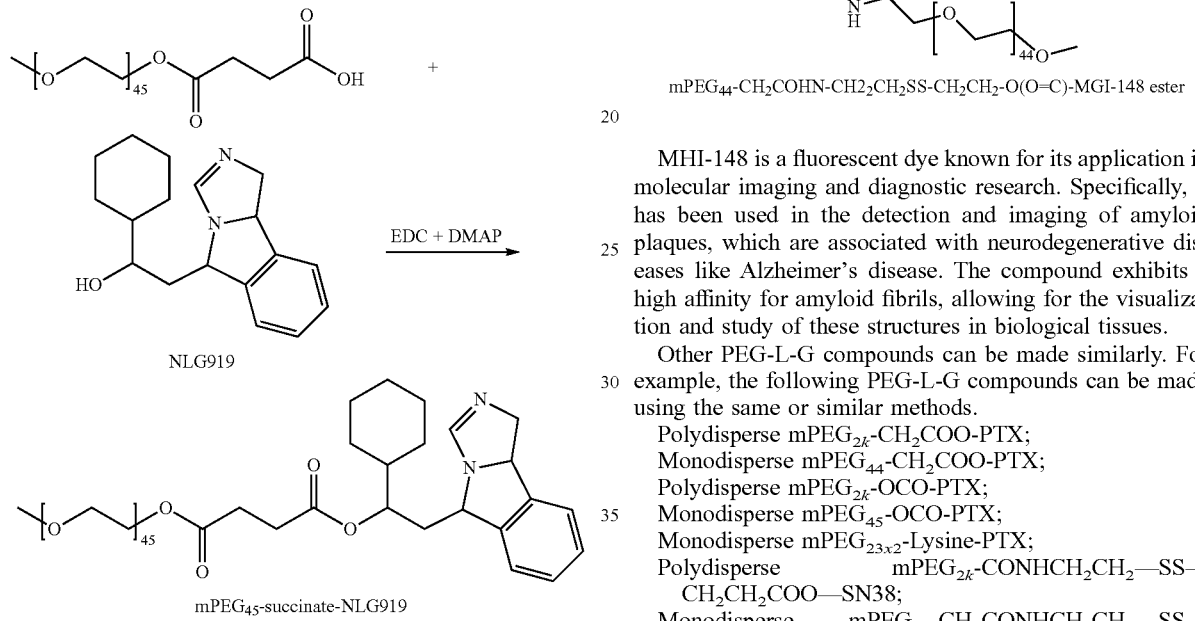

The Pegylated dye of mPEG$_{44}$-CONH—CH$_2$CH$_2$SS—CH$_2$CH$_2$O(O═C)-MHI-148a can also be synthesized via esterification as shown in Scheme 10:

Scheme 10. Synthesis of mPEG$_{44}$-CONH-CH$_2$CH$_2$SS-CH$_2$CH$_2$O(O═C)-MHI-148 ester.

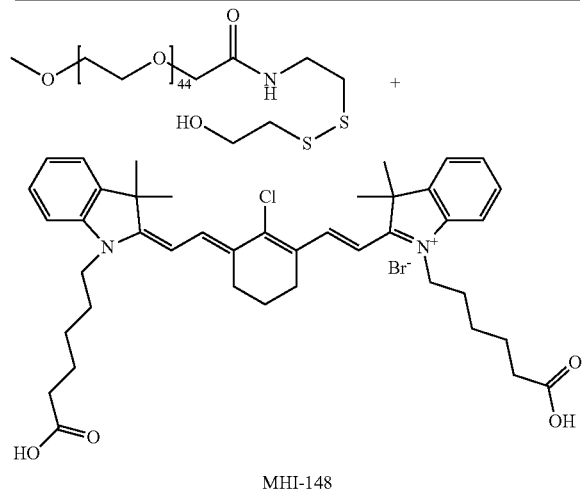

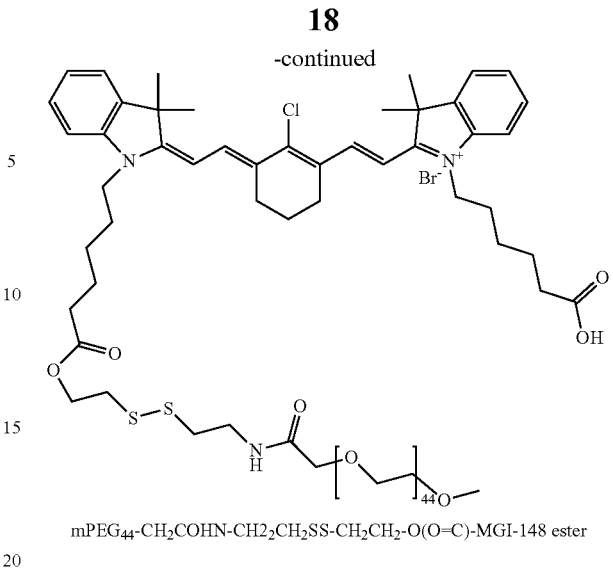

mPEG$_{44}$-CH$_2$COHN-CH$_2$$_2$CH$_2$SS-CH$_2$CH$_2$-O(O═C)-MGI-148 ester

MHI-148 is a fluorescent dye known for its application in molecular imaging and diagnostic research. Specifically, it has been used in the detection and imaging of amyloid plaques, which are associated with neurodegenerative diseases like Alzheimer's disease. The compound exhibits a high affinity for amyloid fibrils, allowing for the visualization and study of these structures in biological tissues.

Other PEG-L-G compounds can be made similarly. For example, the following PEG-L-G compounds can be made using the same or similar methods.

Polydisperse mPEG$_{2k}$-CH$_2$COO-PTX;
Monodisperse mPEG$_{44}$-CH$_2$COO-PTX;
Polydisperse mPEG$_{2k}$-OCO-PTX;
Monodisperse mPEG$_{45}$-OCO-PTX;
Monodisperse mPEG$_{23x2}$-Lysine-PTX;
Polydisperse mPEG$_{2k}$-CONHCH$_2$CH$_2$—SS—CH$_2$CH$_2$COO—SN38;
Monodisperse mPEG$_{44}$-CH$_2$CONHCH$_2$CH$_2$—SS—CH$_2$CH$_2$COO—SN38;
Polydisperse mPEG$_{2k}$-CH$_2$CONH-tetraphenyl ethylene (TPE);
Monodisperse mPEG$_{45}$-O(O═C)-MSA-2;
Monodisperse mPEG$_{62}$-O(O═C)-MSA-2;
Monodisperse mPEG$_{81}$-O(O═C)-MSA-2;
Polydisperse mPEG$_{2k}$-O(O═C)-MSA-2;
Monodisperse mPEG$_{44}$-CH$_2$CONH—CH$_2$CH$_2$—SS—CH$_2$CH$_2$O(O═C)-MSA-2;
Monodisperse mPEG$_{44}$-CH$_2$CONH—CH$_2$CH$_2$—SS-di-MSA-2 esters;
Monodisperse mPEG$_{44}$-succinate-NLG-919 (IDO-IN-7); or
Monodisperse mPEG$_{44}$-CH$_2$CONH—CH$_2$CH$_2$SS—CH$_2$CH$_2$O(O═C)-MHI-148 ester.

PEG-L-G Micelles

A micelle is an aggregate (or supramolecular assembly) of surfactant amphiphilic molecules dispersed in an aqueous solution or an aqueous medium, forming a colloidal suspension (also known as associated colloidal system). A typical micelle in water forms an aggregate with the hydrophilic "head" regions in contact with surrounding aqueous medium, sequestering the hydrophobic single-tail regions in the micelle center.

Micelles are approximately spherical in shape. Other shapes, such as ellipsoids, cylinders, and bilayers, are also possible. The shape and size of a micelle are a function of the molecular geometry of its surfactant molecules and solution conditions such as surfactant concentration, temperature, pH, and ionic strength. The process of forming micelles is known as micellization.

As the PEG in PEG-L-G is hydrophilic, while the functional agent G is hydrophobic, the PEG-L-G is amphiphilic. The PEG-L-G molecule has two parts with one part soluble in water while the other part insoluble in water. In the presence of an aqueous medium or environment, such as water or phosphate-buffered saline (PBS), the amphiphilic PEG-L-G molecules can self-assemble into micelles (FIG. 1). For example, the PEG-L-G compounds described herein can from micelles, such as spherical micelles, in an aqueous medium, such as PBS buffer at pH of solution, at pH of 7.4, 5.0, or 5.0-7.4, at a suitable temperature, such as 0° C., room temperature, or from 0° C. to room temperature. In the spherical micelles, the PEG in the PEG-L-G forms the hydrophilic "head" regions in contact with surrounding aqueous solution or aqueous medium, and the hydrophobic G in the PEG-L-G forms the hydrophobic region in the micelle center.

The size of a PEG-L-G micelle described herein may range about 30-200 nm, about 50-100 nm, about 30-50 nm, about 50-70 nm, about 70-90 nm, about 90-100 nm, about 100-110 nm, about 110-120 nm, about 120-125 nm, about 119-120 nm, about 120 nm, about 121-122 nm, about 122 nm, about 75-76 nm, about 76 nm, or any size in a range bounded by, or between, any of these values.

Nanoparticles PEG-L-G/P:

The preparation of the PEG functionalized nanoparticles (PEG-L-G/P) described herein may be achieved using the emulsion solvent evaporation method. In some embodiments, the nanoparticles (PEG-L-G/P) described herein can be prepared by the following steps:
  (a) co-dissolving the PEG-L-G compound and the polymer P in one or more organic solvents to form an organic solution;
  (b) adding dropwise or continuously the organic solution in step a to an aqueous medium to form a mixture;
  (c) mixing the mixture in step b to obtain an emulsion, and optionally adding additional aqueous medium; and
  (d) removing the organic solvent(s) by evaporation or by dialysis, to obtain a stable nanoparticle aqueous solution (PEG-L-G/P),
  wherein the aqueous medium is water or phosphate-buffered solution.

The organic solvents used in the preparation of the nanoparticles described herein may comprise low-boiling point solvents or high-boiling point solvents that are miscible or partially miscible with water. The low-boiling point organic solvents may include dichloromethane, ethyl acetate, tetrahydrofuran, acetone, ethanol, acetonitrile, or a combination thereof. The high-boiling point organic solvents may comprise dimethylformamide (DMF), dimethyl sulfoxide (DMSO), or a combination thereof. Preferably, organic solvents with low-boiling point that are miscible or partially miscible with water may be used.

The following nanoparticles (PEG-L-G/P) can be made similarly.
  Polydisperse mPEG$_{2k}$-CH$_2$COO-PTX/PLA Nanoparticles;
  Monodisperse mPEG$_{44}$-CH$_2$COO-PTX/PLA Nanoparticles;
  Polydisperse mPEG$_{2k}$-OCO-PTX/PLA Nanoparticles;
  Monodisperse mPEG$_{45}$-OCO-PTX/PLA Nanoparticles;
  Monodisperse mPEG$_{23\times2}$-Lysine-PTX/PLA Nanoparticles;
  Polydisperse mPEG$_{2k}$-CH$_2$CONHCH$_2$CH$_2$—SS—CH$_2$CH$_2$COO—SN38/PLA Nanoparticles;
  Monodisperse mPEG$_{44}$-CH$_2$CONHCH$_2$CH$_2$—SS—CH$_2$CH$_2$COO—SN38/PLA Nanoparticles;
  Polydisperse mPEG$_{2k}$-CH$_2$CONH-TPE/PLA Luminescent Nanoparticles;
  Monodisperse mPEG$_{45}$-O(O=C)-MSA-2/PLA Nanoparticles;
  Monodisperse mPEG$_{62}$-O(O=C)-MSA-2/PLA Nanoparticles;
  Monodisperse mPEG$_{81}$-O(O=C)-MSA-2/PLA Nanoparticles;
  Polydisperse mPEG$_{2k}$-O(O=C)-MSA-2/PLA Nanoparticles;
  Monodisperse mPEG$_{44}$-CH$_2$CONH—CH$_2$CH$_2$—SS—CH$_2$CH$_2$O(O=C)-MSA-2/PLA Nanoparticles;
  Monodisperse mPEG$_{44}$-CH$_2$CONH—CH$_2$CH$_2$—SS-di-MSA-2/PLA Nanoparticles;
  Monodisperse mPEG$_{44}$-succinate-NLG-919 (IDO-IN-7)/PLA Nanoparticles; or
  Monodisperse mPEG$_{44}$-CH$_2$CONH—CH$_2$CH$_2$SS—CH$_2$CH$_2$O(O=C)-MHI-148/PLA Nanoparticles.

Dual-Component Nanoparticle: Preparation and Property

A dual-component nanoparticles may be prepared by first mixing two different types of PEG-L-G, such as having different G with different functions, then using the same method described herein for preparing nanoparticles. In some embodiments, the same weight of two different types of PEG-L-G may be used to prepare the nanoparticles. In some embodiments, the same type of the polymer P may be used. For example, the following dual-component nanoparticles can be prepared this way.
  (mPEG$_{80}$-CH$_2$COO-PTX and mPEG$_{80}$CH$_2$CONH—SS—CH$_2$CH$_2$COO—SN38)/PLA Nanoparticle;
  (mPEG$_{80}$-CH$_2$COO-PTX and mPEG$_{81}$-O(O=C)-MSA-2)/PLA Nanoparticle; or
  (mPEG$_{80}$-CH$_2$CONH—SS—CH$_2$CH$_2$COO—SN38 and mPEG$_{81}$-O(O=C)-MSA-2)/PLA Nanoparticle.

The nanoparticle PEG-L-G/P described herein may have the mass ratio of PEG-L-G to polymer P in the nanoparticles of about 1:1 to about 20:1 (or about 1-20), about 1:1-2:1 (or about 1-2), about 1:1-3:1, about 1:1-4:1, about 1:1-5:1, about 1:1-6:1; about 1:1-7:1, about 1:1-8:1, or 1:1-9:1, about 1:1-10:1, about 1:1-12:1, about 1:1-13:1, about 1:1-14:1, about 1:1-15:1, about 1:1-16:1, about 1:1-17:1, about 1:1-18:1, about 1:1-19:1, about 1:1-20:1, about 1-5, about 5-10, about 10-15, about 15-20, about 2-5, about 5-7, about 7-10, about 10-13, about 13-16, about 16-20, or any mass ratio in a range bounded by, or between, any of these values.

The particle size of the nanoparticle PEG-L-G/P described herein may be between 1 and 200 nanometers (nm) in diameter, about 10-200 nm, about 50-200 nm, about 100-200 nm, about 50-150 nm, about 70-125 nm, about 50-170 nm, about 70-170 nm, about 70-130 nm, about 90-130 nm, about 100-130 nm, about 30 to about 200 nm, about 30-50 nm, about 50-60 nm, about 60-70 nm, about 70-80 nm, about 80-90 nm, about 70-90 nm, about 50-100 nm, about 70-100 nm, about 90-100 nm, about 100-110 nm, about 105-110 nm, about 110-115 nm, about 110-120 nm, about 120-125 nm, about 110-130 nm, about 130-150 nm, about 150-170 nm, about 170-200 nm, about 106-107 nm, about 106 nm, about 111-112 nm, about 111 nm, about 119-120 nm, about 120 nm, about 121-122 nm, about 122 nm, or any size in a range bounded by, or between, any of these values.

The dispersity of polyethylene glycol may not significantly affect the particle size of the PEG-L-G micelles or the PEG-L-G/P nanoparticles described here. The particle size of a PEG-L-G/P nanoparticle may decrease as compared to the particle size of its corresponding PEG-L-G micelle, wherein the PEG-L-G molecule is same. The core of a PEG-L-G/P nanoparticle may be more compact than its corresponding PEG-L-G micelle.

Stability In phosphate-buffered saline (PBS) (pH=7.4), the PEG-L-G micelle wherein L is —CH$_2$COO—, such as mPEGn-CH$_2$COO-PTX micelle, may have poor stability based on the measured particle size. The size of the micelle may significantly increase in less than 1 hour, about 1-2 hours, or in 2 hours in PBS. The stability of a PEG-L-G/P nanoparticle (NP) may increase as compared with the corresponding PEG-L-G micelle in PBS. A monodisperse PEG may improve the stability of the PEG-L-G/P nanoparticle, such as mPEGn-CH$_2$COO-PTX/PLA nanoparticle, as compared with a polydisperse PEG, such as mPEG-CH$_2$COO-PTX/PLA nanoparticle. The polymer P, such as PLA may significantly enhance the stability of PEG-L-G/P nanoparticle, such as mPEG$_n$-CH$_2$COO-PTX/PLA nanoparticle in PBS at pH 7.4 and 37° C.

In PBS (pH=7.4), the mPEG-OCO-G/P nanoparticle, such as mPEGn-OCO-PTX/PLA nanoparticle, may have good stability, which is superior to a mPEG-CH$_2$COO-G/P nanoparticle, such as mPEGn-CH$_2$COO-PTX/PLA nanoparticles in PBS. The particle size of a mPEG-CH$_2$COO-G/P nanoparticle, such as a mPEG$_n$-CH$_2$COO-PTX/PLA nanoparticle, particularly when the PEG is monodispersed PEG, may not increase or may increase not significantly in about 1-2 hours, about 2-3 hours, about 2-4 hours, about 4-8 hours, about 8-12 hours, about 12 hours, or longer. The particle size of the PEG-OCO-G/P nanoparticle, such as a mPEGn-OCO-PTX/PLA nanoparticle, may not increase in about 24 hours, about 24-48 hours, about 48 hours, about 48-72 hours, about 72 hours, about 72-96 hours, about 96 hours, about 96-120 hours, about 120 hours, about 144 hours, about 144-168 hours, about 168 hours, about 1 day, about 1-2 days, about 2 days, about 2-3 days, about 3 days, about 3-4 days, about 4 days, about 4-5 days, about 5 days, about 5-6 days, about 6 days, about 6-7 days, about 7 days, or longer in PBS solution at pH 7.4 and 37° C.

In Bovine Serum Albumin (BSA) pure water solution, the PEG-L-G micelle wherein L is —CH$_2$COO—, such as mPEGn-CH$_2$COO-PTX micelle, may have poor stability. The size of the micelle may increase in less than about 2 hours, about 2-3 hours, about 3-4 hours, about 4-6 hours, or about 6-8 hours in BSA solution at 37° C. The size of the micelle may increase rapidly after about 8 hours, about 9 hours, or about 10 hours in BSA solution at 37° C. The size of the micelle may increase about 2 times, 2-3 times, about 3 times, about 5 times, about 3-5 times, about 5-8 times, or about 8 times after 12 hours in BSA solution at 37° C. The PEG-L-G/P nanoparticle, such as mPEGn-CH$_2$COO-PTX/PLA nanoparticle, may be more stable than its corresponding PEG-L-G micelle in BSA. The size of the nanoparticle may increase after about 2 hours, about 3 hours, about 3-4 hours, about 4-6 hours, or about 6-8 hours in BSA pure water solution at 37° C. The size of the nanoparticle may increase slower than the corresponding micelle. The size of the nanoparticle may increase less than 2 times, about 1-2 times, about 1.5 times, about 2-3 times, about 3-4 times, about 4-6 times, or about 5 times after 12 hours in BSA pure water solution at 37° C. A monodisperse PEG-L-G/P nanoparticle may have better stability than a polydisperse PEG-L-G/P nanoparticle. For example, the particle size of a monodisperse PEG-L-G/P nanoparticle, such as monodisperse mPEGn-CH$_2$COO-PTX/PLA nanoparticle, may only have a slight change after about 10 hours, about 12 hours, about 12-14 hours, 14-16 hours, 16-20 hours, or 20-24 hours in PBS solution at 37° C.

In a BSA or PBS solution, the PEG-OCO-G/P nanoparticle, such as mPEGn-OCO-PTX/PLA nanoparticle, may have good stability, which may be superior to a PEG-CH$_2$COO-G/P nanoparticle, such as mPEGn-CH$_2$COO-PTX/PLA nanoparticles in PBS. The particle size of a polydisperse PEG-OCO-G/P nanoparticle, such as polydisperse mPEGn-OCO-PTX/PLA nanoparticle, may increase after at least 24 hours, at least 48 hours, at least about 72 hours, about 24-48 hours, about 48-72 hours, about 72 hours, about 84 hours, about 72-84 hours, about 84-96 hours, about 96 hours, at least about 1 day, about 1-2 days, at least about 2 days, about 2-3 days, at least about 3 days, about 3-4 days, about 4 days, or longer in BSA solution at 37° C. A monodisperse PEG-L-G/P nanoparticle may have better stability than a polydisperse PEG-L-G/P nanoparticle. For example, the particle size of a monodisperse PEG-L-G/P nanoparticle, such as monodisperse mPEGn-OCO-PTX/PLA nanoparticle, may not have any particle size change after at least about 72 hours, about 96 hours, about 72-96 hours, about 108 hours, about 120 hours, about 96-120 hours, about 132 hours, about 120-144 hours, about 144 hours, about 96-144 hours, about 156 hours, about 144-168 hours, about 168 hours, or about 96-168 hours, at least about 3 days, at least 7 days, about 3-4 days, about 4-5 days, about 5-6 days, about 6-7 days, or longer in BSA solution at 37° C.

Release of Functional Agent G

In vitro release of the functional agent G from a PEG-L-G micelle or a PEG-L-G/P nanoparticle described herein, such as mPEGn-CH$_2$COO-PTX micelle or mPEGn-CH$_2$COO-PTX/PLA nanoparticle wherein the average MW is 2k (or 2000) or the repeat unit n is 45, in PBS buffer solution at 37° C. with stirring, may have same release pattern, based on the detected PTX amount by HPLC. The functional agent G, such as PTX, may be released from the nanoparticle slower than from the corresponding micelle, preliminary due to the increased stability provided by the polymer P, such as PLA, in the nanoparticle. The functional agent G may be released from the micelle about 10-15%, about 15-20%, about 20%, about 20-25%, about 25%, or about 25-30% in 1 hour. The nanoparticle may not have burst release in about 1 hour, about 1-2 hour, about 2-4 hours, about 4-5 hours, or longer. About 50% of the functional agent G may be released from the micelles after about 12-24 hours, about 18 hours, or longer. About 50% of the functional agent G may be released from the nanoparticles after about 24-36 hours, about 30 hours, about 30-55 hours, about 31 hours, or longer. About 80% of the functional agent G may be released from the micelles after about 84-96 hours, about 89 hours, about 96 hours, or longer. About 80% of the functional agent G may be released from the nanoparticles after about 108-120 hours, about 112 hours, about 120-144 hours, about 132 hours, or longer.

Pharmacokinetics

A monodisperse PEG-L-G micelle may have longer half-life ($t_{1/2}$) than a polydisperse PEG-L-G micelle in mice. A monodisperse PEG-L-G/P nanoparticle may have longer half-life ($t_{1/2}$) than a polydisperse PEG-L-G/L nanoparticle in mice. A PEG-L-G/P nanoparticle comprising a branched PEG may have the longest half-life ($t_{1/2}$) in mice. In some embodiments, a PEG-L-G micelle described herein may have half-life ($t_{1/2}$) in mice of about 1-2 hours, about 1 hour, about 2-3 hours, about 3-4 hours, about 3-5 hours, about 4 hours, about 5 hours, about 4-6 hours, about 5 hours, about 6 hours, about 6-8 hours, or longer. In some embodiments, a PEG functionalized nanoparticle described herein may have half-life ($t_{1/2}$) in mice of about 1-2 hours, about 1 hour, about 2-3 hours, about 3 hours, about 3-4 hours, about 4 hours, about 4-5 hours, about 4-6 hours, about 5 hours, about 6 hours, about 5-7 hours, about 6 hours, about 7 hours, about 6-8 hours, about 7 hours, about 8 hours, about 8-10 hours, or longer. The longer half-life ($t_{1/2}$) in mice for the nanoparticle described herein as compared with the corresponding micelle may be attributed to its better stability. The addition of PLA may make the nanoparticle's hydrophobic core more stable.

For monodisperse PEGn-L-G micelle or monodisperse PEGn-L-G/P nanoparticle, the higher molecular weight (or longer chain) with higher number (n) of repeating units of the monodisperse PEG may result in longer half-life ($t_{1/2}$) in mice, regardless of the same or different functional agent G.

In-vivo study

The PEG functionalized nanoparticle (PEG-L-G/P) described herein comprising a functional agent G that is an anti-cancer drug may be used to treat cancer or reduce tumor size. For example, mPEG45-OCO-PTX/PLA nanoparticles can be used to reduce tumor growth in mice. The antitumor activity or efficacy in reducing tumor volume for the mPEG$_{45}$-OCO-PTX/PLA nanoparticle has shown slightly better than or comparable to the positive control, an approved mPEG-PLA/PTX nanoformulation, in two weeks after injection with a minor difference in the first week.

Applications

The nanoparticles described herein may have many applications in many fields, such as the following:
1. Drug Delivery: the nanoparticles comprising a drug can enhance the effectiveness of delivering drugs and reduce side effects through targeted delivery to specific sites as desired.
2. Imaging Diagnostics: the nanoparticles comprising an imaging diagnostic agent can improve diagnostic accuracy by enhancing image contrast.
3. Immune Stimulation: the nanoparticles comprising an immune-stimulating agent can boost immune responses to improve therapeutic outcomes.
4. Photodynamic Therapy and Photothermal Therapy: the nanoparticles comprising a photoelectric responsive diagnostic and therapeutic agent can achieve precise treatment through photoelectric stimulation.

The nanoparticles described herein may be used for diagnostics, treatment of diseases, conditions or disorders, such as cancer, theranostics, immunotherapy, photodynamic therapy, photothermal therapy, combination drug therapy, drug-immunotherapy combination, drug-photodynamic therapy combination, immunotherapy-photodynamic therapy combination, and drug-immunotherapy-photodynamic therapy combination, etc.

This disclose provides novel nanoparticles and their versatile preparation methods, their superior properties, along with the demonstrated biomedical applications. By modifying the structure and functionality of the nanoparticles, nanoparticles thus prepared can significantly enhance stability and therapeutic efficacy of the nanoparticles. Additionally, the novel nanoparticle comprising a drug has high drug loading efficiency. Furthermore, the nanoparticles provide a versatile method of encapsulation of same or different types of compounds with multiple functions, which enables delivery of dual or multiple components to the desired target areas in mammals including humans or animals for various biomedical applications. This disclosure relating to the novel nanoparticles offers new insights and methods for the further development of nanotechnology in the biomedical field.

A List of Compounds Cited Herewith:

| Synonyms: | Other Name | CAS # | Chemical Structure |
|---|---|---|---|
| PTX | Paclitaxel | 33069-62-4 | 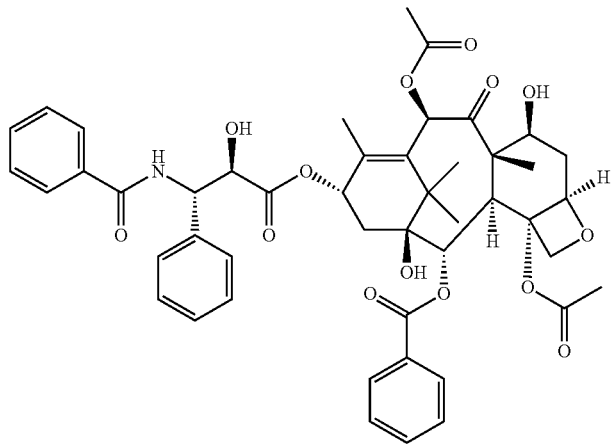 |
| / | Docotaxel | 114977-28-5 | 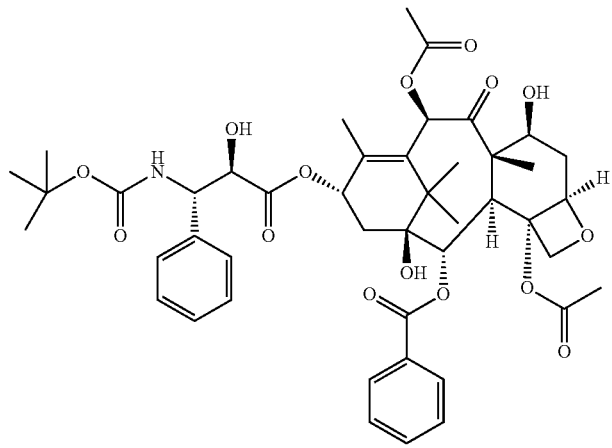 |

| Synonyms: | Other Name | CAS # | Chemical Structure |
|---|---|---|---|
| / | Baccatin III | 27548-93-2 | |
| / | Cabazitaxel | 183133-96-2 | |
| / | 2-Debenzoyl-2-tigloyl Paclitaxel 7-epi-Cephalomannine | 150547-36-7 | |
| SN38 | 7-Ethyl-10-hydroxy-camptothecin | 86639-52-3 | 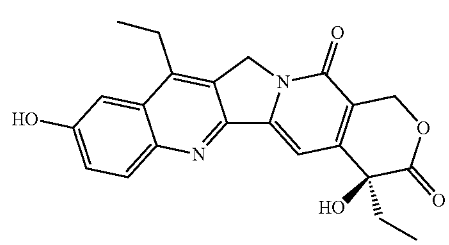 [SMILES: CCc1c2c(nc3ccc(O)cc13)-c1cc3c(c(=O)n1C2)COC(=O)[C@]3(O)CC] |

-continued

| Synonyms: | Other Name | CAS # | Chemical Structure |
|---|---|---|---|
| SN2310 | Tenifatecan | 850728-18-6 | 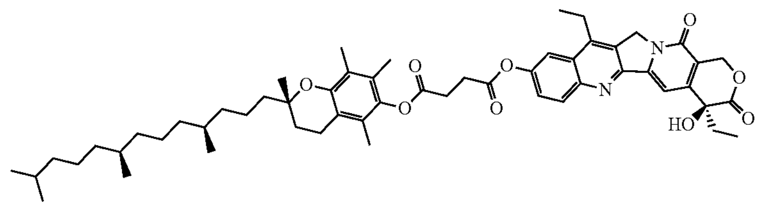 [SMILES: CCc1c2c(nc3ccc(OC(=O)CCC(=O)Oc4c(C)c(C)c5c(c4C)CC[C@](C)(CCC[C@@H](C)CCC[C@@H](C)CCCC(C)C)O5)cc13)-c1cc3c(c(=O)n1C2)COC(=O)[C@]3(O)CC] |
| SN-398 | / | 124623-00-3 | 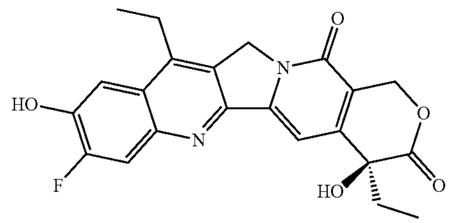 [SMILES: CCc1c2c(nc3cc(F)c(O)cc13)-c1cc3c(c(=O)n1C2)COC(=O)[C@]3(O)CC] |
| CPT-11 | Irinotecan | 97682-44-5 | 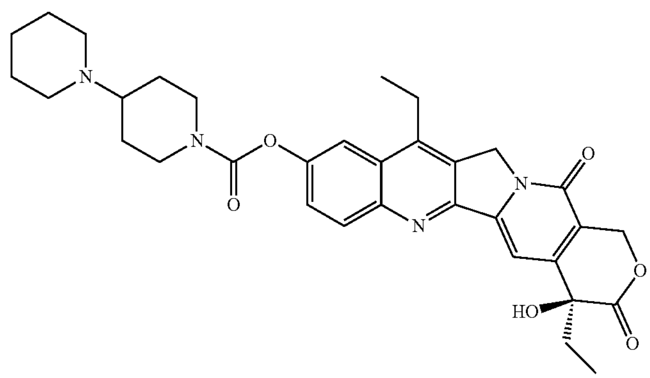 [SMILES: CCc1c2c(nc3ccc(OC(=O)N4CCC(N5CCCCC5)CC4)cc13)-c1cc3c(c(=O)n1C2)COC(=O)[C@]3(O)CC] |
| TPT | Topotecan | 123948-87-8 | 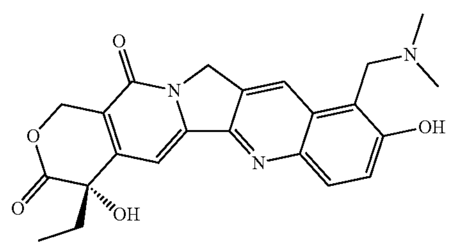 [SMILES: CC[C@@]1(O)C(=O)OCc2c1cc1n(c2=O)Cc2cc3c(CN(C)C)c(O)ccc3nc2-1] |
| DOX | Hydroxy-daunorubicin, Doxorubicin | 23214-92-8 | 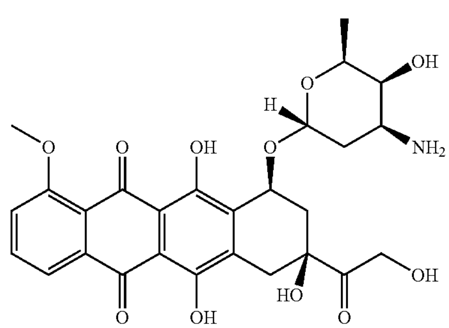 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1] |

| Synonyms: | Other Name | CAS # | Chemical Structure |
|---|---|---|---|
| | Epirubicin | 56420-45-2 | |
| Rapamycin | Sirolimus; AY-22989 | 53123-88-9 | 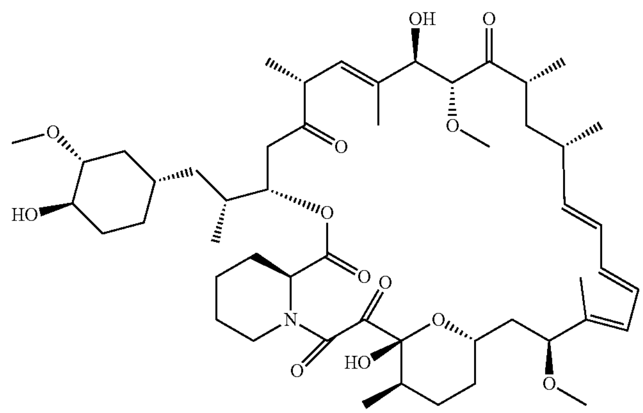 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C] |
| / | Vinblastine sulfate | 143-67-9 | |
| / | Vincristine sulfate | 2068-78-2 | |
| / | cisplatin | 15663-27-1 | |

-continued
| Synonyms: | Other Name | CAS # | Chemical Structure |
|---|---|---|---|
| / | Lamellarin D | 97614-65-8 | 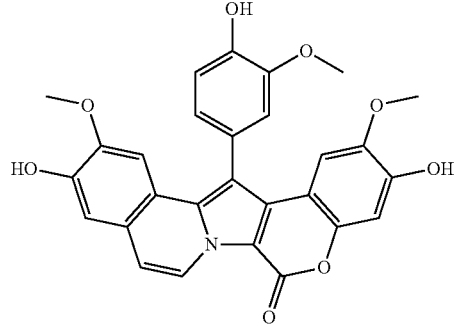 [SMILES: COc1cc(-c2c3c4cc(OC)c(O)cc4oc(=O)c3n3ccc4cc(O)c(OC)cc4c23)ccc1O] |
| Etoposide | / | 33419-42-0 | 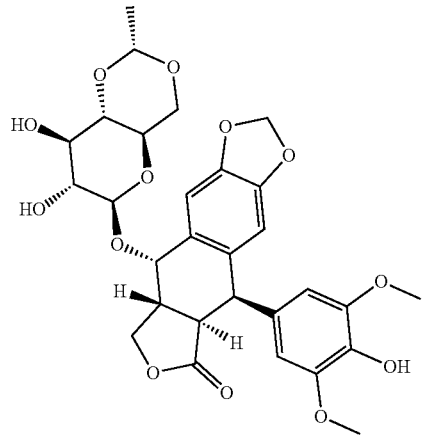 [SMILES: COc1cc([C@@H]2c3cc4c(cc3[C@@H](O[C@@H]3O[C@@H]5CO[C@@H](C)O[C@H]5[C@H](O)[C@H]3O)[C@H]3COC(=O)[C@H]23)OCO4)cc(OC)c1O] |
| / | amphotericin B | 1397-89-3 | 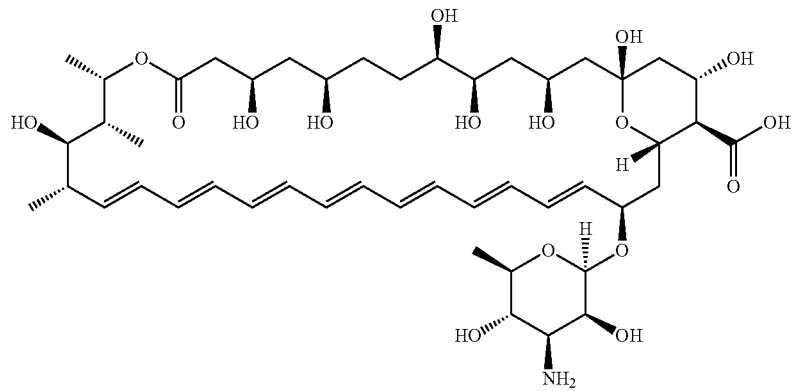 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2C(=O)O] |
| NLG919 | IDO-IN-7 | 1402836-58-1 | 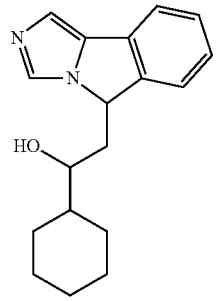 [SMILES: OC(CC1c2ccccc2-c2cncn21)C1CCCCC1] |

| Synonyms: | Other Name | CAS # | Chemical Structure |
|---|---|---|---|
| MSA-2 | / | 129425-81-6 | 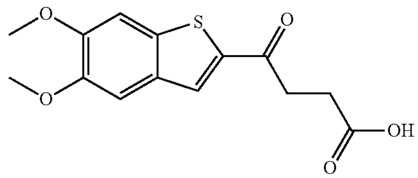 [SMILES: COc1cc2cc(C(=O)CCC(=O)O)sc2cc1OC] |
| DMXAA | Vadimezan; 5,6-dimethyl-9-oxo-9H-xanthene-4-acetic acid; 5,6-Dimethyl-xanthenone-4-acetic Acid; | 117570-53-3 | 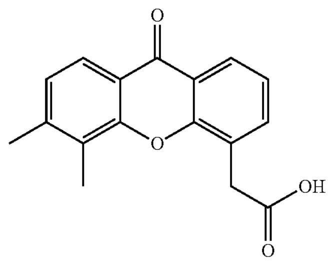 [SMILES: Cc1ccc2c(=O)c3cccc(CC(=O)O)c3oc2c1C] |
| ICG | indocyanine green | 3599-32-4 | 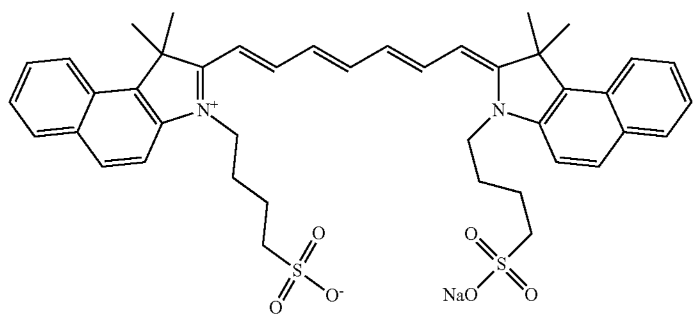 |
| CH1055 | / | 1622250-38-7 | 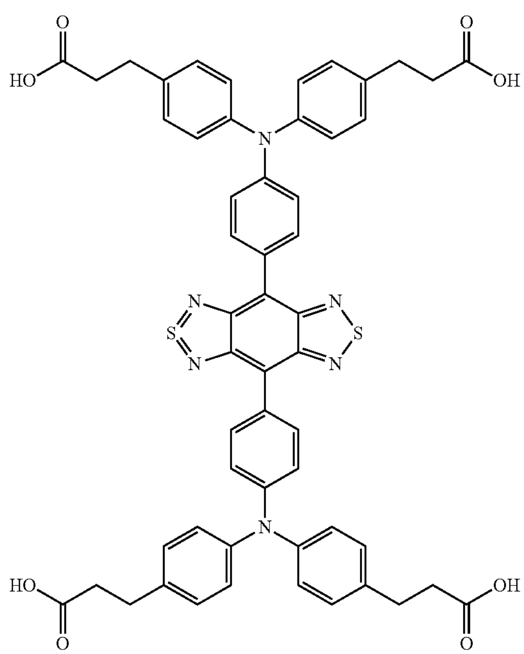 [SMILES: O=C(O)CCc1ccc(N(c2ccc(CCC(=O)O)cc2)c2ccc(-c3c4c(c(-c5ccc(N(c6ccc(CCC(=O)O)cc6)c6ccc(CCC(=O)O)cc6)cc5)c5nsnc35)N=S=N4)cc2)cc1] |

-continued
| Synonyms: | Other Name | CAS # | Chemical Structure |
|---|---|---|---|
| MHI-148 | / | 172971-76-5 | 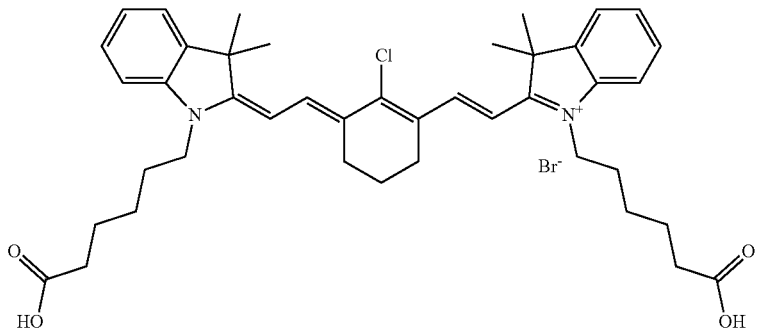 [SMILES: CC1(C)C(/C=C/C2=C(Cl)C(=C/C=C3/N(CCCCCC(=O)O)c4ccccc4C3(C)C)/CCC2)=[N+](CCCCCC(=O)O)c2ccccc21 ; [Br-]] |
| Cypate | / | 95837-47-1 | 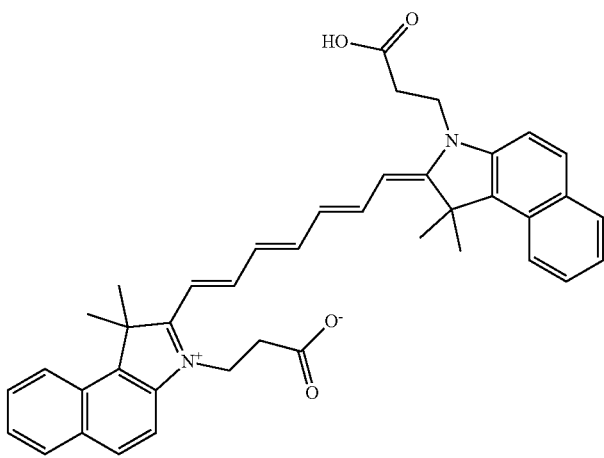 [SMILES: CC1(C)C(/C=C/C=C/C=C/C=C2/N(CCC(=O)O)c3ccc4ccccc4c3C2(C)C)=[N+](CCC(=O)[O-])c2ccc3ccccc3c21] |
| / | BODIPY Derivatives | N/A | 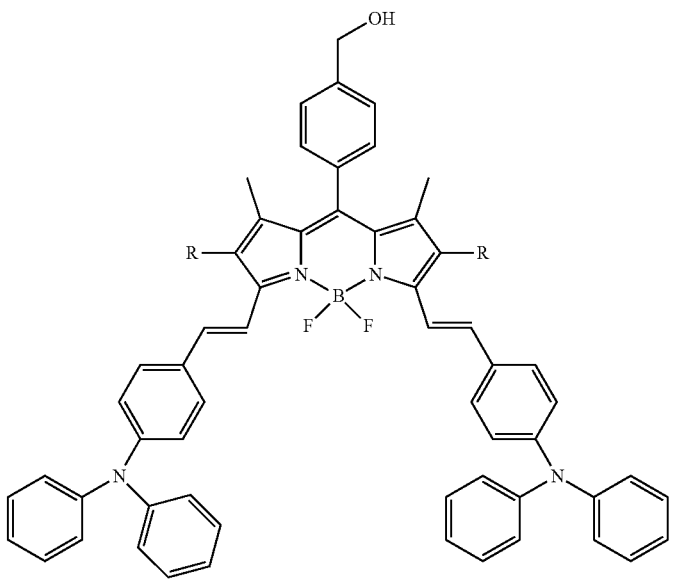 |

| Synonyms: | Other Name | CAS # | Chemical Structure |
|---|---|---|---|
| / | Derivatives of porphyrins | N/A | 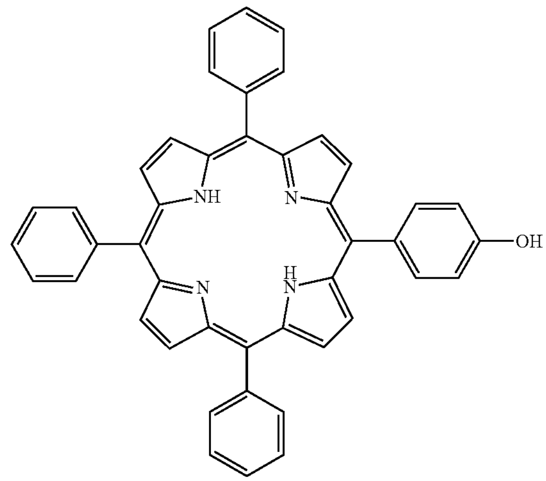 [SMILES: Oc1ccc(-c2c3nc(c(-c4ccccc4)c4ccc([nH]4)c(-c4ccccc4)c4nc(c(-c5ccccc5)c5ccc2[nH]5)C=C4)C=C3)cc1] |

SPECIFICALLY CONTEMPLATED EMBODIMENTS

The following are examples of embodiments that are specifically contemplated by the inventor:

Embodiment 1. A nanoparticle (PEG-L-G/P) comprising:
(1) an amphiphilic compound (PEG-L-G) comprising a hydrophilic polyethylene glycol (PEG) covalently linked with a hydrophobic functional agent (G) via L; and
(2) a hydrophobic polymer (P);
  wherein L is a covalent bond or a linker comprising reactive functional groups which connects the PEG to the G via covalent bonds;
  wherein the G is selected from a compound having certain function, an active pharmaceutical ingredient (API) with therapeutic function, an imaging diagnostic agent, an immune-stimulating agent, a photoelectric-responsive diagnostic agent, a tumor microenvironment-responsive agent, or a combination thereof; and
  wherein the nanoparticle (PEG-L-G/P) has a hydrophobic core comprising the G and the P, and a hydrophilic outer layer comprising the PEG.

Embodiment 2. The nanoparticle of embodiment 1, wherein a solution is encapsulated in the nanoparticle.

Embodiment 3. The nanoparticle of embodiment 1 or 2, wherein the PEG is linear, branched, dendritic, or comb-shaped, with a molecular weight distribution (polydisperse) or a single molecular weight (monodisperse), and molecular weight ranges from 500 to 20,000 Daltons.

Embodiment 4. The nanoparticle of embodiment 1, 2 or 3, wherein the PEG comprises a functional group.

Embodiment 5. The nanoparticle of embodiment 1, 2, 3, or 4, wherein the PEG comprises a methoxy group at the free end (mPEG).

Embodiment 6. The nanoparticle of any preceding embodiment, wherein the L is a chemical bond, comprising an ester bond, an ether bond, a carbonate bond, an amide bond, a disulfide bond, an anhydride bond, a hydrazone bond, a thioether bond, a selenide bond, a peptide bond, a phosphodiester bond, or a glycosidic bond.

Embodiment 7. The nanoparticle of any preceding embodiment, wherein the G comprises paclitaxel, tricaplyl paclitaxel, doxorubicin, epirubicin, vinblastine, vincristine, etoposide, irinotecan, topotecan, mitomycin, tamoxifen, ifosfamide, cyclophosphamide, carmustine, SN38 or its derivative, a platinum derivative, MSA-2, DMXAA (Vadimezan), NLG919, IR-26, IR-1061, IR-808, ICG, CH1055, AIE molecule, porphyrin, phthalocyanine, chlorin, texaphyrin, phenothiazinium, rose bengal, indocyanine green (ICG), hypericin, or a combination thereof.

Embodiment 8. The nanoparticle of any preceding embodiment, wherein the G comprises two or more types of compounds having different functions.

Embodiment 9. The nanoparticle of any preceding embodiment, wherein the polymer P is a polyester or its derivative, a polycarbonate or its derivative, a polyanhydride, or a combination thereof forming a copolymer.

Embodiment 10. The nanoparticle of any preceding embodiment, wherein the polymer P is PLA, PCL, PHA, PHB, PHV, PGA, poly(trimethylene carbonate), a derivative thereof, or a combination thereof forming a copolymer.

Embodiment 11. The nanoparticle of any preceding embodiment, wherein the polymer P is poly(lactic acid) (PLA).

Embodiment 12. The nanoparticle of any preceding embodiment, wherein the mass ratio of PEG-L-G to polymer P in the nanoparticles is about 1:1 to about 20:1 (1-20).

Embodiment 13. The nanoparticle of any preceding embodiment, wherein the particle size is about 30 nm to about 200 nm.

Embodiment 14. The nanoparticle of any preceding embodiment, wherein the particle size is about 50 nm to about 150 nm.

Embodiment 15. The nanoparticle of any preceding embodiment, wherein the particle size is about 70 nm to about 125 nm.

Embodiment 16. The nanoparticle of any preceding embodiment selected from the group consisting of:
  Polydisperse mPEG$_{2k}$-CH2COO-PTX/PLA Nanoparticle;
  Monodisperse mPEG$_{44}$-CH$_2$COO-PTX/PLA Nanoparticle;
  Polydisperse mPEG$_{2k}$-OCO-PTX/PLA Nanoparticle;
  Monodisperse mPEG$_{45}$-OCO-PTX/PLA Nanoparticle;
  Monodisperse mPEG$_{23x2}$-Lysine-PTX/PLA Nanoparticle;

Polydisperse mPEG$_{2k}$-CH$_2$CONHCH$_2$CH$_2$—SS—CH$_2$CH$_2$COO—SN38/PLA Nanoparticle;

Monodisperse mPEG$_{44}$-CH$_2$CONHCH$_2$CH$_2$—SS—CH$_2$CH$_2$COO—SN38/PLA Nanoparticle;

Polydisperse mPEG$_{2k}$-CH$_2$CONH-TPE/PLA Luminescent Nanoparticle;

Monodisperse mPEG$_{45}$-O(O=C)-MSA-2/PLA Nanoparticle;

Monodisperse mPEG$_{62}$-O(O=C)-MSA-2/PLA Nanoparticle;

Monodisperse mPEG$_{81}$-O(O=C)-MSA-2/PLA Nanoparticle;

Polydisperse mPEG$_{2k}$-O(O=C)-MSA-2/PLA Nanoparticle;

(mPEG$_{80}$-CH$_2$COO-PTX and mPEG$_{80}$-CH$_2$CONHCH$_2$CH$_2$—SS—CH$_2$CH$_2$COO—SN38)/PLA Nanoparticle;

(mPEG$_{80}$-CH$_2$COO-PTX and mPEG$_{81}$-O(O=C)-MSA-2)/PLA Nanoparticle;

(mPEG$_{80}$-CH$_2$CONHCH$_2$CH$_2$—SS—CH$_2$CH$_2$COO—SN38 and mPEG$_{81}$-O(O=C)-MSA-2)/PLA Nanoparticle;

Monodisperse mPEG$_{44}$-CH$_2$CONH—CH$_2$CH$_2$—SS—CH$_2$CH$_2$O(O=C)-MSA-2;

Monodisperse mPEG$_{44}$-CH$_2$CONH—CH$_2$CH$_2$—SS-di-MSA-2;

Monodisperse mPEG$_{45}$-succinate-NGL-919; or

Monodisperse mPEG$_{44}$-CONH—CH$_2$CH$_2$—SS—CH$_2$CH$_2$O(O=C)-MHI-148.

Embodiment 17. A lyophilized product of the nanoparticle of any preceding embodiment, which is a powder, wherein the powder is reconstituted in water or an electrolyte aqueous solution to obtain a colloidal solution of the nanoparticle.

Embodiment 18. A method for preparing the nanoparticle (PEG-L-G/P) of any preceding embodiment, comprising:
(a) co-dissolving the PEG-L-G compound and the polymer P in one or more organic solvents to form an organic solution;
(b) adding dropwise or continuously the organic solution in step a to an aqueous medium to form a mixture;
(c) mixing the mixture in step b to obtain an emulsion, and optionally adding additional aqueous medium; and
(d) removing the organic solvent(s) to obtain a stable nanoparticle aqueous solution (PEG-L-G/P),
wherein the aqueous medium is water or phosphate-buffered solution.

Embodiment 19. The method of embodiment 18, wherein the aqueous medium is phosphate-buffered solution.

Embodiment 20. A pharmaceutical composition comprising a nanoparticle of any preceding embodiment, and a pharmaceutically acceptable excipient.

Embodiment 21. The pharmaceutical composition of embodiment 20; wherein the nanoparticle comprises two or more types of PEG-L-G with G being different.

Embodiment 22. The pharmaceutical composition of embodiment 20, comprising a plurality of nanoparticles.

Embodiment 23. The pharmaceutical composition of embodiment 20, wherein the nanoparticle comprises a single type of nanoparticle.

Embodiment 24. The pharmaceutical composition of embodiment 20, wherein the nanoparticle comprises multiple types of nanoparticle.

Embodiment 25. The pharmaceutical composition of embodiment 21, wherein the nanoparticle comprise two types of therapeutic drugs.

Embodiment 26. A method of targeted delivery of G to a mammal, comprising administering the nanoparticle (PEG-L-G/P) or the pharmaceutical composition comprising the same according to any preceding embodiment to the target areas in a mammal.

Embodiment 27. A method for treating a disease, condition or disorder; targeted diagnostics; immunotherapy; drug-immunotherapy; drug-photodynamic therapy; immunotherapy-photodynamic therapy; drug-immunotherapy-photodynamic therapy; or a combination thereof in a mammal, comprising administering a nanoparticle (PEG-L-G/P) or a pharmaceutical composition comprising the same, according to any preceding embodiment to the mammal.

Embodiment 28. The method of embodiment 27, wherein the method is for treating a disease, condition or disorder in a mammal, wherein G is a therapeutic drug.

Embodiment 29. The method of embodiment 28, wherein the G is an anti-cancer drug.

Embodiment 30. The method of embodiment 26, 27, 28, or 29, wherein the mammal is a human being.

EXAMPLES

Example 1: Synthesis of mPEG-L-G and Preparation of Nanoparticles, i.e., Synthesis of Polydisperse mPEG$_{2k}$-CH$_2$COO-PTX and Preparation of mPEG$_{2k}$-CH$_2$COO-PTX/PLA Nanoparticles Synthesis of Polydisperse mPEG$_{2k}$-CH$_2$COO-PTX 2.00 g (1.05 mmol) of mPEG$_{2k}$-CH$_2$COOH, 817.15 mg (0.96 mmol) of PTX, 262.30 mg (1.37 mmol) of EDC-HCl, and 56.70 mg (0.464 mmol) of DMAP were dissolved in 20 mL of DCM, and the mixture was stirred at room temperature for 12 hours. After the reaction, 10 ml of DCM was added to dilute the reaction mixture, and impurities were washed away with an equal volume of water for three times, the DCM phase was dried with MgSO$_4$ and then concentrated under reduced pressure. Subsequently, 20 mL of ethyl acetate (EA) was added; and the flask was placed at −18° C. overnight for recrystallization. After filtration and vacuum drying, a white powder of mPEG$_{2k}$-CH$_2$COO-PTX (1.3 g, yield 46%) was obtained.

Figure 2A:
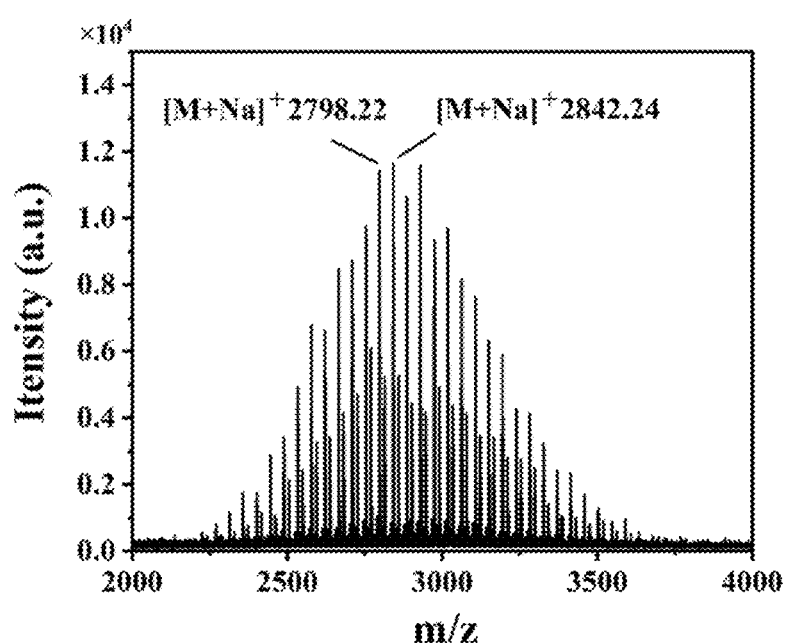
FIG. 2a. is the MALDI-ToF spectrum of polydisperse mPEG$_{2k}$-CH$_2$COO-PTX

MALDI-TOF-MS: Due to the polydispersity of mPEG$_{2k}$-CH$_2$COOH, the mass spectrum presents various molecular weights of the same series mPEG-CH$_2$COOPTX. The mass spectrum peak [M+Na]$^+$=2842.24 Dalton can be observed. The mass spectrum is shown in FIG. 2a.

$^1$H NMR (600 MHz, Chloroform-d): δ 8.15 (d, J=7.7 Hz, 2H), 7.78-7.74 (m, 2H), 7.62 (t, J=7.3 Hz, 1H), 7.55-7.43 (m, 5H), 7.39 (s, 4H), 7.29 (s, 1H), 6.30 (s, 1H), 6.26 (s, 1H), 6.01 (d, J=9.2 Hz, 1H), 5.69 (d, J=7.0 Hz, 1H), 5.53 (s, 1H), 4.98 (s, 1H), 4.45 (s, 1H), 4.32 (s, 2H), 4.20 (s, 2H), 3.83 (s, 1H), 3.64 (d, J=28.6 Hz, 170H), 3.38 (s, 3H), 2.54 (d, J=28.2 Hz, 2H), 2.47 (s, 3H), 2.40 (s, 1H), 2.23 (s, 3H), 2.21 (s, 1H), 1.95 (s, 3H), 1.88 (d, J=13.0 Hz, 1H), 1.69 (s, 3H), 1.24 (s, 3H), 1.14 (s, 3H).

Preparation of mPEG-L-G/PLA Nanoparticles (mPEG$_{2k}$-CH$_2$COO-PTX/PLA Nanoparticles)

5 mg of polylactide (PLA, molecular weight 50k Dalton) and 40 mg of mPEG$_{2k}$-CH$_2$COO-PTX were dissolved in 1 mL of ethyl acetate, then add 5 mL of phosphate-buffered saline (PBS, pH=7.4), and sonicate for emulsification (150 Hz, 10 min, 0° C.). Subsequently, 5 mL of PBS buffer solution was added, then the mixture was transferred to a 100 mL open beaker, and stirred magnetically at room temperature for 4 hours to remove the organic solvent, resulting in mPEG$_{2k}$-CH$_2$COO-PTX/PLA nanoparticles. The content of mPEG$_{2k}$-CH$_2$COO-PTX in the nanoparticle solution can be calculated using the PTX standard curve. Particle size is measured using a particle size analyzer and a transmission electrical microscopy (TEM).

Example 2: Synthesis of mPEG-L-G(PTX) and Preparation of Nanoparticles, i.e., Synthesis of Monodisperse mPEG$_{44}$-CH$_2$COO-PTX and Preparation of Monodisperse mPEG$_{44}$-CH$_2$COO-PTX/PLA Nanoparticles Synthesis of Monodisperse mPEG$_{44}$-CH$_2$COO-PTX 2.00 g (0.99 mmol) of mPEG$_{44}$-CH$_2$COOH, 765.50 mg (0.90 mmol) of PTX, 245.70 mg (1.28 mmol) of EDC-HCl, and 53.10 mg (0.43 mmol) of DMAP were dissolved in 20 mL of DCM. The subsequent operations are the same as in Example 1, resulting in a white powder of mPEG$_{44}$-CH$_2$COO-PTX (1.50 g, yield 54%).

Figure 2B:
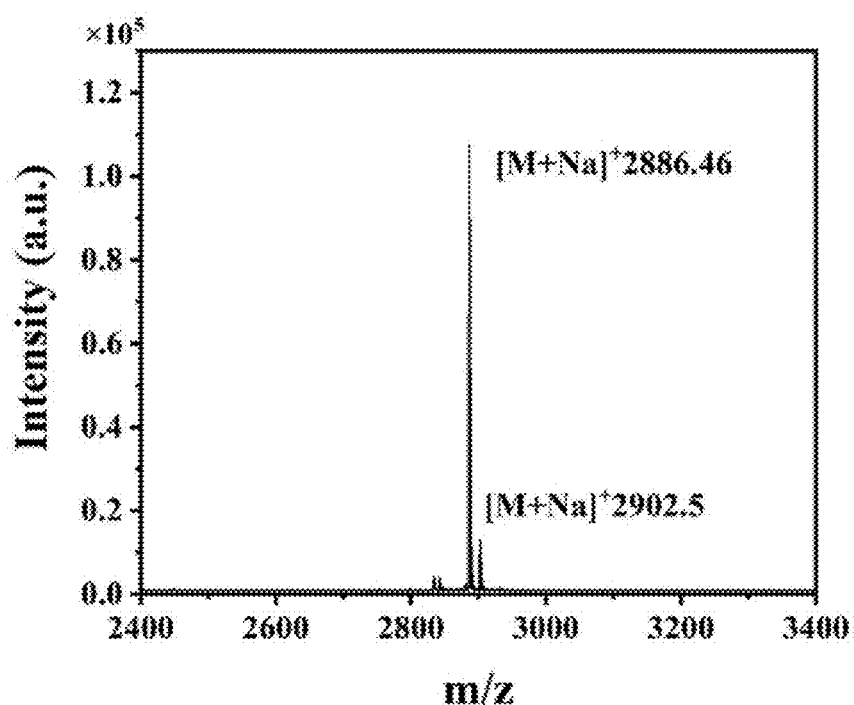
FIG. 2b is the MALDI-ToF spectrum of monodisperse mPEG$_{44}$-CH$_2$COO-PTX.

MALDI-TOF-MS Mass Spectrum: Due to the reaction of a single molecular weight of mPEG$_{44}$-CH$_2$COOH with paclitaxel, the resulting product is a single molecular weight mPEG$_{44}$-CH$_2$COO-PTX. A single molecular weight [M+Na]$^+$=2886.46 is observed. The mass spectrum is shown in FIG. 2(b).

$^1$H NMR (600 MHz, Chloroform-d): δ 8.15 (d, J=7.3 Hz, 2H), 7.77 (d, J=7.3 Hz, 2H), 7.61 (d, J=7.4 Hz, 1H), 7.55-7.44 (m, 5H), 7.40 (d, J=17.4 Hz, 4H), 7.35 (s, 1H), 6.30 (s, 1H), 6.26 (t, J=8.7 Hz, 1H), 6.02 (dd, J=9.3, 2.6 Hz, 1H), 5.70 (d, J=7.1 Hz, 1H), 5.54 (d, J=2.8 Hz, 1H), 4.98 (d, J=11.2 Hz, 1H), 4.48-4.42 (m, 1H), 4.33 (d, J=8.5 Hz, 1H), 4.29 (d, J=17.1 Hz, 1H), 4.23-4.17 (m, 2H), 3.82 (d, J=7.0 Hz, 1H), 3.65 (s, 174H), 3.38 (s, 3H), 2.62-2.50 (m, 2H), 2.48 (s, 3H), 2.44-2.38 (m, 1H), 2.23 (s, 3H), 2.23-2.18 (m, 1H), 1.95 (s, 3H), 1.89 (t, J=13.9 Hz, 2H), 1.69 (s, 3H), 1.23 (s, 3H), 1.14 (s, 3H).

Preparation of Monodisperse mPEG$_{44}$-CH$_2$COO-PTX/PLA Nanoparticles

The nanoparticles were prepared using the same method as in Example 1.

Example 3: Synthesis of mPEG-L-G(PTX) and Preparation of Nanoparticles, i.e., Synthesis of Polydisperse mPEG$_{2k}$-OCO-PTX and Preparation of Polydisperse mPEG$_{2k}$-OCO-PTX/PLA Nanoparticles Synthesis of Polydisperse mPEG$_{2k}$-OCO-PTX (as shown in Scheme 2)

2.00 g (1.05 mmol) of mPEG$_{2k}$-NO$_2$, 1.79 g (2.1 mmol) of PTX, and 64.30 mg (0.53 mmol) of DMAP were dissolved in 15 mL of DCM and the mixture was stirred at room temperature for 24 hours. After the reaction, 20 mL of DCM was added for dilution and the was extracted by 50 ml of water for three times, the organic phase was dried with MgSO$_4$, and concentrated under reduced pressure. 20 mL of EA was added for recrystallization at a −18° C. freezer overnight, after filtration and vacuum drying, a white powder of mPEG$_{2k}$-OCO-PTX (2.20 g, yield 58%) was obtained.

Figure 3A:
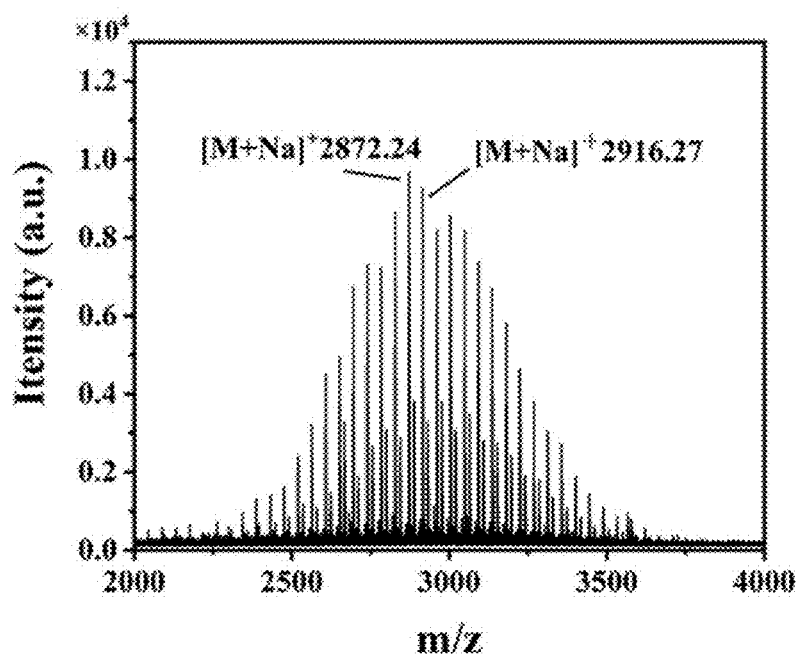
FIG. 3a is the MALDI-ToF spectrum of polydisperse mPEG$_{2k}$-OCO-PTX carbonate.

MALDI-TOF-MS: Similar to mPEG$_{2k}$-CH$_2$COO-PTX, mPEG$_{2k}$-OCO-PTX presents the molecular weights of each homologue, with an observed [M+Na]$^+$=2872.24. The mass spectrum is shown in FIG. 3(a).

$^1$H NMR (600 MHz, Chloroform-d): δ 8.15 (d, J=7.3 Hz, 2H), 7.76 (d, J=7.3 Hz, 2H), 7.61 (s, 1H), 7.52 (s, 3H), 7.41 (d, J=9.9 Hz, 6H), 7.36 (s, 1H), 7.01 (d, J=9.3 Hz, 1H), 6.29 (s, 2H), 5.99 (s, 1H), 5.69 (d, J=7.1 Hz, 1H), 5.42 (d, J=2.6 Hz, 1H), 4.98 (d, J=9.7 Hz, 1H), 4.44 (s, 1H), 4.32 (d, J=13.3 Hz, 3H), 4.21 (d, J=8.5 Hz, 1H), 3.82 (s, 1H), 3.64 (d, J=9.9 Hz, 184H), 3.38 (s, 3H), 2.54 (d, J=30.2 Hz, 2H), 2.46 (s, 3H), 2.42-2.37 (m, 1H), 2.23 (s, 3H), 2.20 (d, J=6.5 Hz, 1H), 1.97 (s, 2H), 1.93 (s, 3H), 1.69 (s, 3H), 1.24 (s, 3H), 1.14 (s, 3H).

Preparation of Polydisperse mPEG$_{2k}$-OCO-PTX/PLA Nanoparticles

The nanoparticles were prepared using the same method as in Example 1.

Example 4: Synthesis of mPEG-L-G(PTX) and Preparation of Nanoparticles, i.e., Synthesis of Monodisperse mPEG$_{45}$-OCO-PTX Carbonate and Preparation of Monodisperse mPEG$_{45}$-OCO-PTX/PLA Nanoparticles Synthesis of Monodisperse mPEG$_{45}$-OCO-PTX Using 2.0 g (0.92 mmol) of mPEG$_{45}$-O(C=O)—C$_6$H$_4$—NO$_2$ and 1.57 g (1.84 mmol) of PTX as raw materials, the subsequent operations are the same as in Example 3, resulting in mPEG$_{45}$-OCO-PTX (2.5 g, 69% yield) as a white powder.

Figure 3B:
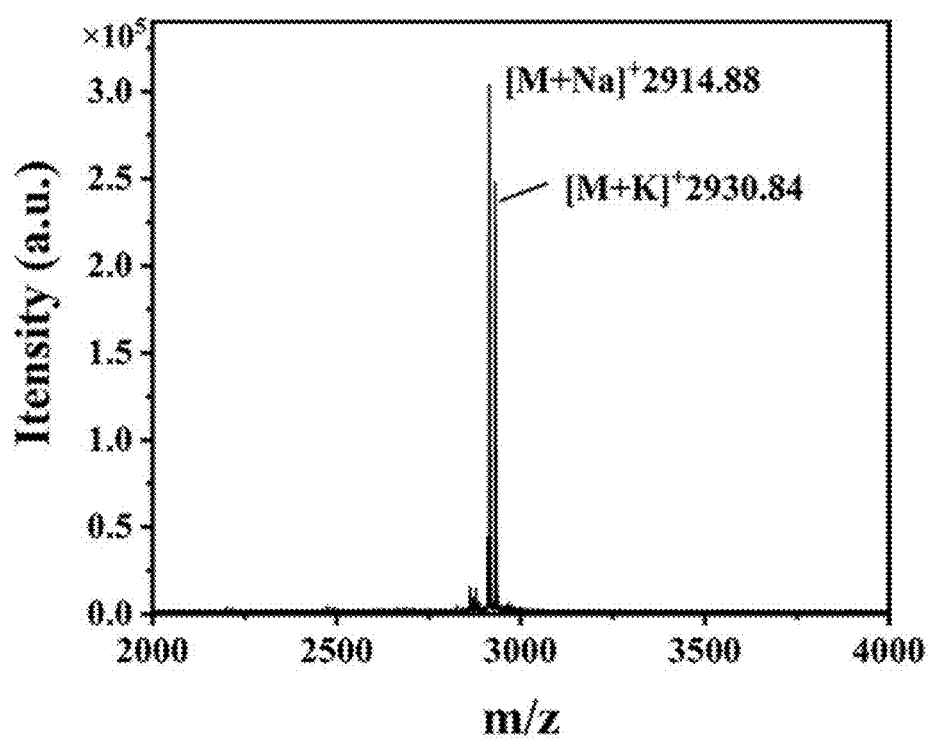
FIG. 3b is the MALDI-ToF spectrum of monodisperse mPEG$_{45}$-OCO-PTX carbonate.
Figure 4A:
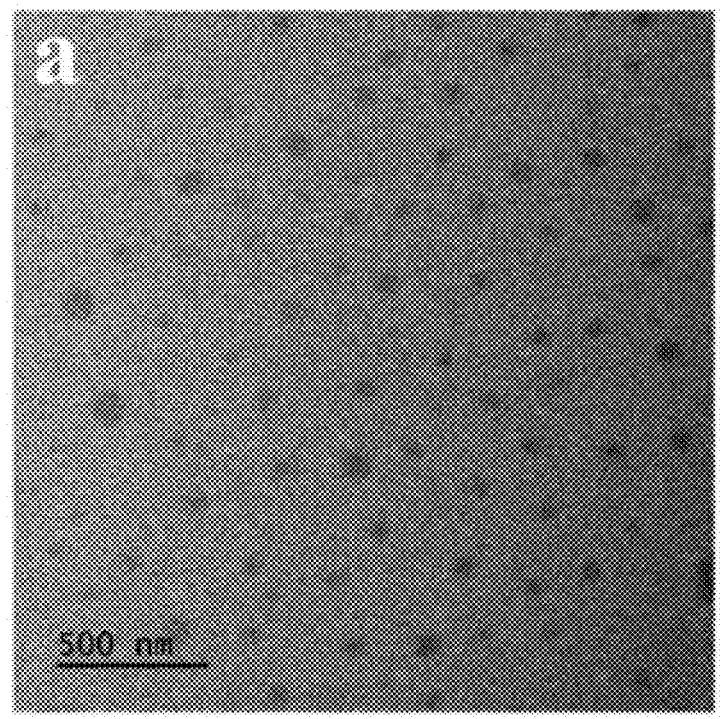
FIG. 4a is the transmission electron microscopy image of mPEG$_{2k}$-CH$_2$COO-PTX micelles.
Figure 4B:
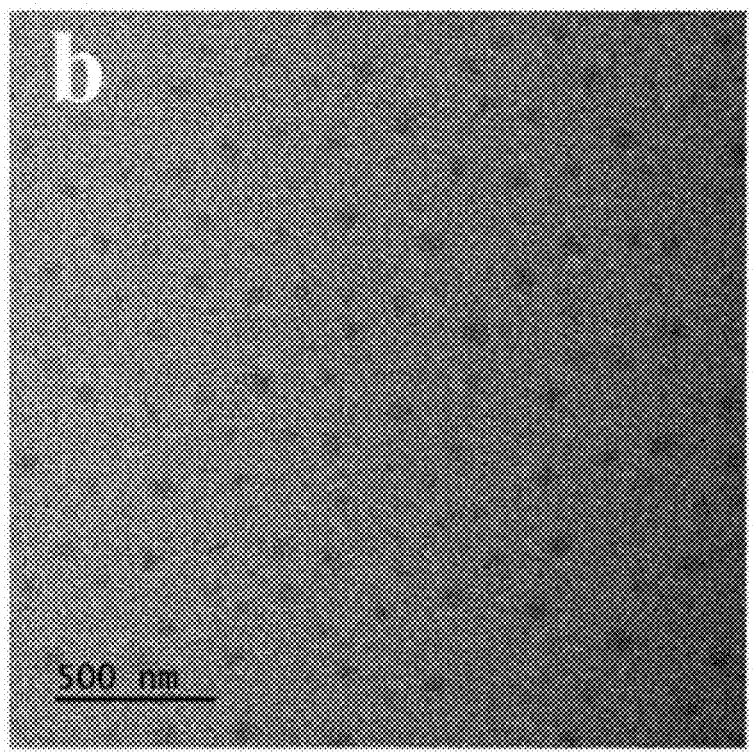
FIG. 4b is the transmission electron microscopy image of mPEG$_{44}$-CH$_2$COO-PTX micelles.
Figure 4C:
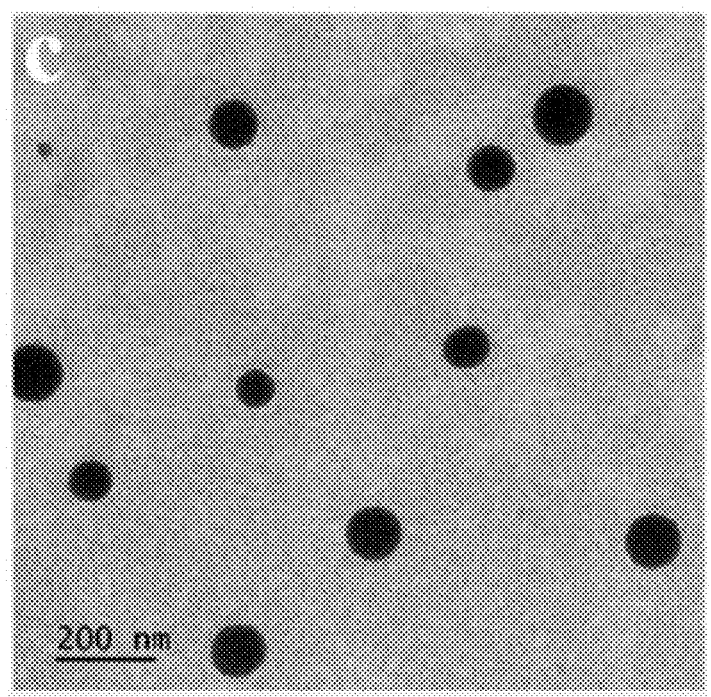
FIG. 4c is the transmission electron microscopy image of mPEG$_{2k}$-CH$_2$COO-PTX/PLA nanoparticles.
Figure 4D:
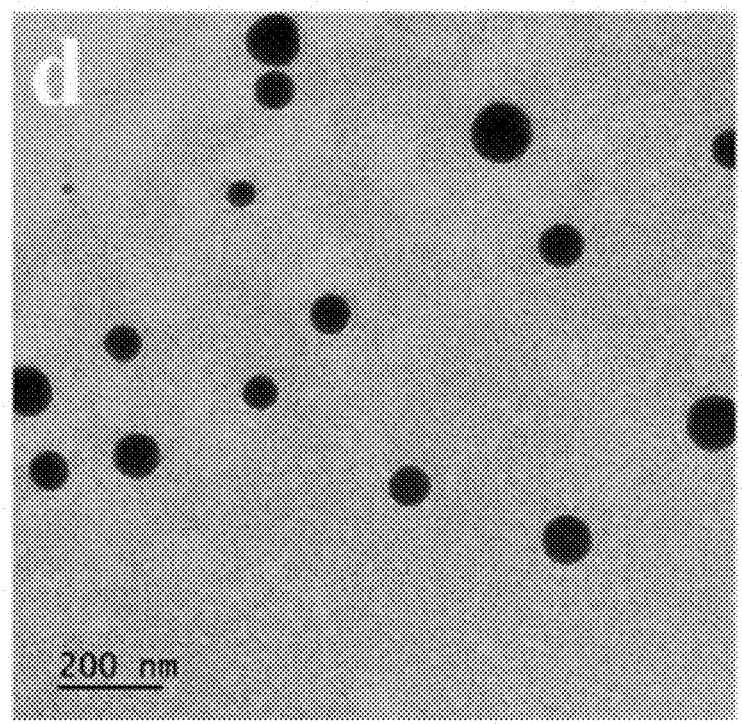
FIG. 4d is the transmission electron microscopy image of mPEG$_{44}$-CH$_2$COO-PTX/PLA nanoparticles.

MALDI-TOF-MS: [M+Na]$^+$=2914.88. The mass spectrum is shown in FIG. 3(b).

$^1$H NMR (600 MHz, Chloroform-d): δ 8.15 (d, J=7.8 Hz, 2H), 7.76 (d, J=7.5 Hz, 2H), 7.62 (s, 1H), 7.53 (d, J=7.8 Hz, 3H), 7.42 (d, J=8.5 Hz, 6H), 7.36 (s, 1H), 7.01 (d, J=9.3 Hz, 1H), 6.28 (d, J=13.1 Hz, 2H), 5.98 (d, J=9.3 Hz, 1H), 5.69 (d, J=7.1 Hz, 1H), 5.42 (d, J=2.5 Hz, 1H), 4.98 (d, J=9.5 Hz, 1H), 4.45 (s, 1H), 4.35-4.26 (m, 3H), 4.21 (d, J=8.5 Hz, 1H), 3.81 (d, J=7.0 Hz, 1H), 3.72-3.55 (m, 180H), 3.38 (s, 3H), 2.54 (d, J=21.2 Hz, 2H), 2.46 (s, 3H), 2.43-2.37 (m, 1H), 2.24 (s, 3H), 2.20 (d, J=6.5 Hz, 1H), 1.93 (s, 2H), 1.90 (s, 3H), 1.69 (s, 3H), 1.24 (s, 3H), 1.14 (s, 3H).

Preparation of Monodisperse
mPEG$_{45}$-OCO-PTX/PLA Nanoparticles

The nanoparticles were prepared using the same method as in Example 1.

Example 5: Particle Size, Particle Size Distribution, and Zeta Potential of mPEG-L-PTX Micelles and mPEG-L-PTX/PLA Nanoparticles

TABLE 1

Particle size (D$_h$), particle size distribution (PDI), and Zeta potential, particle size determined by TEM (D$_{TEM}$) of mPEG$_{2k}$-CH$_2$COO-PTX, MPEG$_{44}$-CH$_2$COO-PTX micelles, and mPEG$_{2k}$-CH$_2$COO-PTX/PLA, MPEG$_{44}$-CH$_2$COO-PTX/PLA, MPEG$_{2k}$-OCO-PTX/PLA, MPEG$_{45}$-OCO-PTX/PLA nanoparticles

| Items | Type | D$_h$ (nm) | PDI | Zeta Potential (mV) | D$_{TEM}$ (nm) |
|---|---|---|---|---|---|
| mPEG$_{2k}$-CH$_2$COO-PTX | Micelles | 119.7 ± 0.9 | 0.20 ± 0.01 | −9.71 ± 1.24 | 83.4 ± 14.4 |
| mPEG$_{44}$-CH$_2$COO-PTX | Micelles | 121.9 ± 1.6 | 0.17 ± 0.01 | −10.92 ± 0.73 | 84.4 ± 13.8 |
| mPEG$_{2k}$-CH$_2$COO-PTX/PLA | NPs | 106.1 ± 1.5 | 0.16 ± 0.02 | −2.52 ± 0.88 | 91.7 ± 11.4 |
| mPEG$_{44}$-CH$_2$COO-PTX/PLA | NPs | 111.1 ± 1.4 | 0.18 ± 0.01 | −3.43 ± 1.70 | 90.1 ± 11.2 |
| mPEG$_{2k}$-SS-COO-SN38/PLA | NPs | 119.7 ± 0.9 | 0.20 ± 0.01 | −9.71 ± 1.24 | 88.4 ± 13.4 |
| mPEG$_{44}$-SS-COO-SN38/PLA | NPs | 121.9 ± 1.6 | 0.17 ± 0.01 | −10.92 ± 0.73 | 88.3 ± 9.2 |

The above data indicates that the dispersity of polyethylene glycol does not affect the particle size. Compared to the micelles without PLA, the particle size of the PTX nanoparticles decreases after adding PLA, as determined by DLS, indicating that the core becomes more compact. While the particle size of PTX nanoparticles is larger than the PTX micelles, as determined by TEM, due to incorporation of PLA into the hydrophobic core of PTX nanoparticles.

FIG. 4 shows the transmission electron microscopy (TEM) images of prepared (a) mPEG$_{2k}$-CH$_2$COO-PTX micelles, (b) mPEG$_{44}$-CH$_2$COO-PTX micelles, (c) mPEG$_{2k}$-CH$_2$COO-PTX/PLA nanoparticles and (d) mPEG$_{44}$-CH$_2$COO-PTX/PLA nanoparticles, the diameters of micelles and nanoparticles determined by TEM are also summarized in the Table 1. The diameters determined by TEM are always smaller than these determined by DLS, due to dried and high vacuum environment. In addition, the particle size of PTX nanoparticles is larger than that of PTX micelles. The morphology of nanoparticles, as observed by TEM, is distinctly different from that of micelles. Nanoparticles are denser and have clearer boundaries, which is attributed to the incorporation of PLA into their hydrophobic core.

Example 6. Stability Testing of mPEG-L-PTX Micelles and mPEG-L-PTX/PLA Nanoparticles in PBS (pH=7.4)

Figure 5:
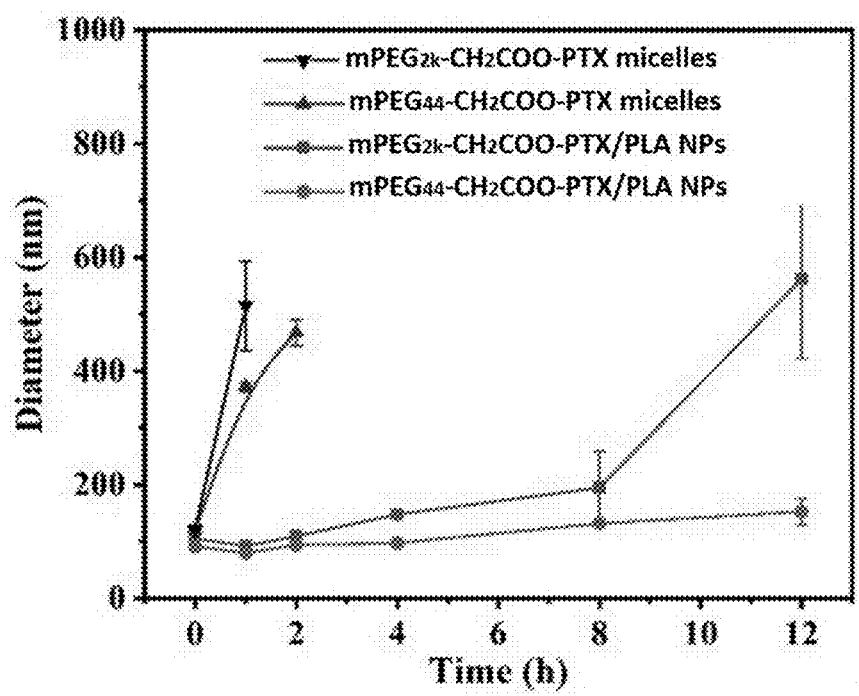
FIG. 5 depicts the stability of mPEG$_{2k}$-CH$_2$COO-PTX, mPEG$_{44}$-CH$_2$COO-PTX micelle, and mPEG$_{2k}$-CH$_2$COO-PTX/PLA, mPEG$_{44}$-CH$_2$COO-PTX/PLA nanoparticle in PBS solution at pH 7.4 and 37° C.

Take 3 mL of mPEG$_{2k}$-CH$_2$COO-PTX, mPEG$_{44}$-CH$_2$COO-PTX micelle solutions, and mPEG$_{2k}$-CH$_2$COO-PTX/PLA, mPEG$_{44}$-CH$_2$COO-PTX/PLA nanoparticle solutions in PBS (pH=7.4), place them in a 37° C. incubator, and measure their particle size and particle size distribution (PDI) at 1, 2, 4, 8, and 12 hours, the results are shown in FIG. 5. The stability of mPEG$_{2k}$-CH$_2$COO-PTX and mPEG$_{44}$-CH$_2$COO-PTX micelle solutions in PBS does not exceed 1 hour. The particle size of mPEG$_{2k}$-CH$_2$COO-PTX/PLA nanoparticles increases after 2 hours and increases sharply after 8 hours; the particle size of mPEG$_{44}$-CH$_2$COO-PTX/PLA nanoparticles increases slowly after 4 hours and increases by 60 nm at 12 hours. These results indicate that mPEG$_{2k}$-CH$_2$COO-PTX micelles have poor stability and monodisperse PEG used can improve the stability of nanoparticles in PBS. PLA plays an important role in enhancing the stability of mPEG-CH$_2$COO-PTX/PLA nanoparticles.

Figure 6A:
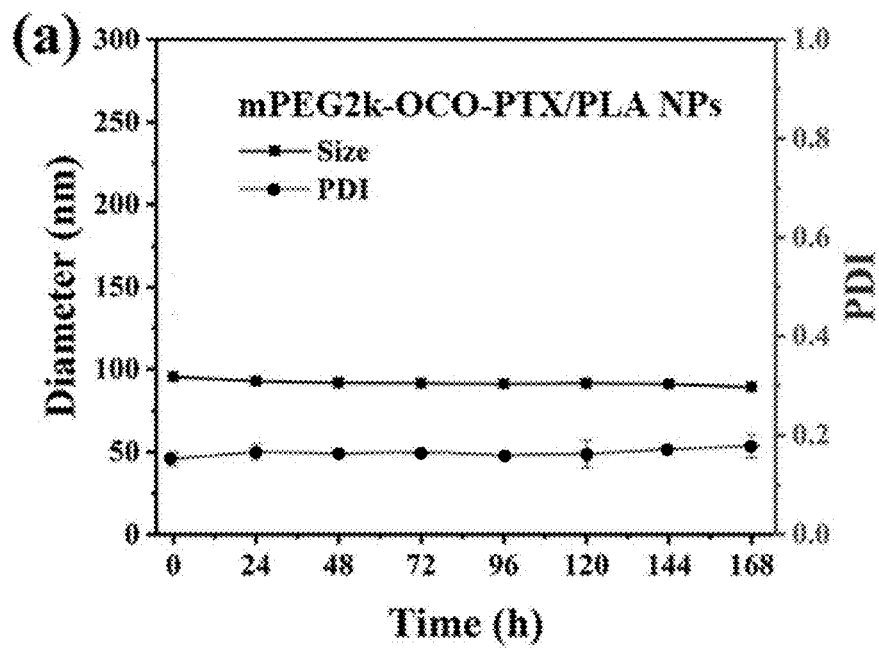
FIG. 6a depicts the stability results of mPEG$_{2k}$-OCO-PTX/PLA nanoparticles in PBS solution at pH 7.4 and 37° C.
Figure 6B:
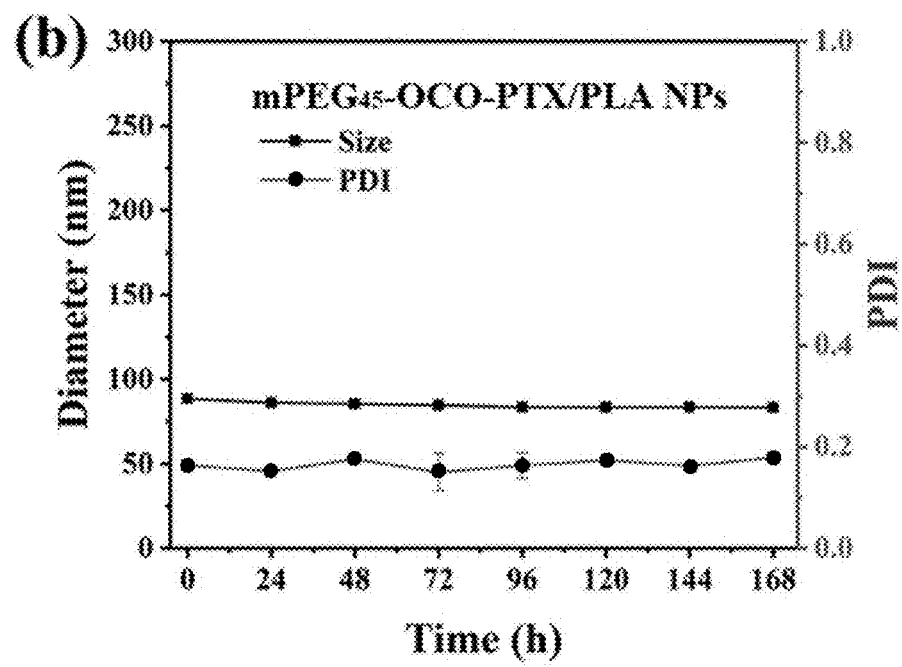
FIG. 6b depicts the stability results of mPEG$_{45}$-OCO-PTX/PLA nanoparticles in PBS solution at pH 7.4 and 37° C.

The stability results of mPEG$_{2k}$-OCO-PTX/PLA and mPEG$_{45}$-OCO-PTX/PLA are shown in FIG. 6. Within 7 days, the particle size and particle size distribution of the nanoparticles did not change, indicating that mPEG$_{2k}$-OCO-PTX/PLA and mPEG$_{45}$-OCO-PTX/PLA NPs have good stability in PBS (pH=7.4) at 37° C. This also indicates that PEG-carbonate-PTX/PLA nanoparticles, linked by carbonate bond between PEG and PTX, is superior to the ethyl ester bond between PEG and PTX, forming more stable nanoparticles in PBS solution.

Example 7. Stability Testing of mPEG-CH$_2$COO-PTX Micelles and mPEG-CH$_2$COO-PTX/PLA Nanoparticles in BSA Solution The stability of mPEG$_{2k}$-CH$_2$COO-PTX, mPEG$_{44}$-CH$_2$COO-PTX micelle solutions, and mPEG$_{2k}$-CH$_2$COO-PTX/PLA NPs, mPEG$_{44}$-CH$_2$COO-PTX/PLA NPs, mPEG$_{2k}$-OCO-PTX/PLA NPs, mPEG$_{45}$-OCO-PTX/PLA NPs in BSA solution was evaluated similarly to the procedure described in Example 6. Measurements of particle size and particle size distribution (PDI) were taken at specific intervals to assess the stability of the nanoparticles in the BSA solution.

Stability Testing of mPEG$_{2k}$-CH$_2$COO-PTX, mPEG$_{44}$-CH$_2$COO-PTX micelles in BSA Solution Take 3 mL of prepared mPEG$_{2k}$-CH$_2$COO-PTX, mPEG$_{44}$-CH$_2$COO-PTX micelle solutions, and mPEG$_{2k}$-CH$_2$COO-PTX/PLA, mPEG$_{44}$-CH$_2$COO-PTX/PLA, was added 2 mg of BSA per mL of micelle, or 10 mg of BSA per ml of nanoparticle solution, and mixed completely, and place in a 37° C. incubator. Measure the particle size at 0, 1, 2, 4, 8, and 12 hours and then every 12 hours for 7 days. Plot the particle size-time curves for the micelles and nanoparticles. The experimental results are shown in FIGS. 7 and 8.

Figure 7A:
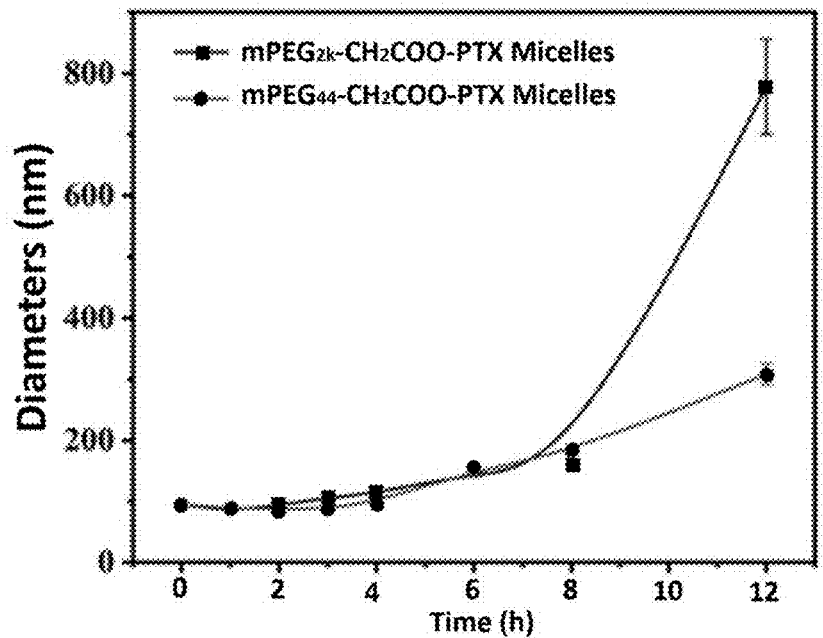
FIG. 7a depicts the stability of mPEG$_{2k}$-CH$_2$COO-PTX micelle and mPEG$_{44}$-CH$_2$COO-PTX micelles in 2 mg/mL BSA solutions.
Figure 7B:
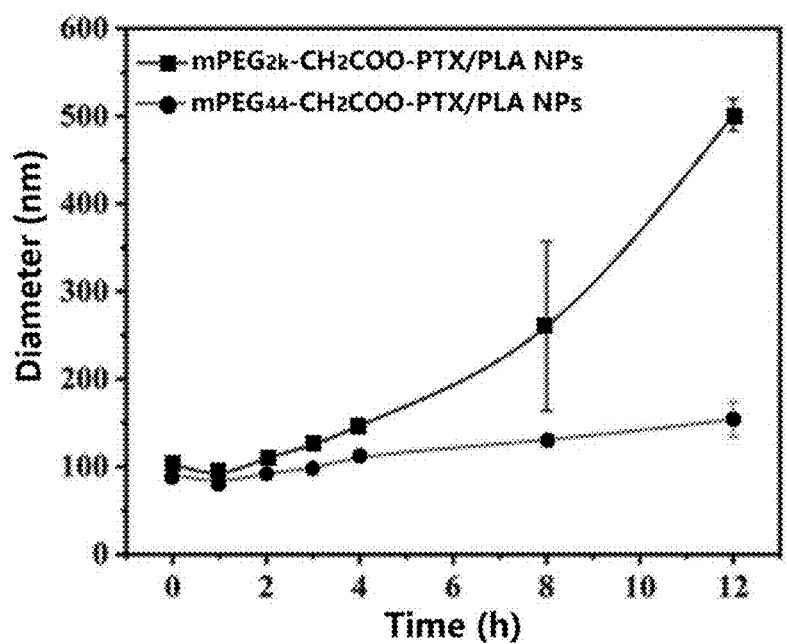
FIG. 7b depicts the stability of mPEG$_{2k}$-CH$_2$COO-PTX/PLA and mPEG$_{44}$-CH$_2$COO-PTX/PLA NPs in 10 mg/mL BSA solutions at 37° C.

In a 2 mg/ml BSA solution, the particle size of mPEG$_{2k}$-CH$_2$COO-PTX micelles begins to increase slowly after 2 hours and rapidly after 8 hours, indicating significant micelle aggregation upon BSA adsorption on the micelle surface. In contrast, the particle size of mPEG$_{44}$-CH$_2$COO-PTX micelles starts to change at 3 hours but increases slowly, indicating a less degree of micelle aggregation, as shown in FIG. 7a. For mPEG$_{2k}$-CH$_2$COO-PTX/PLA and mPEG$_{44}$-CH$_2$COO-PTX/PLA nanoparticles, the particle size has not changed for 24 hours, indicating PLA strengthens the hydrophobic interactions and thus, stabilizes the hydrophobic core. When BSA content increases from 2 mg/ml to 10 mg/ml, the particle size of mPEG$_{2k}$-CH$_2$COO-PTX/PLA NPs begins to increase after 1 hours and becomes five times the initial size by 12 hours, whereas the particle size of mPEG$_{44}$-CH$_2$COO-PTX/PLA nanoparticles increases after 2 hours and shows a slight change in particle size at 12 hours, as shown in FIG. 7b. This data indicate that mPEG$_{44}$-CH$_2$COO-PTX/PLA nanoparticles have greater stability in 10 mg/mL BSA solution compared to mPEG$_{2k}$-CH$_2$COO-PTX/PLA nanoparticles, demonstrating that the monodisperse PEG incorporated micelles and nanoparticles are more stable than their corresponding polydisperse counterparts.

Figure 8:
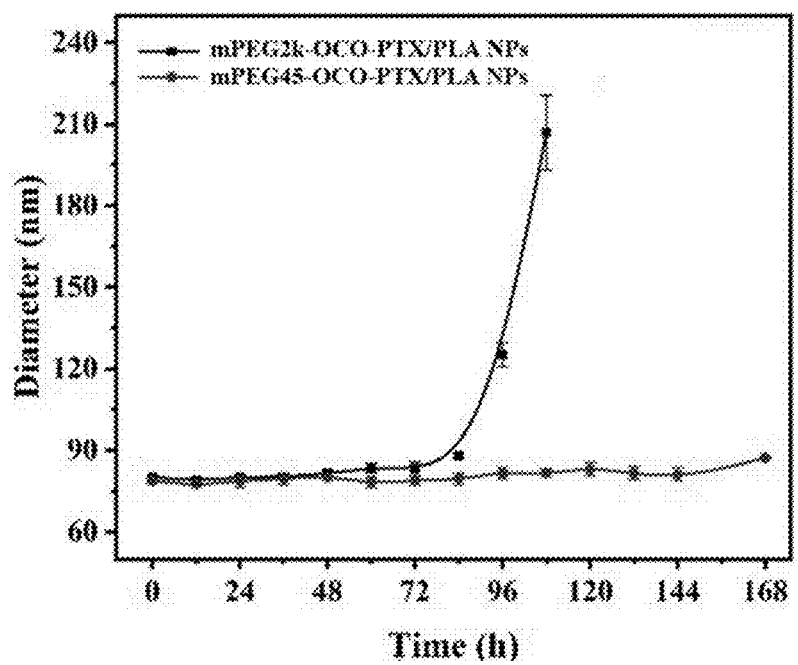
FIG. 8 depicts the stability of mPEG$_{2k}$-OCO-PTX/PLA and mPEG$_{45}$-OCO-PTX/PLA NPs in 10 mg/mL BSA solutions at 37° C.

The stability study of mPEG$_{2k}$-OCO-PTX/PLA and mPEG$_{45}$-OCO-PTX/PLA NPs in 10 mg/ml of BSA solution was also carried out using the same above method and the results are shown in FIG. 8. The particle size of mPEG$_{2k}$-OCO-PTX/PLA begins to increase after 84 hours and doubles the initial size by 108 hours, indicating BSA adsorption on surface and aggregation. In contrast, the particle size of mPEG$_{45}$-OCO-PTX/PLA nanoparticles remains unchanged for consecutive 7-days period (168 hours), further demonstrating their superior anti-BSA adsorption properties and enhanced stability. This stability of monodisperse mPEG$_{45}$-OCO-PTX/PLA nanoparticles is superior to that of polydisperse mPEG$_{2k}$-OCO-PTX/PLA NPs.

The stability data for PEG-L-PTX micelles and PEG-L-PTX/PLA nanoparticles are summarized in Table 2. The results show that the nanoparticles are more stable than the corresponding micelles, the carbonate bond of L is more stable than its ethyl ester bond and monodisperse PEG exhibits greater stability compared to polydisperse PEG in both micelles and nanoparticles.

Figure 9:
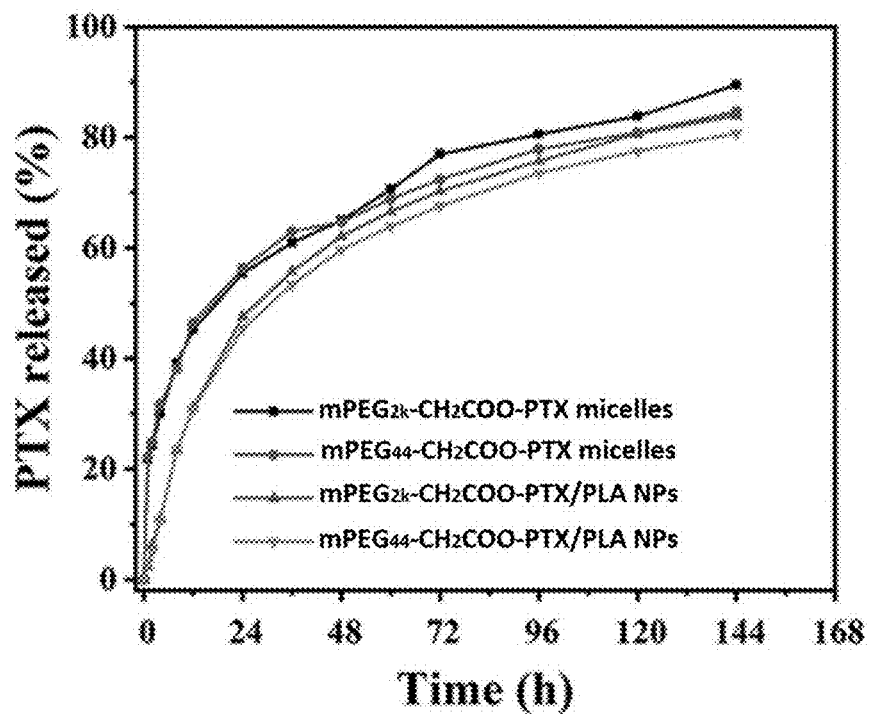
FIG. 9 is a plot of in vitro release of PTX from mPEG$_{2k}$-CH$_2$COO-PTX micelles, mPEG$_{44}$-CH$_2$COO-PTX micelles, mPEG$_{2k}$-CH$_2$COO-PTX/PLA NPs, and mPEG$_{44}$-CH$_2$COO-PTX/PLA NPs, respectively over time.

The release curves are shown in FIG. 9. At pH=7.4, in vitro release of PTX from mPEG$_{2k}$-CH$_2$COO-PTX micelles, mPEG$_{44}$-CH$_2$COO-PTX micelles, mPEG$_{2k}$-CH$_2$COO-PTX/PLA NPs, and mPEG$_{44}$-CH$_2$COO-PTX/PLA NPs are all demonstrated a similar PTX release pattern, but about 20% of PTX release in the first hour for the two micelles were observed. While for the two NPs samples, no burst release in the first hour was observed, preliminary due to the increased hydrophobic core stability provided by PLA.

Example 9: Synthesis of mPEG-L-G and Preparation of Nanoparticles, i.e., Synthesis of Monodisperse mPEG$_{23x2}$-Lysine-PTX and Preparation of Monodisperse mPEG$_{23x2}$-Lysine-PTX/PLA Nanoparticles Synthesis of Monodisperse mPEG$_{23x2}$-Lysine-PTX, as shown in FIG. 12

Following the same method as in Examples 1-4 to synthesize monodisperse mPEG$_{23x2}$-Lysine-COO-PTX. Briefly, 1.00 g (0.432 mmol) of monodisperse mPEG$_{23x2}$-Lysine, 0.41 g (0.475 mmol) of PTX was dissolved in 10 mL of DCM, then 0.12 g (0.647 mmol) of EDCI and 0.03 g (0.216 mmol) of DMAP was added and the reaction mixture was stirred magnetically at room temperature for 6 hours. After reaction, the mixture was diluted with 50 mL of DCM. The DCM phase was washed three times with 25 mL of water. The organic phase was dried with anhydrous MgSO$_4$, and then concentrated under reduced pressure. The crude product was recrystallized with EA, after filtration and vacuum drying, a white powder of the target compound (1.08 g, yield 83.1%) was obtained. A chromatograph purification may be necessary to obtain a high purity material.

TABLE 2

Stability data of PEG-L-PTX micelles and PEG-L-PTX/PLANPs in PBS and in BSA solutions at 37° C.

| Name | Type | L | PBS 37° C. | 2 mg/ml BSA solution | 10 mg/ml BSA solution |
|---|---|---|---|---|---|
| mPEG$_{2k}$-CH$_2$COO-PIX | Micelles | ethyl ester | <1 h | >2 h | / |
| mPEG$_{44}$-CH$_2$COO-PTX | Micelles | ethyl ester | <1 h | >3 h | / |
| mPEG$_{2k}$-CH$_2$COO-PTX/PLA | Nanoparticles | ethyl ester | ~2 h | 24 h < t < 36 h | >1 h |
| mPEG$_{44}$-CH$_2$COO-PTX/PLA | Nanoparticles | ethyl ester | ~4 h | 24 h < t < 36 h | >2 h |
| mPEG$_{2k}$-OCO-PTX | Micelles | carbonate | 12 h < t < 24 h | >12 | / |
| MPEG$_{45}$-OCO-PTX | Micelles | carbonate | 12 h < t < 24 h | 24 | / |
| mPEG$_{2k}$-OCO-PTX/PLA | Nanoparticles | carbonate | >7 days | >7 days | >84 h |
| MPEG$_{45}$-OCO-PTX/PLA | Nanoparticles | carbonate | >7 days | >7 days | >168 h |

Example 8: In Vitro Release Study of mPEG-L-PTX Micelles and mPEG-L-PTX/PLA Nanoparticles Prepare PBS buffer solutions with different pH values (pH=7.4, 5.0) and use them to prepare mPEG$_{2k}$-CH$_2$COO-PTX and mPEG$_{44}$-CH$_2$COO-PTX micelle solutions. Place the prepared micelle solutions in a 37° C. incubator and stir at 100 rpm. At 1, 2, 4, 8, 12, 24, 48, 60, 72, 84, 96, 120, 144, and 168 hours, take out 100 μL samples, add 900 μL of chromatographic acetonitrile, mix well, filter through a 0.45 μm membrane, and analyze 20 μL by HPLC. Calculate the PTX release percentage and plot the PTX release percentage-time curve.

The in vitro release experiments of mPEG$_{2k}$-CH$_2$COO-PTX/PLA, mPEG$_{44}$-CH$_2$COO-PTX/PLA, mPEG$_{2k}$-OCO-PTX/PLA, and mPEG$_{45}$-OCO-PTX/PLA nanoparticles follow the same procedure.

Figure 10A:
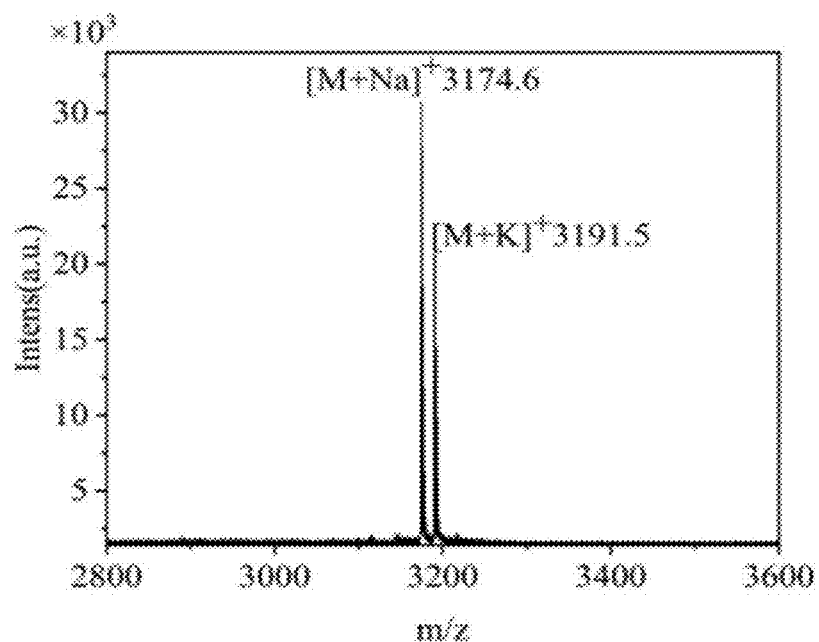
FIG. 10a is the MALDI-ToF mass spectrum of the branched mPEG$_{23x2}$-Lys-COO-PTX.

Mass Spectrum: The MALDI-ToF mass spectrum shows a molecular weight of 3152.3 Dalton, consistent with the calculated molecular weight of 3152.3 Dalton, as shown in FIG. 10(a).

Figure 10B:
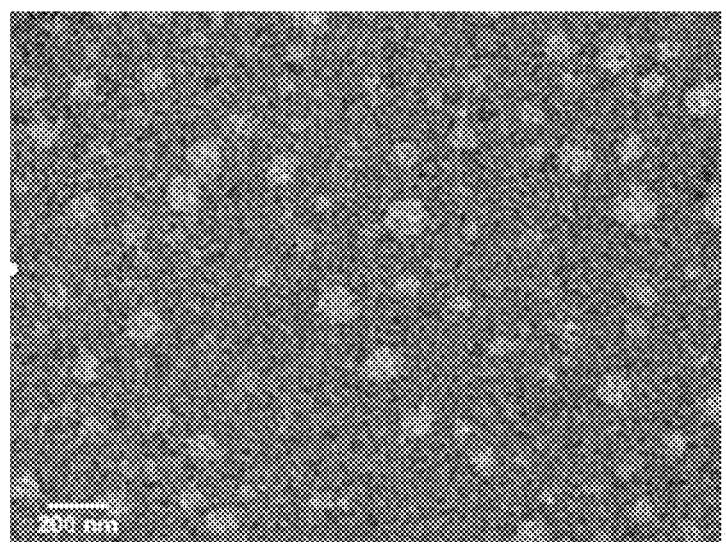
FIG. 10b is the TEM picture of spherical micelle morphology of the branched mPEG$_{23x2}$-Lys-COO-PTX, with the size in a range of 50-150 nm.

Characterization of Monodisperse mPEG$_{23x2}$-Lysine-PTX Micelles: DLS measurements show that the micelle particle size is approximately 75.6 nm, consistent with the range observed by TEM, which is in the range of 50~150 nm, as shown in FIG. 10(b).

Preparation of Monodisperse mPEG$_{23x2}$-Lysine-PTX/PLA Nanoparticles

The preparation method is the same as described for the nanoparticles in Example 1.

Example 10: Pharmacokinetic Study of mPEG-CH$_2$COO-PTX Micelles and mPEG-CH$_2$COO-PTX/PLA Nanoparticles All mice (45 in total) were fasted for over 12 hours before administration. The mice were evenly divided into 5 groups and received tail vein injections of mPEG$_{2k}$-CH$_2$COO-PTX micelles, mPEG$_{44}$-CH$_2$COO-PTX micelles, mPEG$_{2k}$-CH$_2$COO-PTX/PLA nanoparticles, mPEG$_{44}$-CH$_2$COO-PTX/PLA nanoparticles, and mPEG$_{23\times2}$-Lysine-PTX/PLA nanoparticles (all with a free PTX content of 10 mg/kg). Blood samples (100 μL) were collected from the orbital plexus at 0.083, 0.25, 0.5, 1, 2, 4, 8, 10, and 24 hours post-injection. The blood was placed in EDTA-K2 anticoagulant tubes, mixed well by inverting several times, and stored on wet ice. The samples were centrifuged at 13,000 rpm for 10 minutes to separate the plasma, which was then stored at −40° C.

Sample Processing Before Testing:

The plasma samples were incubated at 37° C. for 3 hours to hydrolyze mPEG-CH$_2$COO-PTX into PTX, which was then detected using LC-MS.

Figure 11:
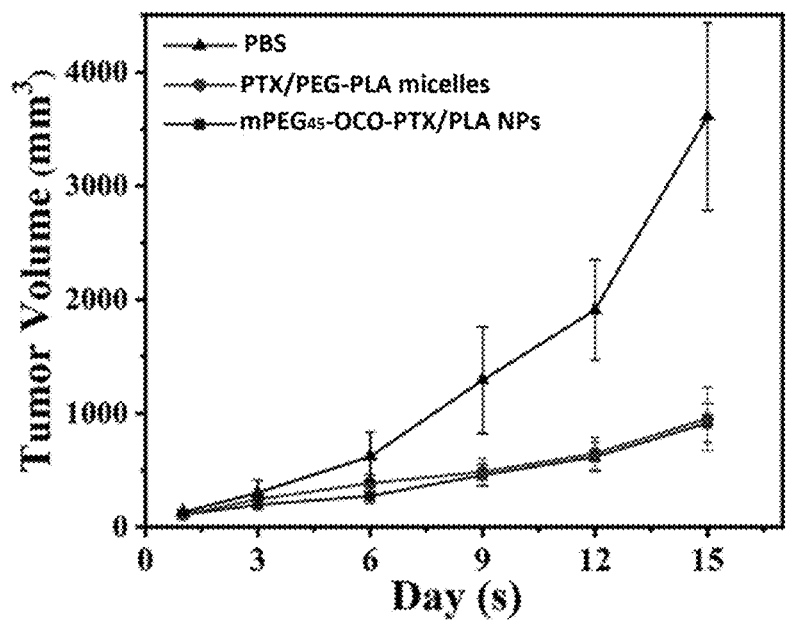
FIG. 11 is a plot of the tumor volume growth of 4T1 bearing mice over time when compared mPEG$_{45}$-OCO-PTX/PLA NPs with commercially available polymeric PTX/mPEG$_{2k}$-PLA micellar formulation.

Drug Concentration-Time Curve:

The drug concentration-time curves are shown in FIG. 11, and the pharmacokinetic parameter PTX half-life ($t_{1/2}$) in mice blood is listed in Table 3. The half-lives ($t_{1/2}$) of mPEG$_{2k}$-CH$_2$COO-PTX micelles, mPEG$_{44}$-CH$_2$COO-PTX micelles, mPEG$_{2k}$-CH$_2$COO-PTX/PLA nanoparticles, mPEG$_{44}$-CH$_2$COO-PTX/PLA nanoparticles, and mPEG$_{23\times2}$-Lysine-PTX/PLA nanoparticles are 4.0±0.66, 5.4±0.66, 5.2±0.62, and 6.7±0.64, 7.5±1.4 hours, respectively. The half-life of monodisperse mPEG$_{44}$-CH$_2$COO-PTX micelles is greater than that of polydisperse mPEG$_{2k}$-CH$_2$COO-PTX micelles, and the half-life of monodisperse mPEG$_{44}$-CH$_2$COO-PTX/PLA nanoparticles is greater than that of mPEG$_{2k}$-CH$_2$COO-PTX/PLA nanoparticles. This indicates that micelles and nanoparticles prepared with monodisperse PEG exhibit longer circulation times in mice than those prepared with polydisperse PEG. The half-lives of nanoparticles are greater than those of their corresponding micelles, suggesting that the addition of PLA extends the circulation time of the micelles in vivo.

TABLE 3

Pharmacokinetic half-lives of mPEG$_{2k}$-CH$_2$COO-PTX Micelles, MPEG$_{44}$-CH$_2$COO-PTX Micelles, mPEG$_{2k}$-CH$_2$COO-PTX/PLA Nanoparticles, mPEG$_{44}$-CH$_2$COO-PTX/PLA Nanoparticles, and mPEG$_{23\times2}$-Lysine-PTX/PLA Nanoparticles

| Entry | Composition | Form | $t_{1/2}$ (h) |
|---|---|---|---|
| 1 | mPEG$_{2k}$-CH$_2$COO-PTX | Micelles | 4.0 ± 0.66 |
| 2 | mPEG$_{44}$-CH$_2$COO-PTX | Micelles | 5.4 ± 0.66 |
| 3 | mPEG$_{2k}$-CH$_2$COO-PTX/PLA | Nanoparticles | 5.2 ± 0.62 |
| 4 | mPEG$_{44}$-CH$_2$COO-PTX/PLA | Nanoparticles | 6.4 ± 0.64 |
| 5 | Branched mPEG$_{23\times2}$-Lys-PTX/PLA | Nanoparticles | 7.5 ± 1.4 |

Example 11: In Vivo Antitumor Study of mPEG-OCO-PTX/PLA Nanoparticles

Female Balb/c mice aged 4-6 weeks, weighing approximately 20 g, were inoculated with 4T1 cells (1×10$^6$ cells/mouse) in the armpit. Tumor growth and the animals' status were regularly monitored after injection. When the tumor volume reached approximately 100 mm$^3$, the mice were randomly divided into three groups, each with six mice. The groups received the following treatments via tail vein injection: mPEG$_{45}$-OCO-PTX/PLA (PTX 10 mg/kg), the approved mPEG-PLA/PTX nanoformulation as a positive control (PTX 10 mg/kg), and PBS (pH=7.4) as a negative control. The first injection was considered day 1, followed by injections on days 4, 7, 10, and 13. Tumor size in the armpit was measured every three days, and tumor volume was calculated using the formula V=L x W$^2$/2.

Tumor Volume Growth:

At the end of the experiment, the average tumor volumes in the PBS group, mPEG$_{45}$-OCO-PTX/PLA NPs group, and mPEG$_{2k}$-PLA/PTX nanoformulation group were 3609.33±825.32 mm$^3$, 916.47±168.77 mm$^3$, and 953.24±277.6 mm$^3$, respectively. The antitumor activity of mPEG$_{45}$-OCO-PTX was slightly better than, or at least equivalent to, the positive control.

Body Weight Change

The body weight of tumor-bearing mice in the mPEG$_{45}$-OCO-PTX and positive control groups were 22.36±1.35 g and 22.96±1.13 g, respectively, at the end of the experiment. Both groups maintained a stable body weight during the experiment.

No mice died during the 15-day experiment.

Example 12. Synthesis of mPEG-L-G(SN38) and Preparation of Nanoparticles: Synthesis of Polydisperse mPEG$_{2k}$-CH$_2$CONHCH$_2$CH$_2$—SS—CH$_2$CH$_2$COO—SN38 and Preparation of mPEG$_{2k}$-CH$_2$CONHCH$_2$CH$_2$—SS—CH$_2$CH$_2$COO—SN38/PLA Nanoparticles The tumor microenvironment is usually reductive, and tumor cells produce high levels of reductive molecules, such as glutathione (GSH). By utilizing the reduction response of disulfide bonds in the GSH environment, these bonds can be cleaved in specific environments to release anticancer drugs, reducing side effects on normal tissues and achieving targeted drug delivery. Using the starting material mPEG$_{2k}$-CH$_2$CONH—CH$_2$CH$_2$—S—S—CH$_2$CH$_2$COOH (mPEG$_{2k}$-SS—COOH, mPEG$_{2k}$-L) containing disulfide bond, mPEG$_{2k}$-SS—COO—SN38 ester was synthesized with the hydrophobic anticancer drug SN38 linked, as illustrated in Scheme 3.

Synthesis Method: Identical to Example 1

Figure 12A:
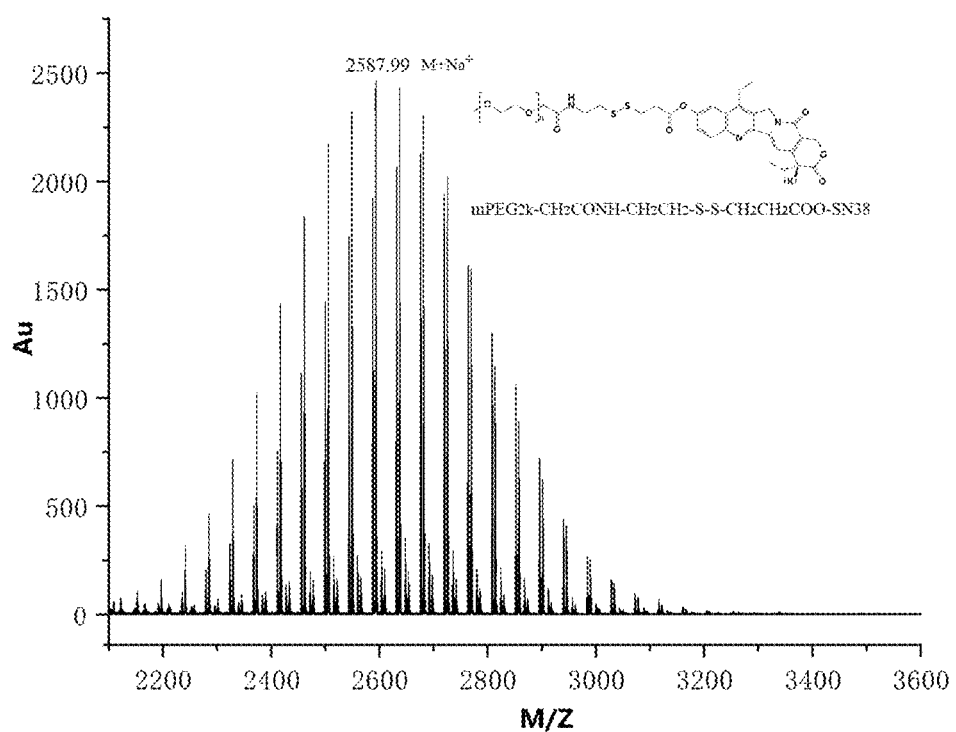
FIG. 12a is the MALDI-ToF spectrum of polydisperse mPEG$_{2k}$-CH$_2$CONH—SS—CH$_2$CH$_2$COO—SN38
Figure 12B:
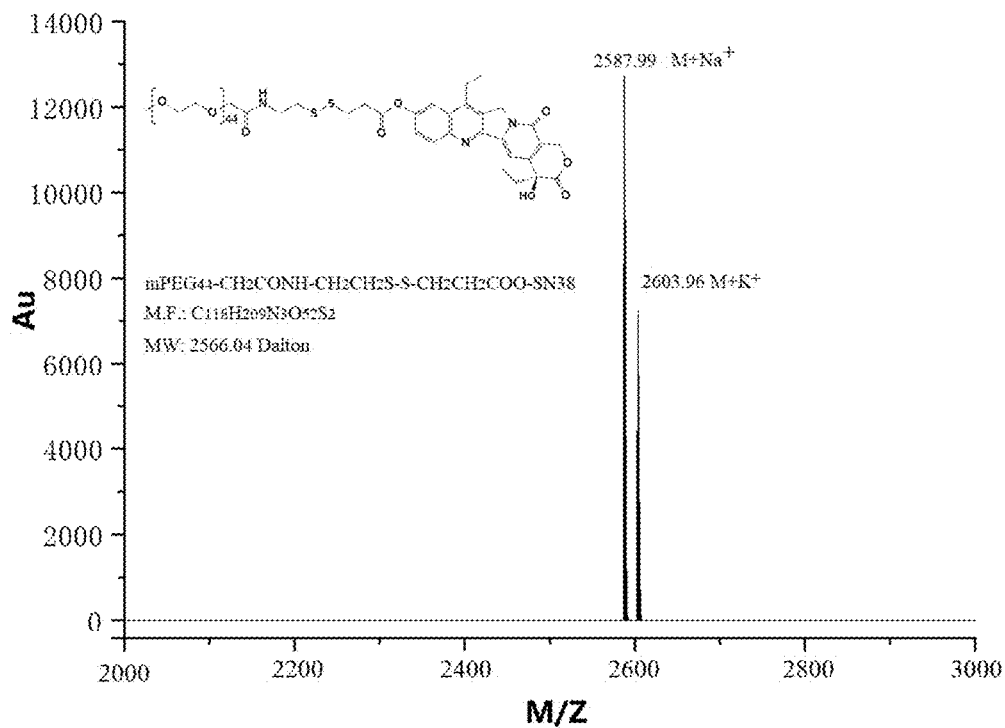
FIG. 12b is the MALDI-ToF spectrum of monodisperse mPEG$_{44}$-CH$_2$CONH—SS—CH$_2$CH$_2$COO—SN38.
Figure 13A:
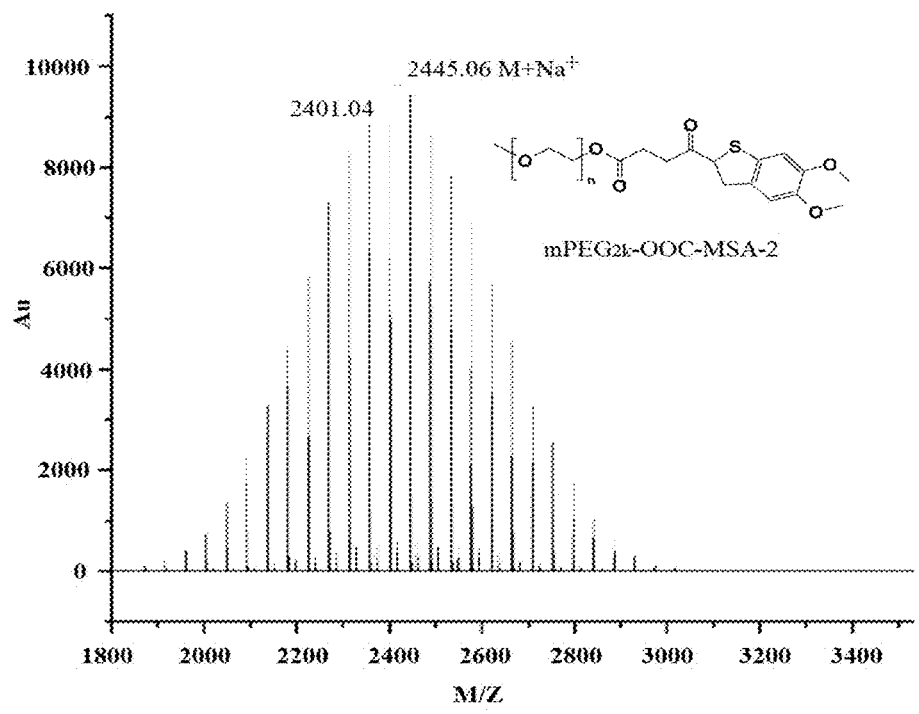
FIG. 13a is the MALDI-ToF spectrum of mPEG$_{2k}$-O(O=C)-MSA-2.
Figure 13B:
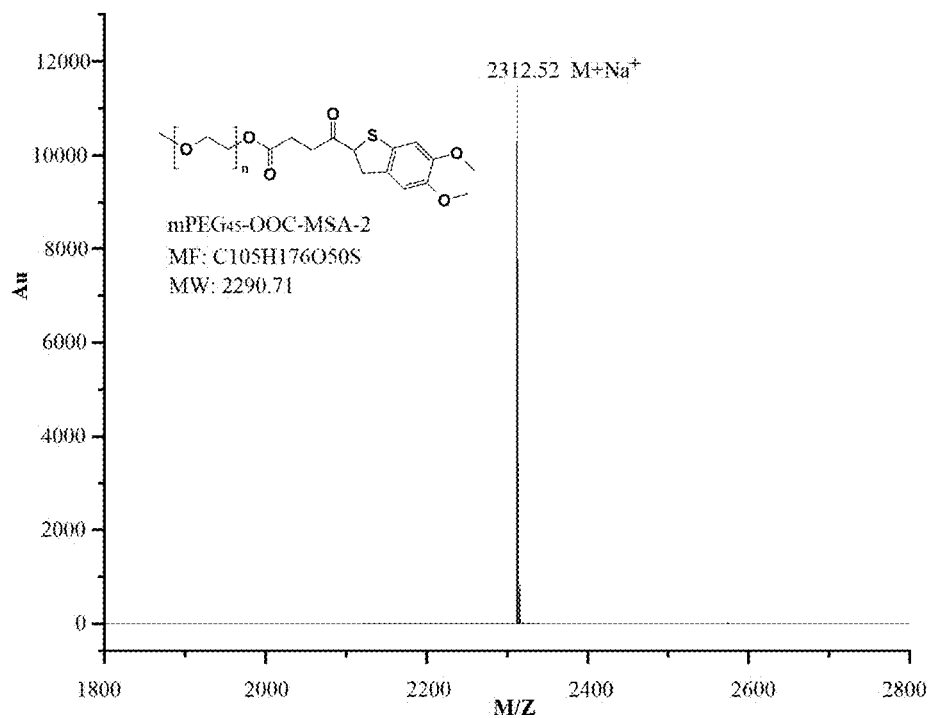
FIG. 13b is the MALDI-ToF spectrum of mPEG$_{45}$-O(O=C)-MSA-2.
Figure 13C:
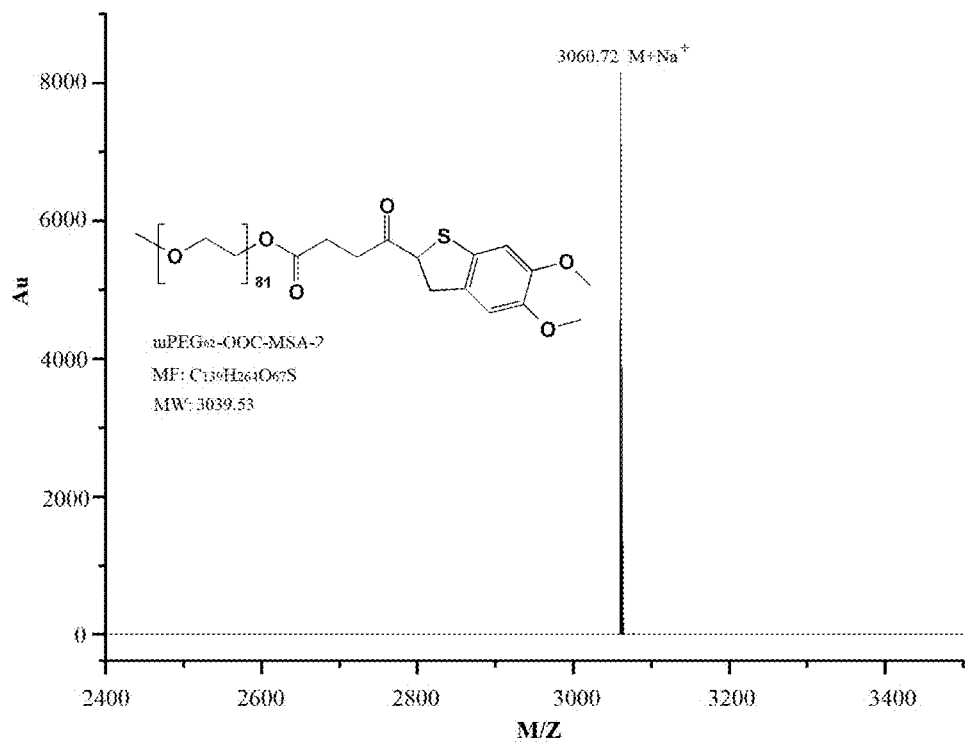
FIG. 13c is the MALDI-ToF spectrum of mPEG$_{62}$-O(O=C)-MSA-2.
Figure 13D:
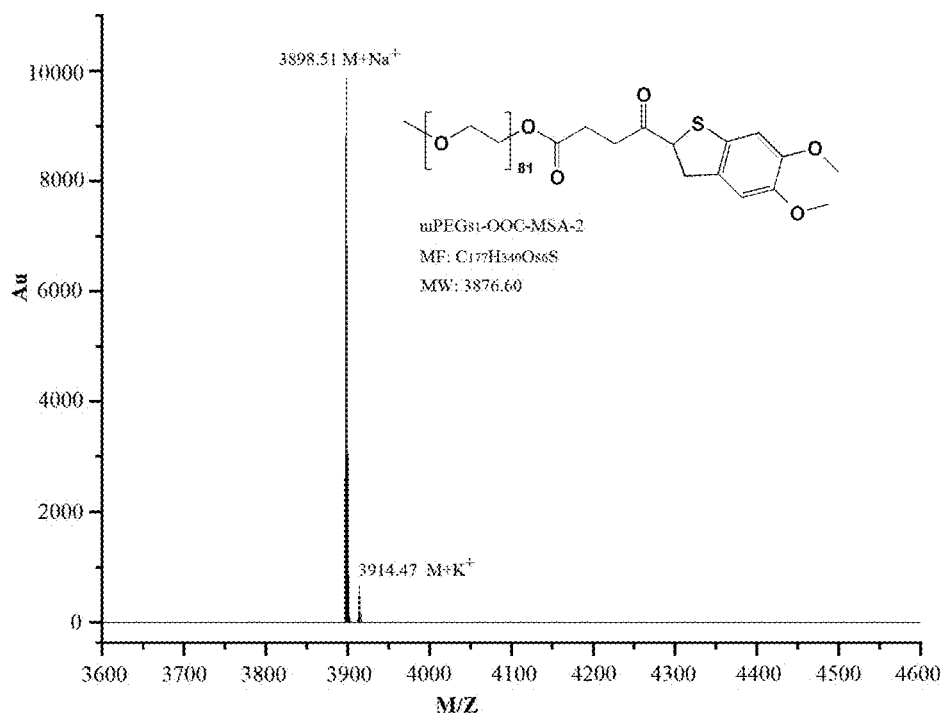
FIG. 13d is the MALDI-ToF spectrum of mPEG$_{81}$-O(O=C)-MSA-2.

The compound was characterized by MALDI-ToF mass spectrometry, and its mass spectrum is shown in FIG. 12a.

Preparation of mPEG$_{2k}$-CH$_2$CONH—SS—CH$_2$CH$_2$COO—SN38/PLA Nanoparticles

The preparation method is the same as described for the nanoparticles in Example 1.

Example 13. Synthesis of mPEG-L-G(SN38) and Preparation of Nanoparticles, i.e., Synthesis of Monodisperse mPEG$_{44}$-CH$_2$CONHCH$_2$CH$_2$—SS—CH$_2$CH$_2$COO—SN38 and Preparation of mPEG$_{44}$-CH$_2$CONHCH$_2$CH$_2$—SS—CH$_2$CH$_2$COO—SN38/PLA Nanoparticles The synthetic procedure is identical to Example 12. The mass spectrum shows [M+Na$^+$] at 2587.99 Dalton, [M+K$^+$] at 2603.96 Dalton, and the actual measured value M is 2565.0 Dalton, which is consistent with the theoretical value of 2566.04 Dalton.

Preparation of mPEG$_{2k}$-CH$_2$CONHCH$_2$CH$_2$—SS—CH$_2$CH$_2$COO—SN38/PLA Nanoparticles The preparation method is the same as described for the nanoparticles in Example 12.

Example 14. Pharmacokinetic Study of mPEG$_{2k}$-CH$_2$CONHCH$_2$CH$_2$—SS—CH$_2$CH$_2$COO—SN38 Micelles, mPEG$_{44}$-CH$_2$CONHCH$_2$CH$_2$—SS—CH$_2$CH$_2$COO—SN38 Micelles, mPEG$_{2k}$-CH$_2$CONHCH$_2$CH$_2$—SS—CH$_2$CH$_2$COO—SN38/PLA Nanoparticles, and mPEG$_{44}$-CH$_2$CONHCH$_2$CH$_2$—SS—CH$_2$CH$_2$COO—SN38/PLA Nanoparticles The pharmacokinetic study was conducted using the same method as in Example 10, and the results are shown in Table 4.

TABLE 4

Pharmacokinetic Study of mPEG$_{2k}$-CH$_2$CONH-CH$_2$CH$_2$-SS-CH$_2$CH$_2$COO-SN38 Micelles, mPEG$_{44}$-CH$_2$CONH-CH$_2$CH$_2$-SS-CH$_2$CH$_2$COO-SN38 Micelles, mPEG$_{2k}$-CH$_2$CONH-CH$_2$CH$_2$-SS-CH$_2$CH$_2$COO-SN38/PLA Nanoparticles, and mPEG$_{44}$-CH$_2$CONH-CH$_2$CH$_2$-SS-CH$_2$CH$_2$COO-SN38/PLA Nanoparticles.

| | Name | Type | $t_{1/2}$ (h) |
|---|---|---|---|
| 1 | mPEG$_{2k}$-CH$_2$CONHCH$_2$CH$_2$-SS-CH$_2$CH$_2$COO-SN38 | Micelles | 3.64 |
| 2 | mPEG$_{44}$-CH$_2$CONHCH$_2$CH$_2$-SS-CH$_2$CH$_2$COO-SN38 | Micelles | 3.88 |
| 3 | mPEG$_{2k}$-CH$_2$CONHCH$_2$CH$_2$-SS-CH$_2$CH$_2$COO-SN38/PLA | Nanoparticles | 3.83 |
| 4 | mPEG$_{44}$-CH$_2$CONHCH$_2$CH$_2$-SS-CH$_2$CH$_2$COO-SN38/PLA | Nanoparticles | 4.92 |

From Table 4, it can be observed that the half-life of monodisperse mPEG$_{44}$-CH$_2$CONH—CH$_2$CH$_2$—SS—CH$_2$CH$_2$COO—SN38 micelles (3.88 h) is slightly longer than that of mPEG$_{2k}$-CH$_2$CONH—CH$_2$CH$_2$—SS—CH$_2$CH$_2$COO—SN38 micelles (3.64 h). The half-life of monodisperse mPEG$_{44}$CH$_2$CONH—CH$_2$CH$_2$—SS—CH$_2$CH$_2$COO—SN38/PLA nanoparticles (4.92 h) is longer than that of polydisperse mPEG$_{2k}$-CH$_2$CONH—CH$_2$CH$_2$—SS—CH$_2$CH$_2$COO—SN38/PLA nanoparticles (3.83 h). Additionally, the half-life of nanoparticles (4.92 h and 3.83 h) is longer than that of the corresponding micelles (3.88 h and 3.64 h). The data from the table allow us to conclude that the $t_{1/2}$ of nanoparticles is longer than that of the corresponding micelles. Therefore, the addition of PLA makes the nanoparticle hydrophobic core more stable in vitro and also in vivo.

Example 15. Synthesis of mPEG-L-G(TPE) and Preparation of Nanoparticles, i.e., Synthesis of Polydisperse mPEG$_{2k}$-CH$_2$CONH-tetraphenyl ethylene (TPE) and Preparation of mPEG$_{2k}$-CH$_2$CONH-TPE/PLA Luminescent Particles Synthesis of mPEG$_{2k}$-CH$_2$CONH-TPE 2.00 g (1.05 mmol) of mPEG$_{2k}$-CH$_2$COOH, 0.33 g (0.96 mmol) of TPE-NH$_2$, 56.70 mg (0.464 mmol) of DMAP was dissolved in 25 ml of DCM, then 262.30 mg (1.37 mmol) of EDC-HCl was added under stirring at room temperature. After the reaction, add an appropriate amount of DCM to dilute the reaction mixture, wash away impurities with water, dry the organic phase with MgSO$_4$, and concentrate under reduced pressure. Add 20 mL of EA and place at −18° C. for recrystallization to obtain a white powder of mPEG$_{2k}$-CH$_2$CONH-TPE (1.65 g, yield 71%).

Preparation of mPEG$_{2k}$-CH$_2$CONH-TPE/PLA Particles

TPE exhibits aggregation-induced emission characteristics, meaning it does not emit light in solution but emits green or sky-blue fluorescence upon UV light when in an aggregated state. When mPEG$_{2k}$-CH$_2$CONH-TPE is dissolved in aqueous solution to form micelles, the hydrophobic TPE aggregates, and under UV irradiation, the solution appears sky blue. Upon further dilution, until no fluorescence is observed under UV irradiation, it indicates that mPEG$_{2k}$-CH$_2$CONH-TPE is no longer in an aggregated state. Then, by adding PLA's ethyl acetate solution to the diluted solution and evaporating the solvent, precipitated particles are obtained. These particles exhibit strong fluorescence under UV irradiation. This indicates that TPE and PLA form a hydrophobic core, which significantly increases the local concentration of TPE and restricts its rotation, resulting in strong fluorescence. Due to the extremely low content of mPEG$_{2k}$-CH$_2$CONH-TPE, it is insufficient to emulsify PLA into nanoparticles. This also indicates that the encapsulation efficiency of TPE within PEG-CH$_2$CONH-TPE/PLA particles is high.

Preparation of mPEG$_{2k}$-CH$_2$CONH-TPE/PLA Nanoparticles

The preparation method is the same as described for the nanoparticles in Example 1.

Example 16. Synthesis of mPEG-L-G(MSA-2) and Preparation of Nanoparticles, i.e., Synthesis of Polydisperse mPEG$_{2k}$-O(O═C)-MSA-2 and Preparation of mPEG$_{2k}$-O(O═C)-MSA-2/PLA Nanoparticles Synthesis of Polydisperse mPEG$_{2k}$-O(O═C)-MSA-2 mPEG$_{2k}$-OH (2.00 g, 1.05 mmol), MSA-2 (294 mg, 1.0 mmol), EDC-HCl (262.30 mg, 1.37 mmol), and DMAP (56.70 mg, 0.464 mmol) were dissolved in 20 ml of DCM and the mixture was stirred at room temperature for 12 hours. After the reaction was complete, 30 ml of DCM was added, the DCM phase was washed with water to remove impurities, was dried with MgSO4, and then concentrated under reduced pressure. 20 mL of EA was added and the flask was placed at a −18° C. freezer for recrystallization, resulting in a white powder of mPEG$_{2k}$-O(O═C)-MSA-2 (1.65 g, yield 75%).

MALDI-TOF-MS: Due to polydispersity of mPEG$_{2k}$-OH, the mass spectrum displays a series of mPEGn-O(O═C)-MSA-2 with various molecular weights, showing peaks differing by 44.01 in molecular weight. Observed mass spectrum peaks [M+Na]$^+$=2401.04 and 2445.06 correspond to mPEG with polymerization degrees of n=47 and 48, respectively, as shown in FIG. 13 (a).

Preparation of mPEG$_{2k}$-O(O=C)-MSA-2/PLA Nanoparticles

The nanoparticles were prepared using the same method as described in Example 1.

Example 17. Synthesis of mPEG-L-G(MSA-2) and Preparation of Nanoparticles, i.e., Synthesis of Monodisperse mPEG$_{45}$-O(O=C)-MSA-2 and Preparation of mPEG$_{45}$-O(O=C)-MSA-2/PLA Nanoparticles The monodisperse mPEG$_{45}$-O(O=C)-MSA-2 and mPEG$_{45}$-O(O=C)-MSA-2/PLA nanoparticles were prepared using the same method as in Example 16.

MALDI-TOF-MS: The MALDI-ToF mass spectrum (FIG. 13 (b)) shows a single molecular ion peak, [M+Na$^+$]=2312.52 Dalton, measured consistent with the theoretical molecular weight [M+Na$^+$]=2312.52 Dalton.

Preparation of mPEG$_{45}$-O(O=C)-MSA-2/PLA Nanoparticles

The nanoparticles were prepared using the same method as described in Example 16.

Example 18. Synthesis of mPEG-L-G(MSA-2) and Preparation of Nanoparticles, i.e., Synthesis of Monodisperse mPEG$_{62}$-O(O=C)-MSA-2 and Preparation of mPEG$_{62}$-O(O=C)-MSA-2/PLA Nanoparticles The monodisperse mPEG$_{62}$-O(O=C)-MSA-2 and mPEG$_{62}$-O(O=C)-MSA-2/PLA nanoparticles were prepared using the same method as in Example 16.

MALDI-TOF-MS. The MALDI-ToF mass spectrum (FIG. 13 (c)) shows a single molecular ion peak, [M+Na$^+$]=3060.72 Dalton, the calculated [M+Na$^+$] is 3061.2 Dalton.

Preparation of mPEG$_{62}$-O(O=C)-MSA-2/PLA Nanoparticles

The nanoparticles were prepared using the same method as described in Example 16.

Example 19. Synthesis of mPEG-L-G(MSA-2) and Preparation of Nanoparticles, i.e., Synthesis of Monodisperse mPEG$_{81}$-O(O=C)-MSA-2 and Preparation of mPEG$_{81}$-O(O=C)-MSA-2/PLA Nanoparticles The monodisperse mPEG$_{81}$-O(O=C)-MSA-2 and mPEG$_{81}$-O(O=C)-MSA-2/PLA nanoparticles were prepared using the same method as in Example 16.

MALDI-TOF-MS: The MALDI-ToF mass spectrum (FIG. 13(d)) shows a single molecular ion peak, [M+Na$^+$]=3898.51 Dalton, and [M+K$^+$]=3914.47 Dalton, the calculated [M+Na$^+$] is 3899.40 Dalton.

Preparation of mPEG$_{81}$-O(O=C)-MSA-2/PLA Nanoparticles

The nanoparticles were prepared using the same method as described in Example 16.

Example 20. Pharmacokinetic Study of mPEG$_{45}$-O(O=C)-MSA-2 Micelles, and mPEG$_{45}$-O(O=C)-MSA-2/PLA, mPEG$_{62}$-O(O=C)-MSA-2/PLA, mPEG$_{81}$-O(O=C)-MSA-2/PLA Nanoparticles The pharmacokinetic study was conducted using the same method as in Example 10 and Example 14, and the results are shown in Table 5.

TABLE 5

Pharmacokinetic study of mPEG$_{45}$-O(O=C)-MSA-2 micelles, and mPEG$_{45}$-O(O=C)-MSA-2/PLA, mPEG$_{62}$-O(O=C)-MSA-2/PLA, mPEG$_{81}$-O(O=C)-MSA-2/PLA nanoparticles.

|   | Name | Type | $t_{1/2}$ (h) |
|---|---|---|---|
| 1 | mPEG$_{45}$-O(O=C)-MSA-2 | Micelles | 1.15 |
| 2 | mPEG$_{45}$-O(O=C)-MSA-2/PLA | Nanoparticles | 1.27 |
| 3 | mPEG$_{62}$-O(O=C)-MSA-2/PLA | Nanoparticles | 1.36 |
| 4 | mPEG$_{81}$-O(O=C)-MSA-2/PLA | Nanoparticles | 3.09 |

From Table 5, the half-life of mPEG$_{45}$-O(O=C)-MSA-2/PLA nanoparticles in mice blood (1.27 h) is a slightly longer than that of mPEG$_{45}$-O(O=C)-MSA-2 micelles (1.15 h). As the PEGn repeat unit n increases from 45 to 62 and to 81, the half-life of mPEGn-O(O=C)-MSA-2/PLA nanoparticles in mice increases from 1.27 h to 1.36 h and to 3.09 h, respectively.

Comparing the three kinds of micelles of mPEG$_{45}$-L-G (PTX, SN38 and MSA-2, with respective MW of 853.9, 392.4, and 294.2 Dalton) investigated, where the linking bond is an ester bond, the blood circulation half-lives ($t_{1/2}$) of mPEG$_{44}$-CH$_2$COO-PTX, mPEG$_{44}$-CH$_2$CONH—CH$_2$CH$_2$—SS—CH$_2$CH$_2$COO—SN38, and mPEG$_{45}$-O(O=C)-MSA-2 in mice decrease in that order with decreasing MW. For the three nanoparticles mPEG$_{44}$-CH$_2$COO-PTX/PLA, mPEG$_{44}$-CH$_2$CONHCH$_2$CH$_2$SS—CH$_2$CH$_2$COO—SN38/PLA, and mPEG$_{45}$-O(O=C)-MSA-2/PLA, their $t_{1/2}$ also decreases, as shown in Table 6.

TABLE 6

Effects of drug molecular weight and PLA on blood circulation half-life ($t_{1/2}$) in mice

| G | PTX | SN38 | MSA-2 |
|---|---|---|---|
| MW | 853.9 | 392.4 | 294.2 |
| Micelles | mPEG$_{44}$-CH$_2$COO-PTX | mPEG$_{44}$-SS-COO-SN38 | mPEG$_{45}$-OOC-MSA-2 |
| $t_{1/2}$ (h) | 5.4 | 3.38 | 1.15 |
| NPs | mPEG$_{44}$-CH$_2$COO-PTX/PLA | mPEG$_{44}$-SS-COO-SN38/PLA | mPEG$_{45}$-OOC-MSA-2/PLA |
| $t_{1/2}$ (h) | 6.7 | 4.92 | 1.27 |

The half-life of the micelles seems related to the molecular weight of the hydrophobic compound G; the larger the molecular weight of G, the stronger the interaction within the hydrophobic core of the micelles, and the longer the blood circulation half-life in mice. After adding PLA, the NPs' blood circulation half-life is also longer than that of the corresponding micelles (without PLA).

Example 21. Preparation of Dual-Component (mPEG$_{80}$-CH$_2$COO-PTX and mPEG$_{80}$-SS—SN38)/PLA NPs After mixing 20 mg of mPEG$_{80}$-CH$_2$COO-PTX and 20 mg of mPEG$_{80}$-CH$_2$CONHCH$_2$CH$_2$SS—CH$_2$CH$_2$COO—SN38 (w/w=1/1), the dual-component (mPEGgo-CH$_2$COO-PTX and mPEG$_{80}$-CH$_2$CONHCH$_2$CH$_2$—SS—CH$_2$CH$_2$COO—SN38)/PLA nanoparticles were prepared using the method described in Example 1.

Example 22. Preparation of Dual-Component (mPEG$_{80}$-CH$_2$COO-PTX and mPEG$_{81}$-O(O=C)-MSA-2)/PLA NPs After mixing 20 mg of mPEG$_{80}$-CH$_2$COO-PTX and 20 mg of mPEG$_{81}$-O(O=C)-MSA-2 (w/w=1/1), the dual-component (mPEG$_{80}$-CH$_2$COO-PTX and mPEG$_{81}$-O(O=C)-MSA-2)/PLA nanoparticles were prepared using the method described in Example 1.

Example 23. Preparation of Dual-Component (mPEG$_{80}$-CH$_2$CONHCH$_2$CH$_2$—SS—CH$_2$CH$_2$COO—SN38 and mPEG$_{81}$-O(O=C)-MSA-2)/PLA NPs After mixing 20 mg of mPEG$_{80}$-CH$_2$CONHCH$_2$CH$_2$—SS—CH$_2$CH$_2$COO—SN38 and 20 mg of mPEG$_{81}$-O(O=C)-MSA-2 (w/w=1/1), the dual-component (mPEG$_{80}$-CH$_2$CONHCH$_2$CH$_2$—SS—CH$_2$CH$_2$COO—SN38 and mPEG$_{81}$-O(O=C)-MSA-2)/PLA nanoparticles were prepared using the method described in Example 1.

Example 24. Synthesis of mPEG-L-G(MSA-2) and Preparation of Nanoparticles, i.e., Synthesis of Monodisperse mPEG$_{44}$-CH$_2$CONH—CH$_2$CH$_2$—SS—CH$_2$CH$_2$O(O=C)-MSA-2 ester and Preparation of mPEG$_{44}$-CH$_2$CONH—CH$_2$CH$_2$—SS—CH$_2$CH$_2$O(O=C)-MSA-2 ester/PLA Nanoparticles The monodisperse mPEG$_{44}$-CH$_2$CONH—CH$_2$CH$_2$—SS—CH$_2$CH$_2$O(O=C)-MSA-2 ester was synthesized and mPEG$_{44}$-CH$_2$CONH—CH$_2$CH$_2$—SS—CH$_2$CH$_2$O(O=C)-MSA-2/PLA nanoparticles were prepared using the same method as in Example 16.

Figure 14:
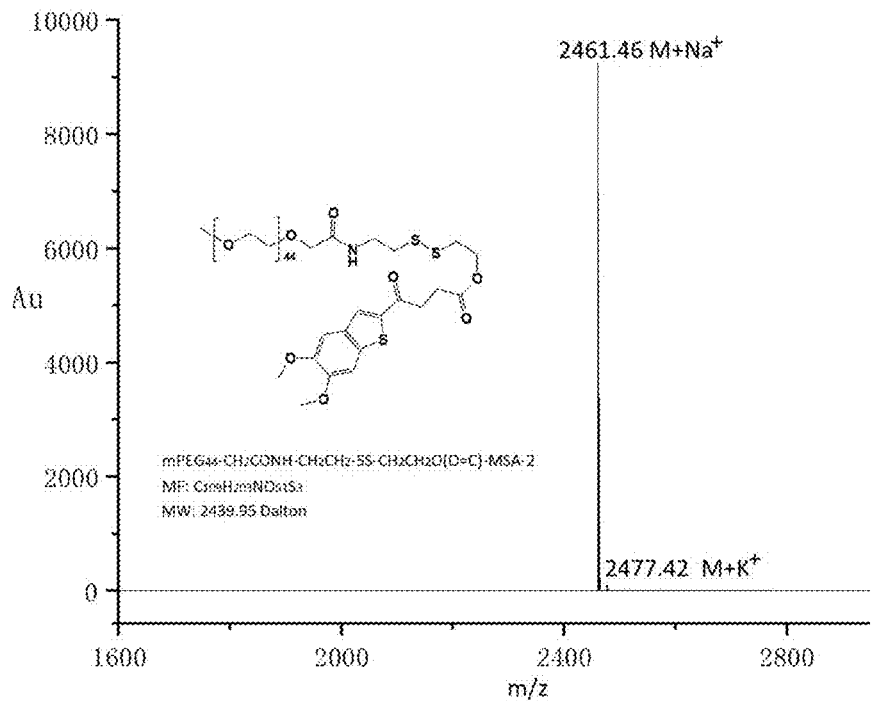
FIG. 14. The MALDI-ToF spectrum of mPEG$_{44}$-CH$_2$CONH—CH$_2$CH$_2$—SS—CH$_2$CH$_2$O(O=C)-MSA-2.

MALDI-TOF-MS spectrum: The measured [M+Na]$^+$ is 2461.46 Dalton, the obtained [M] is 2439.46 Dalton, which is in agreement with the calculated MW of 2739.95 Dalton, as shown in FIG. 14.

Example 25. Synthesis of mPEG-L-G(MSA-2) and Preparation of Nanoparticles, i.e., Synthesis of Monodisperse mPEG$_{44}$-CH$_2$CONH—CH$_2$CH$_2$—SS-di-MSA-2 and Preparation of mPEG$_{44}$-CH$_2$CONH—CH$_2$CH$_2$—SS-di-MSA-2/PLA Nanoparticles The monodisperse mPEG$_{44}$-CH$_2$CONH—CH$_2$CH$_2$—SS-di-MSA-2 was synthesized, and mPEG$_{44}$-CH$_2$CONH—CH$_2$CH$_2$—SS-di-MSA-2/PLA nanoparticles were prepared using the same method as in Example 16.

Figure 15:
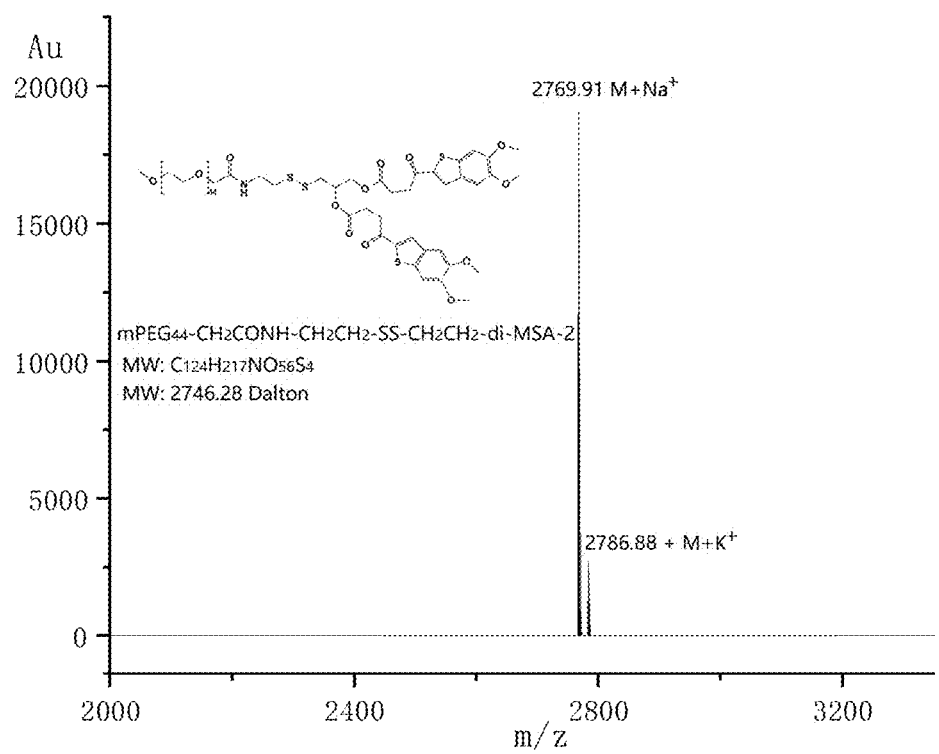
FIG. 15. The MALDI-ToF spectrum of mPEG$_{44}$-CH$_2$CONH—CH$_2$CH$_2$—SS-di-MSA-2.

MALDI-TOF-MS spectrum: The measured [M+Na]$^+$ is 2769.91 Dalton, the obtained [M] is 2746.9 Dalton, which is in agreement with the calculated MW of 2746.28 Dalton, as shown in FIG. 15.

Example 26. Synthesis of mPEG-L-G(NLG-919) and Preparation of Nanoparticles, i.e., Synthesis of Monodisperse mPEG$_{44}$-succinate-NLG-919 ester and Preparation of mPEG$_{44}$-succinate-NLG-919/PLA Nanoparticles The monodisperse mPEG$_{44}$-succinate-NLG-919 was synthesized, and mPEG$_{44}$-succinate-NLG-919/PLA nanoparticles were prepared using the same method as in Example 16.

Figure 16:
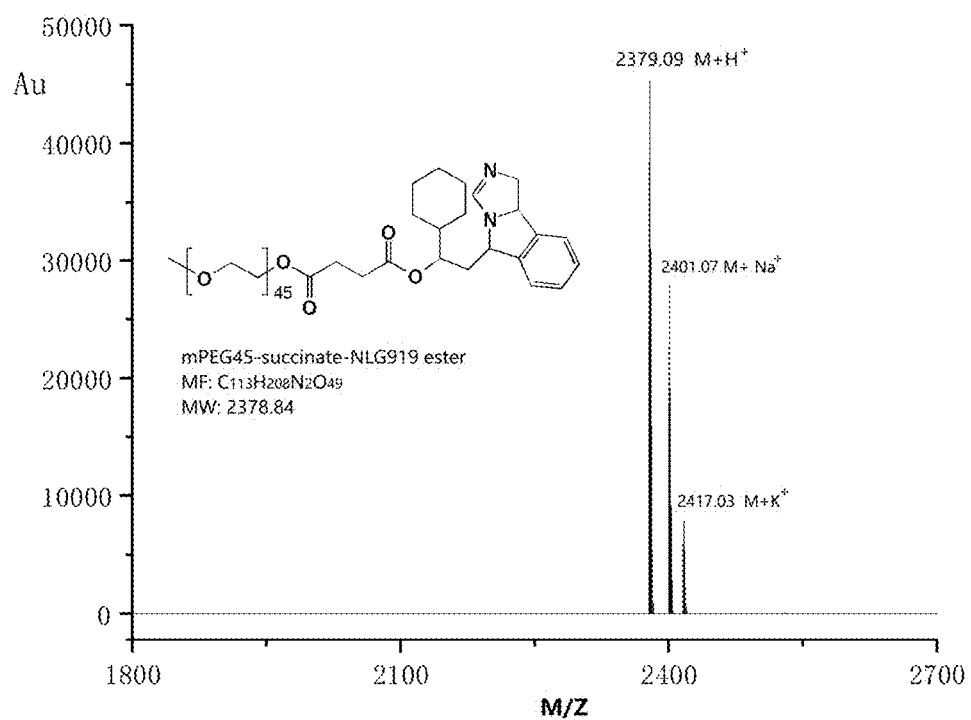
FIG. 16. The MALDI-ToF spectrum of mPEG$_{45}$-succinate-NGL-919.

MALDI-TOF-MS spectrum: The measured [M+H]$^+$ is 2379.09 Dalton, [M+Na]$^+$ is 2401.07 Dalton, [M+K]$^+$ is 2417.03 Dalton, the obtained [M] is 2378.09 Dalton, which is in agreement with the calculated MW of 2378.84 Dalton, as shown in FIG. 16.

Example 27. Synthesis of mPEG-L-G(MHI-148) and Preparation of Nanoparticles, i.e., Synthesis of Monodisperse mPEG$_{44}$-CONH—CH$_2$CH$_2$—SS—CH$_2$CH$_2$O(O=C)-MHI-148 and Preparation of mPEG$_{44}$-CONH—CH$_2$CH$_2$—SS—CH$_2$CH$_2$O(O=C)-MHI-148/PLA Nanoparticles The monodisperse mPEG$_{44}$-CONH—CH$_2$CH$_2$—SS—CH$_2$CH$_2$O(O=C)-MHI-148 was synthesized, and mPEG$_{44}$-CONH—CH$_2$CH$_2$—SS—CH$_2$CH$_2$O(O=C)-MHI-148/PLA nanoparticles were prepared using the same method as in Example 16.

Figure 17:
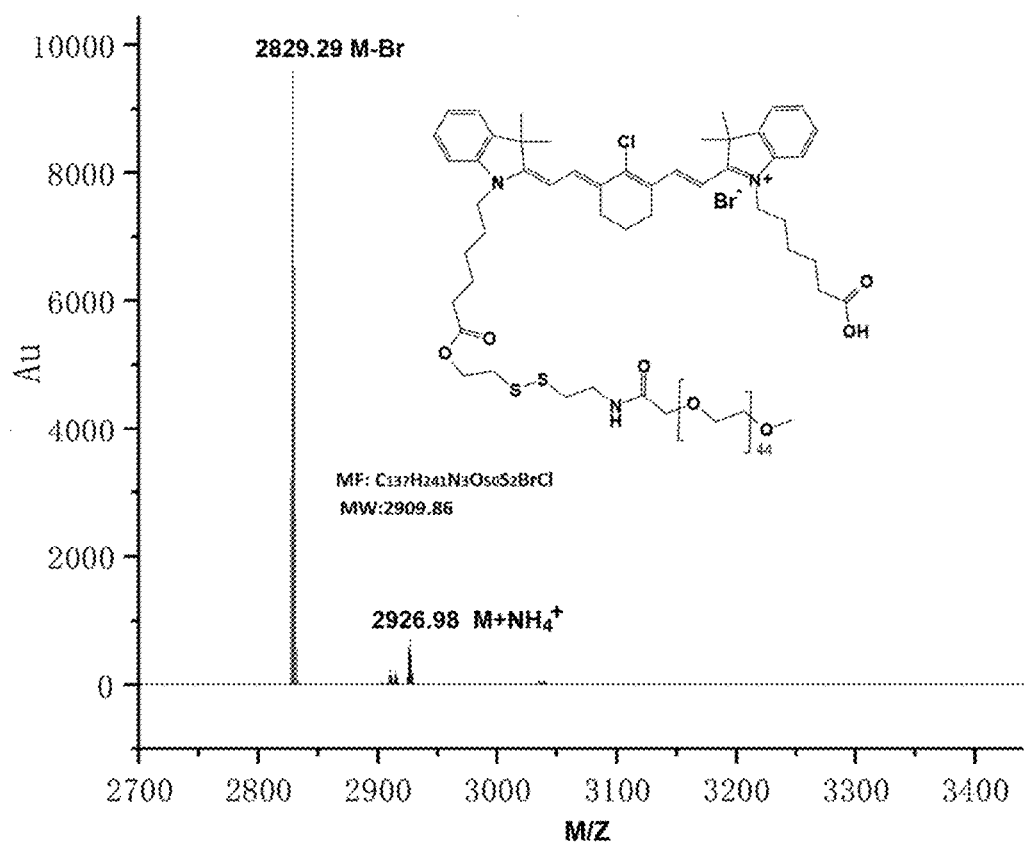
FIG. 17. The MALDI-ToF spectrum of mPEG$_{44}$-CONH—CH$_2$CH$_2$—SS—CH$_2$CH$_2$O(O=C)-MHI-148.

MALDI-TOF-MS spectrum: The measured [M-Br]$^+$ is 2829.29 Dalton, the obtained [M] is 2909.3 Dalton, which is in agreement with the calculated MW of 2909.86 Dalton, as shown in FIG. 17.

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Use of the term "comprising" or "comprises" herein also contemplates that use of "consisting essentially of," "consists essentially of," "consisting of," or "consists of" in its place.

Affirmative recitation of an element anywhere herein should be understood to contemplate both including and excluding that element.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from a group, for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A nanoparticle (PEG-L-G/P) comprising:
   (1) an amphiphilic compound (PEG-L-G) comprising a hydrophilic polyethylene glycol (PEG) covalently linked with a hydrophobic functional agent (G) via L; and
   (2) a hydrophobic polymer (P);
   wherein L is a covalent bond or a linker comprising functional groups which connect the PEG to the G via covalent bonds;
   wherein the G is selected from a compound having certain function, an active pharmaceutical ingredient (API) with therapeutic function, an imaging diagnostic agent, an immune-stimulating agent, a photoelectric-responsive diagnostic agent, a tumor microenvironment-responsive agent, or a combination thereof, and
   wherein the nanoparticle (PEG-L-G/P) has a hydrophobic core comprising the G and the P, and a hydrophilic outer layer comprising the PEG, wherein the PEG is a monodispersed PEG.

2. The nanoparticle of claim 1, wherein the G is dissolved in the hydrophobic core.

3. The nanoparticle of claim 1, wherein the PEG is linear, a branched, dendritic, or comb-shaped, and a molecular weight ranging from 500 to 20,000 Daltons.

4. The nanoparticle of claim 1, wherein the PEG comprises a functional group.

5. The nanoparticle of claim 1, wherein the PEG comprises a methoxy group at one free end of the PEG (mPEG).

6. The nanoparticle of claim 1, wherein the L is a chemical bond, comprising an ester bond, an ether bond, a carbonate bond, an amide bond, a disulfide bond, an anhydride bond, a hydrazone bond, a thioether bond, a selenide bond, a peptide bond, a phosphodiester bond, a glycosidic bond, or stimulation responsive chemical bonds.

7. The nanoparticle of claim 1, wherein the G comprises paclitaxel, tricaplyl paclitaxel, doxorubicin, epirubicin, vinblastine, vincristine, etoposide, irinotecan, topotecan, mitomycin, tamoxifen, ifosfamide, cyclophosphamide, carmustine, SN38 or its derivative, a platinum derivative, MSA-2, DMXAA (Vadimezan), NLG919, IR-26, IR-1061, IR-808, ICG, CH1055, AIE molecule, porphyrin, phthalocyanine, chlorin, texaphyrin, phenothiazinium, rose bengal, indocyanine green (ICG), hypericin, or a combination thereof.

8. The nanoparticle of claim 1, wherein the G comprises two or more types of compounds having different functions.

9. The nanoparticle of claim 1, wherein the polymer P is a polyester or its derivative, a polycarbonate or its derivative, a polyanhydride, or a combination thereof forming a copolymer, wherein the polymer P is optionally biocompatible.

10. The nanoparticle of claim 1, wherein the polymer P is PLA, PCL, PHA, PHB, PHV, PGA, poly(trimethylene carbonate), a derivative thereof, or a combination thereof forming a copolymer.

11. The nanoparticle of claim 1, wherein the polymer P is poly(lactic acid) (PLA).

12. The nanoparticle of claim 1, wherein the mass ratio of PEG-L-G to polymer P in the nanoparticles is about 1:1 to about 20:1 (1-20).

13. The nanoparticle of claim 1, wherein the particle size is about 30 nm to about 200 nm.

14. The nanoparticle of claim 1, wherein the particle size is about 50 nm to about 150 nm.

15. The nanoparticle of claim 1, wherein the particle size is about 70 nm to about 125 nm.

16. The nanoparticle of claim 1 selected from the group consisting of:
Monodisperse mPEG$_{44}$-CH$_2$COO-PTX/PLA Nanoparticle;
Monodisperse mPEG$_{45}$-OCO-PTX/PLA Nanoparticle;
Monodisperse mPEG$_{23x2}$-Lysine-PTX/PLA Nanoparticle;
Monodisperse mPEG$_{44}$-CH$_2$CONHCH$_2$CH$_2$—SS—CH$_2$CH$_2$COO—SN38/PLA Nanoparticle;
Monodisperse mPEG$_{45}$-O(O=C)-MSA-2/PLA Nanoparticle;
Monodisperse mPEG$_{62}$-O(O=C)-MSA-2/PLA Nanoparticle;
Monodisperse mPEG$_{81}$-O(O=C)-MSA-2/PLA Nanoparticle;
(mPEG$_{80}$-CH$_2$COO-PTX and mPEG$_{80}$-CH$_2$CONHCH$_2$CH$_2$—SS—CH$_2$CH$_2$COO—SN38)/PLA Nanoparticle;
(mPEG$_{80}$-CH$_2$COO-PTX and mPEG$_{81}$-O(O=C)-MSA-2)/PLA Nanoparticle;
(mPEG$_{80}$-CH$_2$CONHCH$_2$CH$_2$—SS—CH$_2$CH$_2$COO—SN38 and mPEG$_{81}$-O(O=C)-MSA-2)/PLA Nanoparticle;
Monodisperse mPEG$_{44}$-CH$_2$CONH—CH$_2$CH$_2$—SS—CH$_2$CH$_2$O(O=C)-MSA-2;
Monodisperse mPEG$_{44}$-CH$_2$CONH—CH$_2$CH$_2$—SS-di-MSA-2;
Monodisperse mPEG$_{45}$-succinate-NGL-919; and
Monodisperse mPEG$_{44}$-CONH—CH$_2$CH$_2$—SS—CH$_2$CH$_2$O(O=C)-MI-148.

17. The nanoparticle of claim 2, wherein the nanoparticle is lyophilized to form a powder, wherein the powder is reconstituted in water or an electrolyte aqueous solution to obtain a colloidal solution of the nanoparticle.

18. A method for preparing the nanoparticle (PEG-L-G/P) of claim 1, comprising:
(a) co-dissolving the PEG-L-G compound and the polymer P in one or more organic solvents to form an organic solution;
(b) adding dropwise or continuously the organic solution in step a to an aqueous medium to form a mixture;
(c) mixing the mixture in step b to obtain an emulsion, and optionally adding additional aqueous medium; and
(d) removing the organic solvent(s) to obtain a stable nanoparticle aqueous solution (PEG-L-G/P),
wherein the aqueous medium is water or a phosphate-buffered solution.

19. The method of claim 18, wherein the aqueous medium is a phosphate-buffered solution.

20. A pharmaceutical composition comprising one or more types of the nanoparticle of claim 1, and a pharmaceutically acceptable excipient.

21. The pharmaceutical composition of claim 20; wherein the nanoparticle comprises two or more types of PEG-L-G with G being different.

22. The pharmaceutical composition of claim 20, comprising a plurality of nanoparticles.

23. The pharmaceutical composition of claim 20, wherein the nanoparticle comprises a single type of nanoparticle.

24. The pharmaceutical composition of claim 20, wherein the nanoparticle comprises multiple types of nanoparticle.

25. The pharmaceutical composition of claim 21, wherein the nanoparticle comprise two types of G that are therapeutic drugs.

26. The pharmaceutical composition of claim 21, wherein the nanoparticle comprises two types of PEG-L-G with one type of G that is a therapeutic drug.

27. A method for treating a disease, a condition or a disorder; targeted diagnostics; immunotherapy; drug-immunotherapy; drug-photodynamic therapy; immunotherapy-photodynamic therapy; drug-immunotherapy-photodynamic therapy; or a combination thereof in a mammal, comprising administering a nanoparticle (PEG-L-G/P) of claim 1 or a pharmaceutical composition comprising the nanoparticle to the mammal.

28. The method of claim 27, wherein the method is for treating a disease, condition or disorder in a mammal, wherein G is a therapeutic drug.

29. The method of claim 28, wherein the G is an anti-cancer drug.

30. The method of claim 27, wherein the mammal is a human being.

* * * * *